United States Patent
Nguyen et al.

(10) Patent No.: US 10,935,561 B2
(45) Date of Patent: Mar. 2, 2021

(54) INTEGRATED DIAGNOSTIC INSTRUMENT

(71) Applicant: GenMark Diagnostics, Inc., Carlsbad, CA (US)

(72) Inventors: Michael Thomas Nguyen, Carlsbad, CA (US); Margaret Ginzburg, Encinitas, CA (US); Shawn Andre Hall, San Diego, CA (US); Lisa M. Filippone, San Marcos, CA (US)

(73) Assignee: GenMark Diagnostics, Inc., Carlsbad, CA (US)

( * ) Notice: Subject to any disclaimer, the term of this patent is extended or adjusted under 35 U.S.C. 154(b) by 31 days.

(21) Appl. No.: 15/996,164

(22) Filed: Jun. 1, 2018

(65) Prior Publication Data

US 2019/0369126 A1 Dec. 5, 2019

(51) Int. Cl.
*G01N 35/00* (2006.01)
*C12Q 1/689* (2018.01)
*G16H 50/20* (2018.01)
*G16H 15/00* (2018.01)
*G16H 10/40* (2018.01)
*C12Q 1/04* (2006.01)
*G01N 27/327* (2006.01)

(52) U.S. Cl.
CPC ....... *G01N 35/00722* (2013.01); *C12Q 1/689* (2013.01); *G01N 27/3276* (2013.01); *G16H 10/40* (2018.01); *G16H 15/00* (2018.01); *G16H 50/20* (2018.01); *C12Q 1/04* (2013.01); *G01N 2035/0091* (2013.01)

(58) Field of Classification Search
None
See application file for complete search history.

(56) References Cited

U.S. PATENT DOCUMENTS

| | | | |
|---|---|---|---|
| 6,600,026 | B1 | 7/2003 | Yu |
| 6,740,518 | B1 | 5/2004 | Duong et al. |
| 7,644,898 | B2 | 1/2010 | White et al. |
| 8,155,886 | B2 | 4/2012 | Cross et al. |
| 8,501,921 | B2 | 8/2013 | Bamdad et al. |
| 9,127,308 | B2 | 9/2015 | Braven et al. |
| 9,500,663 | B2 | 11/2016 | Morgue et al. |
| 9,557,295 | B2 | 1/2017 | Kayyem |

(Continued)

OTHER PUBLICATIONS

Canovas-Segura et al. Development of a clinical decision support system for antibiotic management in a hospital environment. Prog Artif Intell, vol. 5, pp. 181-197 (Year: 2016).*

(Continued)

*Primary Examiner* — Olivia M. Wise
(74) *Attorney, Agent, or Firm* — Brinks Gilson & Lione

(57) ABSTRACT

A pathogen detection device is provided. The pathogen detection device may include a pathogen detector circuit configured to detect a target analyte in a patient sample, determine the presence of a pathogen from the target analyte, and generate a detection result including the identity of the pathogen and resistance genes (if any); and a decision support generator circuit configured to generate decision support information for the pathogen by application of user configurable rules to the detection result, wherein each of the configurable rules include a logic expression that indicates the corresponding decision support information of the rule to be included in the detection report.

15 Claims, 22 Drawing Sheets

(56) References Cited

U.S. PATENT DOCUMENTS

| | | | |
|---|---|---|---|
| 9,598,722 B2 | 3/2017 | Wright et al. | |
| 9,891,215 B2 | 2/2018 | Kayyem et al. | |
| 2004/0122709 A1 | 6/2004 | Avinash et al. | |
| 2006/0218010 A1 | 9/2006 | Michon et al. | |
| 2010/0297645 A1* | 11/2010 | Pierik | C12Q 1/6888 435/6.1 |
| 2014/0194305 A1 | 7/2014 | Kayyem et al. | |
| 2014/0322706 A1 | 10/2014 | Kayyem et al. | |
| 2015/0323555 A1 | 11/2015 | Kayyem et al. | |
| 2016/0129437 A1 | 5/2016 | Kayyem et al. | |
| 2018/0095100 A1 | 4/2018 | Nguyen et al. | |
| 2019/0062809 A1* | 2/2019 | Brown | G01N 27/3277 |

OTHER PUBLICATIONS

Proctor et al. Drools Documentation. Technical Report, pp. 1-297 (Year: 2008).*

Stockemer "How do HL7 and XML co-Exist in Clinical Interfacing?" Health Standards Aug. 10, 2007, pp. 1-6 (Year: 2007).*

Martinez et al. Graphical user interfaces. WIREs Comp Stat 2011, vo. 3, pp. 119-133 (Year: 2011).*

"Randomized Trial of Rapid Multiplex PCR-Based Blood Culture Identification and Susceptibility Testing," Banerjee et al., 10 pages, 2015.

"Randomized Trial of Rapid Multiplex Polymerase Chain Reaction-Based Blood Culture Identification and Susceptibility Testing," Banerjee et al., Clinical Infections Diseases, pp. 1071-1080, 2015.

Non-Final Office Action dated Sep. 5, 2018 issued in U.S. Appl. No. 15/298,729, 84 pages.

Non-Final Office Action dated Oct. 1, 2018 issued in U.S. Appl. No. 14/807,000, 31 pages.

International Search Report and Written Opinion in International Application No. PCT/US2019/022505, dated Jun. 24, 2019, 17 pages.

Sheldon, "Detection of Pathogens in Blood for Diagnosis of Sepsis and Beyond" Ebiomedicine, vol. 9, dated Jun. 23, 2016, 2 pages, XP055595670.

* cited by examiner

| GenMarkDx | | | |
|---|---|---|---|
| BCID-GP Detection Report | | | |
| Accession ID: VPL6300JG | | Date/Time Completed: | 04/19/2018 9:24 AM |
| Patient ID: | | Bay Location: | D1 |
| Protocol: BCID-GP 1.1.30.43 | | Cartridge ID: | 410003 |
| Software Version: 1.0.6.5 | | Cartridge Lot Number: | 1 |
| Operator: Internal | | Cartridge Expiration Date: | 05/19/2018 |
| Instrument Serial Number: 000000 | | | |
| SUMMARY | | | |
| Enterococcus, Enterococcus faecium, Staphylococcus, Staphylococcus aureus, Pan Gram- Negative, mecA and vanA detected. WARNING: A Not Detected result for a resistance gene does not indicate susceptibility to antimicrobials. Gram-postive bacteria can be restant to antimicrobials by mechanisms other than carrying the resistance genes detected by BCID-GP assay. | | | |
| RESULTS | | | |
| Bacterial Target | Result | Bacterial Target | Result |
| Bacillus cereus group | Not Detected | Streptococcus | Not Detected |
| Bacillus subtilis group | Not Detected | Streptococcus agalactiae | Not Detected |
| Corynebacterium | Not Detected | Streptococcus anginosus group | Not Detected |
| ✓ Enterococcus | Detected | Streptococcus pneumoniae | Not Detected |
| Enterococcus faecalis | Not Detected | Streptococcus pyogenes | Not Detected |
| ✓ Enterococcus faecium | Detected | | |
| Lactobacillus | Not Detected | Pan Targets | |
| Listeria | Not Detected | Pan Candida | Not Detected |
| Listeria monocytogenes | Not Detected | ✓ Pan Gram-Negative | Detected |
| Micrococcus | Not Detected | | |
| Propionibacterium acnes | Not Detected | Resistance Gene Target | |
| ✓ Staphylococcus | Detected | ✓ mecA | Detected |
| ✓ Staphylococcus aureas | Detected | mecC | Not Detected |
| Staphylococcus epidermidis | Not Detected | ✓ vanA | Detected |
| Staphylococcus lugdunensis | Not Detected | vanB | Not Detected |
| 1020 | | Internal Control | PASS |
| COMMENTS | | | |
| Methicillin (oxacillin)-susceptible Staphylococcus aureus. Preferred therapy is an anti- staphylococcal beta-lactam antibiotic, unless clinically contraindicated. Probable methicillin- resistant Staphylococcus aureus (MRSA) further testing in progress. MRSA is predictably resistant to beta-lactum antibiotics (except ceftaroline). Patient requires contact precautions if hospitalized. Semi-Urgent Result. Vancomycin-resistant enterococcus. Patient requires contact precautions if hospitalize. Semi-Urgent Result. | | | |
| FLAGS | | | |
| 5001: Manual start of a sample test | | | |

(1010 points to right Result column; 1020 points to left table area)

Operator Signature    Date        Approver Signature    Date

FIG. 11

| GenMarkDx |||||
|---|---|---|---|---|
| BCID-GP Detection Report |||||
| Accession ID: | 52825172-PM1-140 || Date/Time Completed: | 04/19/2018 9:34 AM |
| Patient ID: |  || Bay Location: | D2 |
| Protocol: | BCID-GP 1.1.30.43 || Cartridge ID: | 420001 |
| Software Version: | 1.0.6.5 || Cartridge Lot Number: | 11 |
| Operator: | Internal || Cartridge Expiration Date: | 06/19/2018 |
| Instrument Serial Number: | 000000 ||||
| SUMMARY |||||
| Listeria, Staphylococcus, Staphylococcus aureus, Staphylococcus lugdunensis, streptococcus, streptococcus pyogenes and Pan-Gram Negative detected. |||||
| WARNING: A Not Detected result for a resistance gene does not indicate susceptibility to antimicrobials. Gram-postive bacteria can be restant to antimicrobials by mechanisms other than carrying the resistance genes detected by BCID-GP assay. |||||
| RESULTS |||||
| Bacterial Target | Result || Bacterial Target | Result |
| Bacillus cereus group | Not Detected | ✓ | Streptococcus | Detected |
| Bacillus subtilis group | Not Detected || Streptococcus agalactiae | Not Detected |
| Corynebacterium | Not Detected || Streptococcus anginosus group | Not Detected |
| ✓ Enterococcus | Not Detected || Streptococcus pneumoniae | Not Detected |
| Enterococcus faecalis | Not Detected | ✓ | Streptococcus pyogenes | Detected |
| Enterococcus faecium | Not Detected ||||
| Lactobacillus | Not Detected || Pan Targets ||
| ✓ Listeria | Detected || Pan Candida | Not Detected |
| Listeria monocytogenes | Not Detected | ✓ | Pan Gram-Negative | Detected |
| Micrococcus | Not Detected ||||
| Propionibacterium acnes | Not Detected || Resistance Gene Target ||
| ✓ Staphylococcus | Detected || mecA | Not Detected |
| ✓ Staphylococcus aureas | Detected || mecC | Not Detected |
| Staphylococcus epidermidis | Not Detected || vanA | N/A |
| ✓ Staphylococcus lugdunensis | Detected || vanB | N/A |
|  ||| Internal Control | PASS |
| COMMENTS |||||
| Methicillin (oxacillin)-susceptible Staphylococcus aureus. Preferred therapy is an anti- staphylococcal beta-lactam antibiotic, unless clinically contraindicated. |||||
| FLAGS |||||
| 5001: Manual start of a sample test |||||

Operator Signature      Date      Approver Signature      Date

FIG. 12

GenMarkDx

BCID-GP Detection Report

| | | | |
|---|---|---|---|
| Accession ID: | V0726-5C-282 | Date/Time Completed: | 04/19/2018 9:43 AM |
| Patient ID: | | Bay Location: | D3 |
| Protocol: | BCID-GP 1.1.30.43 | Cartridge ID: | 430001 |
| Software Version: | 1.0.6.5 | Cartridge Lot Number: | 11 |
| Operator: | Internal | Cartridge Expiration Date: | 07/19/2018 |
| Instrument Serial Number: | 000000 | | |

SUMMARY

Corynebacterium, Enterococcus, Enterococcus faecalis, Lactobacillus, Streptococcus, Streptococcus anginosus group, Streptococcus Pyogenes and vanB detected.

WARNING: A Not Detected result for a resistance gene does not indicate susceptibility to antimicrobials. Gram-positive bacteria can be restant to antimicrobials by mechanisms other than carrying the resistance genes detected by BCID-GP assay.

RESULTS

| Bacterial Target | Result | Bacterial Target | Result |
|---|---|---|---|
| Bacillus cereus group | Not Detected | ✓ Streptococcus | Detected |
| Bacillus subtilis group | Not Detected | Streptococcus agalactiae | Not Detected |
| ✓ Corynebacterium | Detected | ✓ Streptococcus anginosus group | Detected |
| ✓ Enterococcus | Detected | Streptococcus pneumoniae | Not Detected |
| ✓ Enterococcus faecalis | Detected | ✓ Streptococcus pyogenes | Detected |
| Enterococcus faecium | Not Detected | | |
| ✓ Lactobacillus | Detected | Pan Targets | |
| Listeria | Not Detected | Pan Candida | Not Detected |
| Listeria monocytogenes | Not Detected | Pan Gram-Negative | Not Detected |
| Micrococcus | Not Detected | | |
| Propionibacterium acnes | Not Detected | Resistance Gene Target | |
| Staphylococcus | Not Detected | mecA | N/A |
| Staphylococcus aureas | Not Detected | mecC | N/A |
| Staphylococcus epidermidis | Not Detected | vanA | Not Detected |
| Staphylococcus lugdunensis | Not Detected | ✓ vanB | Detected |
| | | Internal Control | PASS |

1020

1010

COMMENTS

Methicillin (oxacillin)-susceptible Staphylococcus aureus. Preferred therapy is an anti- staphylococcal beta-lactam antibiotic, unless clinically contraindicated.

FLAGS

5001: Manual start of a sample test

Operator Signature    Date    Approver Signature    Date

FIG. 13

Antibiotic Treatment Algorithm Reference for positive blood Cultures

| Common empiric therapy | Gram Stain Morphology | Gram Stain specific therapy | Common organism ID | Resistance gene | Treatment decision support based upon diagnostic results | Further treatment decision support based upon diagnostic results |
|---|---|---|---|---|---|---|
| beta-lactam often combined with an aminoglycoside or a flouroquinolone, and according to the medical context antiviral and/or antifungal drugs may be added | Gram-positive cocci in clusters | Vancomucin or daptomycin | Staphylococcu | mecA/ mecC | Considered a definitive results: -If S. aureus and mecA/C : definitive MRSA treat with vancomycin -If S. aureus and no mec: definitive MSSA; treatment is de-escalated to a beta-lactam (eg. nacfcillinv or cefazolin) | mecA/C have high PPV &NPV (no other mechanisms of resistance). Culture may be ues to confirm no other organism are present in the blood and if so ASt can be discontinued. |
| | Gram-positive cocci in chains | Ampicillin or vancomycin | Enterococcus | vanA/ vanb | Enterococci are inherently resistant to many classes of abx that are active against the GPC (eg. cephalosprins & macrolids) Considered a definitive results: -If Enterococcus and vanA/B: VRE: treatment guided by antibiogram (ampicillin is treatment of choice if susceptible) -If Enterococcus and no van: treatment is guided by antibiogram (ampicillin or | VanA/B results have a high PPV & NPV. ampicillin or similar is generally used for treatment, although susceptibilities (AST) may be run to confirm. If Amp resistant doxy or other will be used to treat. |
| | Gram-positive rods | Penicillins or vancomycin | Corynebacterium, Cutibacterium, lactobacillus, Bacillus, etc. | N/A | If ePlex results is a common contaminant (Corynebacterium, C. acnes, Lactobacillius, B. subtils) and infection is only present in one blood culture bottle, treatment may be discontinued/de-esclated. If ePlex results is B. cereus or Listeria treatment will be escalated based on antibiogram (eg.clindamycin for B. cereus) | GP rodsbacilli are generally Presumed to be contaminants but could be B. cereus, Listria or others; ePlex enables rapid de-scalation of treatment. |
| | Gram-Negative rods (bacilli) | 3rd or 4th generation cephalosparin (eg. ceftriaxone or piperacillin/ tazobactam; with addition of fluoroquinolone for clinically | Many (leg klebsiella acintobacier, Pseudomonas, others) | CTX-M | Positive resistnce gene drives antibiotic escalation; Any GN organism with ESBL or Carbapenemase gene is very serious and antibiotic selection may be limited (eg. last line abx like colistin may be required) Combining ID & resistance gene result with antibiogram allows for treatment to be narrowed ahead of final AST results. | Gram negative antibiotic resistane can be caused by a number of resistance mechanism. The ePlex BCID-GN assay includes the most common resistance genes, however no molecular assay can cover all of them. Therefore even if the test is negative for all resistance genes, the organism may still carry different resistance mechanism. Combining the result wth the antibiogram can help narraow to the best |
| | | | | KPC | | |
| | | | | OXA | | |
| | | | | NDM | | |
| | | | | IMP | | |
| | | | | VIM | | |
| | Gram Stain Morphology | | B. fragilis Fusobacterium | N/A | Piperacillintazobactam or metronidzole | May not be covered by standard empiric therapy, ID is necessary to ensure appropriate treatment |
| | Gram-Negative cocci | | Staphylococcu | N/A | 3rd generation cephalosporin (eg. ceftriaxone) | Resistant to vancomycin and aminoglycosides |
| | Fungi | Echinocandin or azole (eg. fluconazole) | Candida | N/A | Species ID is often predictive of appropriate treatment. Depending upon ID treatment may be escalated to amphoteric B or an echinocandin (eg. micafungin) | Emerging Candida are often fluconazole resistant and other emerging non-candida fungi are often resistant to echinocandins. |

FIG. 15

INTEGRATED DIAGNOSTIC INSTRUMENT

TECHNICAL FIELD

This application relates to medical instruments and, more particularly, to medical instruments for the detection and/or analysis of target analytes from patient samples.

BACKGROUND

Bloodstream infections (BSIs) are associated with significant morbidity, mortality, and increased length of stay (LOS). Delayed administration of effective antibiotics increases the risk of mortality, and therefore correct selection of an antibiotic regimen early in the treatment process is paramount. Delayed identification of the causative organism and antimicrobial resistance or susceptibility may often be responsible for delays in optimal antimicrobial therapy. Rapid diagnostic testing (RDT), which includes tests, such as polymerase chain reaction (PCR), matrix-assisted laser desorption/ionization-time of flight mass spectrometry (MALDI-TOF MS), and peptide nucleic acid fluorescent in situ hybridization (PNA-FISH), has improved upon conventional microbiological methods, reducing time to organism identification, optimizing antimicrobial therapy, and subsequently improving clinical outcomes, including mortality. Commercial molecular RDTs (mRDT) are available for direct testing of positive blood culture bottles (BCBs), providing timelier results than conventional subculture and phenotypic susceptibility testing. Examples of commercially available mRDTs devices include Biofire's FILMARRAY® and GenMark's ePLEX®.

Rapid pathogen identification methods are associated with decreased mortality, decreased length of stay (LOS), and decreased cost. This is because rapid pathogen identification methods allow clinicians to quickly initiate "pathogen-directed" therapy and appropriately escalate or de-escalate antibiotic therapy, as needed. Indeed, timely initiation of effective therapy is a critical step in the management of patients with sepsis. Recent studies have shown that patients with severe sepsis or septic shock showed an increased likelihood of death of 7.6% for every hour in which appropriate antibiotic therapy is not applied. Thus, survival rates have been significantly increased as diagnosis times have been reduced. But, despite the availability of a rapid test result (for example, results indicating the presence or the absence of mecA gene), providers may fail to modify antibiotic therapy without pharmacist or specialist intervention.

Indeed, studies have shown that when rapid molecular testing results are delivered with guidance from an antimicrobial stewardship team there is frequent and timelier antibiotic de-escalation. Yet, to date, delivery of pathogen detection results together with decision support information, such as guidance regarding antimicrobial prescribing, by a detection device is not done.

Molecular laboratories typically report results that are very technical in nature. Thus, once a pathogen has been identified, physicians may fail to modify or delay modifying a patient's antibiotic therapy. This is because the physician does not know how to interpret the results, does not know the correct antibiotic treatment, or must utilize tools to investigate the proper treatment. Clinicians seeking to find decision support information using key terms (such as a detected pathogen) entered into search engines or other processes often cannot efficiently find the data they are looking for. Moreover, once a set of search results is provided, some clinicians may not be able to use the results in a meaningful way. Additionally, some clinicians may not possess the skill or time necessary for developing precise search terms in order to ensure that results of a search are comprehensive and complete. Alternatively, or in addition, clinicians also may not possess the skill or time necessary for interpreting large volumes of data returned in response to searches.

Additionally, in many hospitals before treatment can be modified clinicians must obtain approval from an antibiotic stewardship team member, infectious disease clinician or pharmacist. Approval wait times can be prolonged because, for example, physicians may prefer not to contact supervising providers at night regarding non-urgent de-escalation questions. Further, in complex clinical scenarios when critically ill or immunocompromised patients or patients with polymicrobial infections are on multiple broad-spectrum antibiotics, providers may prefer discussion with infectious disease specialists prior to modifying antimicrobial management. Thus, rapid pathogen and antimicrobial resistance detection reported with treatment decision support information may optimize antibiotic prescribing for infections.

Moreover, antibiotic stewardship is extremely complex and changes rapidly. Different regions, hospital networks, hospitals and physician offices have different environments and different policies for implementing antibiotic treatment. Thus, a one-size-fits-all approach to reporting results with treatment care guidelines has traditionally not been feasible for detection devices. As such a need for reporting results with customized treatment decision support information is needed.

BRIEF SUMMARY OF INVENTION

In one example, a method for aiding clinicians to interpret or act on diagnostic results for a patient infected or possibly infected with a microorganism is provided. A pathogen may be detected in a patient sample by a detection device or diagnostic instrument. A detection result, which includes an identity of the pathogen or resistance gene (if any), may be generated by the detection device. In addition, treatment decision support may be generated by the same detection device that detected the pathogen. The decision support information may be generated by the detection device by applying one or multiple rules to the detection result, where each respective rule includes at least one corresponding condition for including a corresponding templated comment in the decision support report. The templated comment may include user-customizable text. The condition for including the templated comment may comprise a logic expression that evaluates to either true or false or an equivalent thereof, like "one" or "zero". If the logic expression evaluates to true, for example, when the corresponding rule is applied to the detection results, then the detection device may include the templated comment in the decision support report; alternatively, if the logic expression evaluates to false, then the detection device may not include the templated comment or utilize a different templated comment in the decision support report. The condition for including at least one of the templated comments in the decision support report may depend on the identity of the pathogen and/or the result (detected vs not detected). The decision support information (aka templated comment) and the detection result may be provided to a user together or separately. A clinician may analyze the decision support information and the detection result and administer an appropriate antibiotic to a patient.

In preferred examples, the clinician will modify treatment from a broad-spectrum antibiotic and/or combination therapy to a monotherapy.

An advantage of the systems and methods described herein may provide rapid results automatically delivered with real-time decision support that assists clinicians to interpret and act on results. By generating decision support information with a detection device based on the identified pathogen and/or other data in the detection results, the detection device may facilitate the clinician treating patients faster and/or with providing the patient with more effective care than with other detection devices. Alternatively, or in addition, a technical advantage of the systems and methods described herein may be that the innovative logical model loaded into memory of the detection device enables the detection device to generate the relevant decision support information, whereas known detection devices are unable to do so. This innovative detection device, which generates the decision support information, may have the ability to save a patient's life due to its speed of operation. Alternatively, or in addition, the systems and methods described herein may electronically deliver molecular (detection) results with guidance regarding antimicrobial prescribing, infection control and patient isolation directly to the clinician.

In some examples, a decision support generator is provided which is configured (1) to avoid delayed administration of directed antimicrobial therapy (treatment modification in 0-6 hours, preferably 0-5 hours, preferably 0-4 hours, preferably 0-3 hours, preferably 0-3 hours, preferably 0-1 hours, preferably 0-0.5 hours, preferably 0.5-5 hours (2) to ensure compliance with antimicrobial stewardship teams' policies, procedures and guidelines, (3) to enforce diverse policies for different regions, hospitals and physician offices using the decision support generator to allow users to flexibly tailor, in real time, their own rules, (4) where appropriate, to apply an administrative hierarchy within the decision support generator.

In some examples, diagnostic results are screened by a rules engine also referred to herein as a decision support generator and templated comments are automatically delivered along with the diagnostic result. The user may configure the decision support generator with rules directly on the instrument. The user may configure the decision support generator with rules on the instrument via a remote connection to the instrument using a remote rules configuration interface 107r. The rules may be configured to provide user selectable scope of application. A result is processed and templated comments applied against the rule set applicable thereto in order of narrowing scope of the rules (target hierarchy/administration hierarchy). That is, laboratories, hospital networks, hospitals and clinicians may each configure rules applicable to their own laboratory, hospital network, hospital or clinician office independently of rules applicable to any other laboratory, hospital network, hospital or clinician office serviced by the instrument.

BRIEF DESCRIPTION OF THE DRAWINGS

The examples may be better understood with reference to the following drawings and description. The components in the figures are not necessarily to scale. Moreover, in the figures, like-referenced numerals designate corresponding parts throughout the different views.

FIG. 1*a* is a schematic diagram of an example of a system (direct creation of rule on instrument) to aid in providing decision support to a clinician to treat a patient infected or possibly infected with a microorganism. FIG. 1*b* is a schematic diagram of an example of a system (remote creation of rule on configuration instrument) to aid in providing decision support to a clinician to treat a patient infected or possibly infected with a microorganism; FIG. 1*c* is a schematic diagram of an example of a system (remote creation of rule on configuration instrument and remote decision support generator) to aid in providing decision support to a clinician to treat a patient infected or possibly infected with a microorganism.

FIG. 5*a* is a flow chart of an example of operations that the decision support generator may perform when applying the rules to the detection results; FIG. 5*b* is a flow chart of an example of operations that the decision support generator may perform when applying the rules to the detection results (administrative hierarchy).

FIG. 5*c* is a flow chart of an example of operations that the decision support generator may perform when applying the rules to the detection results (result hierarchy). FIG. 5*d* is a flow chart of an example of operations that the decision support generator may perform when determining which rules will be considered during the apply rule step (rule application).

FIG. 11 illustrates an example of a detection report that includes detection results and decision support information.

FIG. 12 illustrates a second example of a detection report.

FIG. 13 illustrates a third example of a detection report.

FIG. 15 is a chart showing the treatment methodology and possible templated comments that can be applied to a detection report.

FIG. 17*a* shows a simple target logic condition and FIG. 17*b* shows a more complicated target logic condition.

DETAILED DESCRIPTION

Figure 1A:
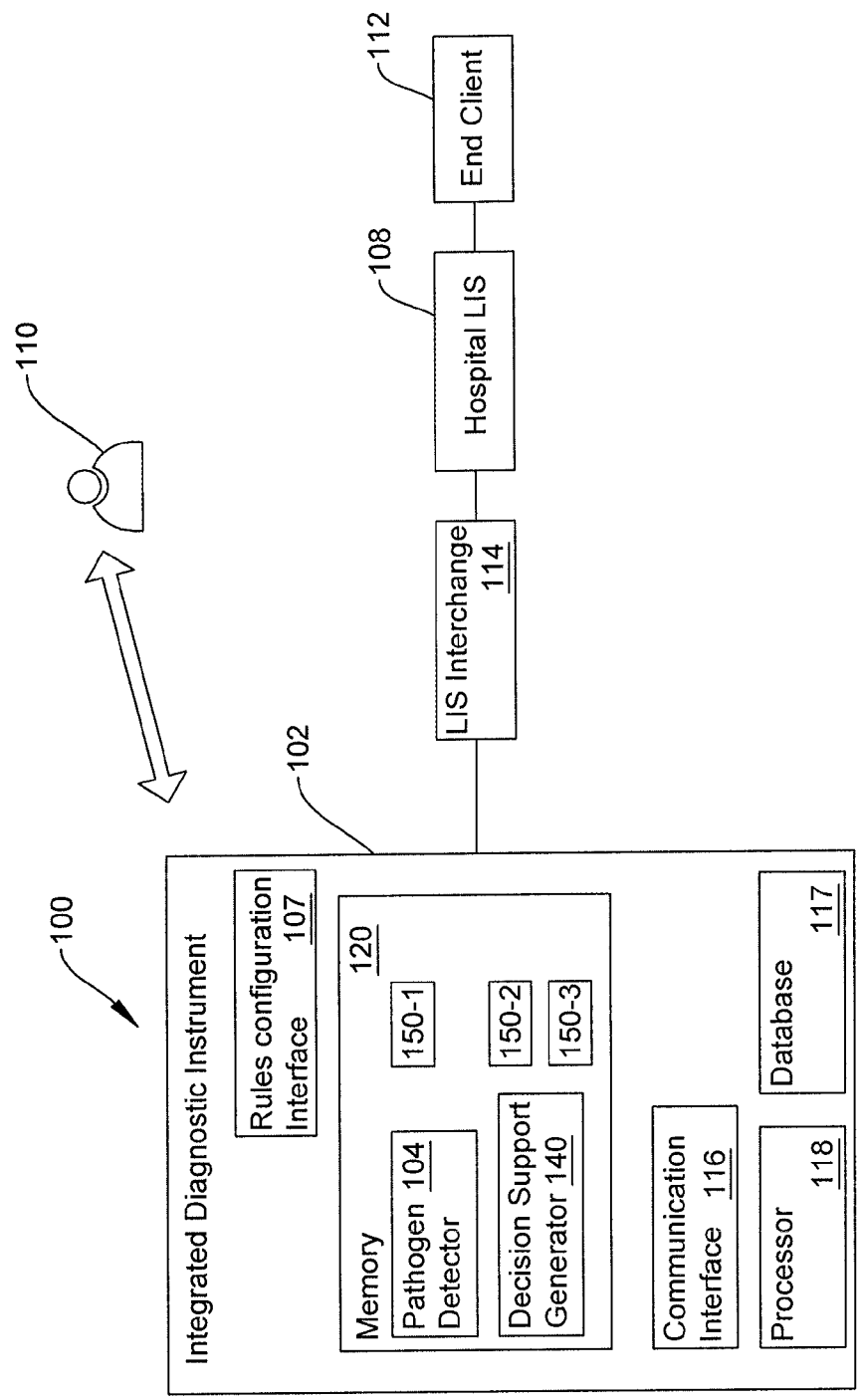
FIGS. 1*a-c*.

While aspects of the subject matter of the present disclosure may be embodied in a variety of forms, the following description and accompanying drawings are merely intended to disclose some of these forms as specific examples of the subject matter. Accordingly, the subject matter of this disclosure is not intended to be limited to the forms or examples so described and illustrated.

Unless defined otherwise, all terms of art, notations and other technical terms or terminology used herein have the same meaning as is commonly understood by one of ordinary skill in the art to which this disclosure belongs. All patents, applications, published applications and other publications referred to herein are incorporated by reference in their entirety. If a definition set forth in this section is contrary to or otherwise inconsistent with a definition set forth in the patents, applications, published applications, and other publications that are herein incorporated by reference, the definition set forth in this section prevails over the definition that is incorporated herein by reference.

Introduction

Pathogen and antimicrobial resistance detection reported with templated comments may lead to earlier administration of directed antimicrobial therapy, promote earlier de-escalation of broad-spectrum agents, quicker appropriate de-escalation of therapy (e.g., switching from vancomycin to cefazolin if methicillin-susceptible *S. aureus* is identified), quicker appropriate escalation of therapy (e.g., switched from ceftriaxone to cefepime if *Pseudomonas aeruginosa* is identified), and potentially result in better outcomes, fewer antibiotic-associated adverse effects (e.g., *Clostridium difficile* infection), and less emergence of antimicrobial-resistant organisms.

A method for treating patients infected with or suspected of being infected with a microorganism may be provided. A patient sample may be loaded into a diagnostic instrument. A diagnostic result or detection result may be obtained. The diagnostic result may be provided to a configurable decision support generator. The decision support generator may apply rules created by a user. The decision support generator may determine if any one of the rules have been satisfied. The decision support generator may automatically apply an action in accordance with the rule wherein the action may be applying an approved templated comment, warning templated comment, or rejection templated comment and automatically reporting the templated comment to the clinician. The clinician evaluates the templated comment and may in some cases intervene (escalate or de-escalate treatment) in the treatment of the patient.

The user created rules may comprise IF, THEN, ELSE statements. To determine if any one of the rules have been satisfied, patient data elements may be gathered, such as patient age, gender, allergies, other medications taken by the patient etc. The patient data elements may be processed by the decision support generator to determine if any one of the rules have been satisfied. The microorganism detected may be processed by the decision support generator to determine if any one of the rules have been satisfied. The presence of resistance genes may be processed by the decision support generator to determine if any one of the rules have been satisfied. Combinations of patient data, target detected, resistance genes and other data elements may be processed by the decision support generator to determine if any one of the rules have been satisfied.

Pathogen and susceptibility detection reported with templated comments may avoid the need for costly around-the-clock antimicrobial stewardship team over-sight.

Examples disclosed herein include a method, a device, a kit, and/or a system of delivering test results along with templated comments guiding test result interpretation and antimicrobial prescribing.

Examples disclosed herein include a method, a device, a kit, and/or a system of delivering test results along with templated comments guiding test result interpretation and antimicrobial stewardship team recommendations for antimicrobial prescribing.

The system may bypass the need for a person, such as a clinician, to generate a query or for the system to have a rule query language engine to generate a query based on a detection result. The system may avoid the need for a system comprising artificial intelligence and/or an implementation of any other algorithm to convert a query generated by a person into a search that may be used to search a rule repository. Instead, the system may receive a data output from the diagnostic engine and searches its user created rule repository. Then a rule processing engine formulates an instruction(s) based on one or more rules produced by the search of the rule repository then generates a signal based on the instruction.

A rules-based reporting system includes a rule repository (item 304 in FIG. 3) to store a plurality of rules relating to medical intervention is disclosed herein.

Detection System

Sample-to-Answer System

In some examples, the decision support generator is part of a sample-to-answer system. The sample-to-answer system may combine an automated nucleic acid testing system with communication capabilities to streamline the diagnostic workflow from physician order entry to the release of the final report with accurate, actionable test results. US Patent Application Publication US 2018/0095100 A1 by Nguyen et al., which describes examples of some sample-to-answer systems that do not include the decision support generator, is hereby incorporated by reference in its entirety.

The sample-to-answer system may reduce avoidable medical errors. Preventable medical errors are now the third leading cause of death in the United States at more than 250,000 per year. Automating information transfer has been shown to be effective in reducing many common errors, including patient identity checking and result transcription. The sample-to-answer system is uniquely designed with patient safety features to help address this challenge in the lab.

The sample-to-answer system, in some examples, may be a single diagnostic instrument.

Bi-Directional Laboratory Information System (LIS)

The sample-to-answer system may include a bi-directional LIS (also referred to as, for example, an LIS communication system, or LIS interchange, or a bi-directional LIS communication system) to automate and accelerate order entry and results reporting. Alternatively, the sample-to-answer system may include any other suitable communication system such as a communication interface 116 in FIG. 1*a*.

The communication system, such as the LIS communication system, may enable bi-directional reporting. Specifically, when a sample is collected, a physician may create a test order called a physician test order. The physician test order enables the physician to specify a sample stability time (the time the sample is stable before results could be affected). The physician test order will further allow the physician to specify the time that a physician test order should remain on the physician test order list before processing.

Physician→Hospital LIS

After the physician test order is generated, the physician test order is sent to the hospital's laboratory information system (LIS), a computer software that processes, stores and manages data from all stages of medical processes and tests. The physician test order is accepted by the Hospital LIS and a pending test order (PTO) is created once the patient sample is received and accessioned by the lab into the hospital LIS.

Hospital LIS→LIS Interchange

The hospital's LIS sends the PTO to an LIS interchange (associated with the diagnostic instrument), which converts the PTO request from an HL7 (Health Level-7) or ASTM (American Society for Testing and Materials) format to a CSV (comma-separated values) format and the PTO is now referred to as a test order, an interchange order, a formatted test order, or a similar term. HL7 and ASTM are a set of standards used in the transfer of information between clinical instruments and Laboratory Information Systems. In this way, the sample-to-answer system is able to communicate with any hospital LIS because the hospital LIS may be driven by multiple standard messaging protocols, such as HL7 and ASTM. In this way, if the hospital's LIS system is updated, the LIS interchange may be remotely updated without requiring an update on the clinical instrument.

The sample-to-answer system 100 in FIG. 1a further supports a "flat file format", in other words, a non-standard file support for laboratories without automated interfaces (HL7 or ASTM). As such, tests may be imported and/or exported manually in a text format, CSV, TXT, or XML (Extensible Markup Language) formats. Automatic results may be released in XML format to a shared network location.

When the LIS interchange receives the PTO and reformats it to a test order, the test order is auto published with information associated with the PTO/sample, such as patient identification, accession number (accession ID), test ordered (for example, BCID-GP, BCID-GN, and BCID-FP), patient type (for example, pediatric, intensive care, and maternity), patient location (for example, pediatrics, ER, maternity), and/or time stamps, such as sample collection, sample ordering, time received at central receiving, central receiving sort, transport to lab, and/or accession of sample. The PTO may include other identifying information such as ordering clinician, hospital, hospital network, which may be published in the test order. These time stamps provide real-time monitoring by the instrument software of pending test order turn-around time. Any information included in the PTO can be used by the instrument 102 in FIG. 1a as a drop drown data element which can be selected by a user when configuring a rule.

LIS Interchange→Clinical Instrument's CPU

The automated nucleic acid testing system with communication capabilities may be referred to as a "Clinical instrument" of the sample-to-answer system. After the LIS interchange receives the test order, the LIS interchange sends the test order to the sample-to-answer system's (clinical instrument's also referred to as a base station) processor.

The sample-to-answer system may support both serial and Ethernet RJ45 input/output connections to one or more hospital LIS. Alternatively, or in addition, the sample-to-answer system may support any other physical or wireless communication interface standard.

A Sample Stability feature or a Sample Stability time enables the user to specify the stability time on a per assay basis. The software tracks PTO orders and sends an alert notification when an order has violated the threshold for sample stability. The sample-to-answer system may include "cleanup rules" to automatically delete outstanding pending test orders. For example, the "cleanup rules" may delete a PTO if the PTO is in the Pending Test Order queue for a predetermined time (called max PTO time), for example more than one week or for more than two weeks.

These bi-directional LIS capabilities improve PTO-to-detection report turnaround time, reduce labor costs and eliminate potential transcription errors. The PTO-to-detection report turnaround time is preferably 0.5-6 hours, preferably 0.5-5 hours, preferably 0.5-4 hours, preferably 0.5-3 hours, preferably 0.5-2 hours, preferably 0.5-1 hour.

Figure 14:
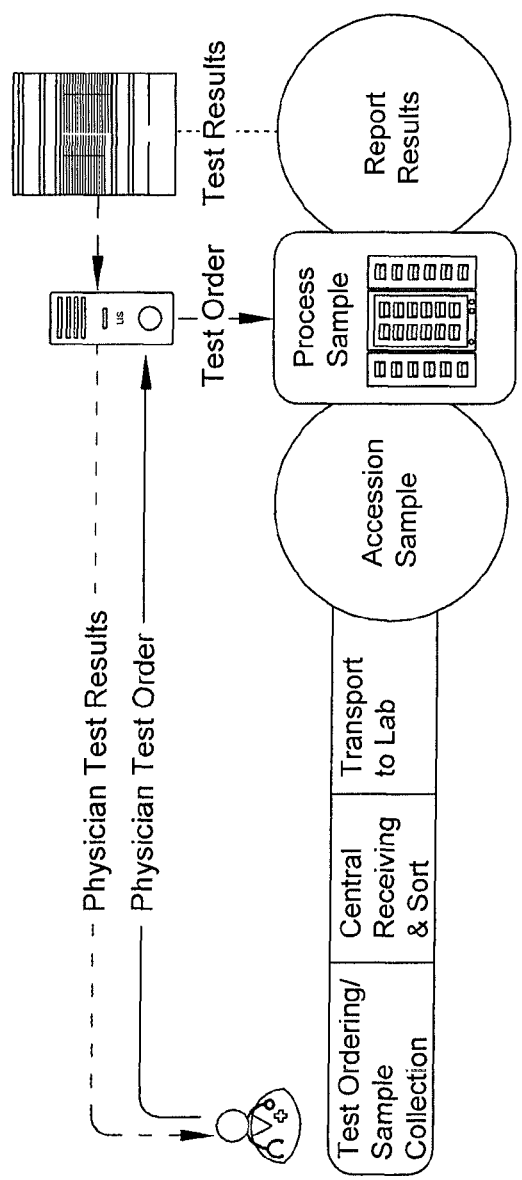
FIG. 14 Shows a schematic of the bi-directional LIS reporting.

The communication from the LIS interchange to the detection device's CPU may be referred to as the clinical instrument test order. FIG. 14: Shows a schematic of the bi-directional LIS reporting.

Reporting Results

Detection Reports

After the sample is run in a detection system, the detection system generates a result. A result may be generated if the amplified target DNA/nucleic acid hybridizes to its complementary signal probe and capture probes. A skilled artisan recognizes that other detection systems can be used. Examples of suitable detection systems include systems that depend on detection of color, radioactivity, fluorescence, chemiluminescence or electrochemical signals. A CPU in the instrument's base station (i.e., not a separate computer processor) then causes (either automatically or manually) a detection report (also referred to as a result report or test results) to be sent to the LIS interchange, which converts the detection report into a physician test result report and sends the physician test result report to the hospital's LIS, which then sends the physician result report to the physician, or directly to the physician. The detection report and/or the physician test result, which is sent to the hospital's LIS or to the physician, may include detected targets, non-detected targets, invalid results, and/or control data. In some examples, the sample-to-answer system may either auto release all information or hold all information for manual release. Alternatively, the sample-to-answer system may auto release some detection reports and hold some detection reports for manual release. For example, detected and non-detected targets may be auto-released, while invalids may be manually released (in other words, released only after a lab supervisor approves for release). If the detection report shows three (triple infection) or fewer targets were identified/detected, the detection report may automatically release to the hospital's LIS/physician. If the detection report shows greater than three (in other words four or more) targets that were identified/detected the report will be flagged, a multiple infection error alert (also called an alert notification) may be sent to the operator or physician and the sample may be automatically re-run. The detection report includes the assay ordered. If a cartridge is inserted that does not match the assay ordered (e.g. a gram-negative assay is ordered, but a respiratory assay is inserted) a "mismatch alert" may be sent to the operator and/or physician and/or the additional target is noted in the detection report. Anomalous results that are not auto-released may require a manager signature before manual release. Such reporting may minimize the risk of reporting errors.

The detection report may include time stamps such as sample collection time, sample ordering time, transport to central receiving lime, central receiving sort lime, transport to lab time, accession of sample time, time to process, and time to detection. The clock time stamps are commonly documented in hospital and laboratory information systems.

The automated result reporting (at order entry and results reporting) eliminates transcription errors and ensures actionable results are returned to physicians as soon as possible. Sample results are reported in about 60-90 minutes after the start of running the sample, this is referred to as time to result or sample to result. Preferably, sample results may be reported in about 60 minutes after the start of running the sample. Preferably, sample results may be reported in under 90 minutes after the start of running the sample. Preferably, sample results are reported upon test completion. A detection report may be sent immediately after the pathogen is identified by the detection system.

The sample-to-answer system may allow the operator to manually include comments in the detection report called detection report comments, e.g., to specify if the assay ordered matched the target(s) detected, the assay ordered does not match the target(s) detected, an additional target was detected in addition to the target for the assay ordered, a second assay is recommended.

The sample-to-answer system may compare the detected result with user created rules and apply a templated comment(s) to the detection report. The templated comments are based on a decision support generator having user-activated rules of selectable scope and selectable outcomes (i.e. approval, warning or stop outcomes). The outcome of a rule indicates how the templated comment is to be handled if the condition for including the templated comment is satisfied (i.e., approve the templated comment, send a warning templated comment or send a rejection templated comment).

Rules Report

If the detection report is sent separately to the LIS or clinician, a second rule report (also called a decision support report) may be provided (also referred to as a decision support report). The rule report includes one or more templated comments, for example, decision support that assists clinicians to interpret and/or act on results. The rule report may be provided in the same document as the detection report.

If the detection result and decision support report are sent separately, then the integrated diagnostic instrument 102 must associate the accession ID with the decision support report. Typically, when the Test data comes to the ISW from the AAM, it associates the accession ID with the test result. The Decision support generator will associate the accession ID with the templated comment during step 580 (process test result). This association can take place by printing the templated comment on a test report having the same accession ID or by printing the templated comment and accession ID on a decision support report. The Hospital LIS will associate the accession ID with the patient ID.

In some cases, the templated comment is not associated with the accession ID. For example, if the hospital wants to know how many times a particular drug was recommended for use an audit report could be run on that drug name in templated comments and a report generated without accession ID information.

Control Reports

Control reports or Control summary reports are generated based on the assay, test frequency, and lot of cartridges from the supplier. Control reports provide information about the number of samples run, and when control runs are needed. When a control run is processed, the report shows the expected and actual result, if the control passed or failed. Control runs are typically run every 30 days or every lot change. The sample-to-answer system alerts may be sent to the operator, for example, 48 and/or 24 hours before a control run is needed.

System Usage Report

The system usage report provides analytics around system usage data and performance based on a specified date range. For example, the system usage report may show if higher or lower than average samples were run, if higher or lower than expected samples were run, if a bay has not been utilized, etc. System Usage Reports may be printed from the Clinical Instrument or remotely by the clinical instrument's provider.

Service Notification Report

A service notification report is a report sent to the clinical instrument's provider to request remote access to the clinical instrument in order to trouble shoot errors, such as when a device has exceeded downtime for a month, exceeded invalid runs, mean time to failure is too high, no LIS connectivity, etc.

Alerts

The sample-to-answer system may also provide automatic alerts.

A Remote Practitioner Alert is an alert sent to practitioners to notify them that test results are available.

A Non-Operator Alert is an alert sent to non-operators such as lab managers, directors of labs, etc. regarding test results.

A Reportable Organism Alert is an alert sent based on a user-defined reportable organism. For example, if a patient is diagnosed with an infectious disease, then an alert may be sent to the Department of Health.

A Turnaround Time Violation Alert is an alert sent to the physician, operator or lab manager when the predetermined turnaround time is violated.

A Sample Stability Time Violation Alert is an alert sent to the physician, operator or lab manager that the sample stability time was violated.

A Duplicate Accession ID Alert is an alert notifying the operator that a sample with the same accession number was already run. Since each sample should have its own accession number, the operator should review for a possible error.

A Multiple Infection Error Alert is an alert to notify the operator that there are 4 or more co-infections detected and the sample should be re-run.

A Mismatch Alert is an alert sent to the operator or physician that a target is detected which does not match the assay ordered (e.g. a gram-negative assay is ordered but a fungal infection is identified).

A Pending Test Order Mismatch Alert is an onscreen alert (can also be sent to the operator via email) that displays when the cartridge inserted does not match the test order received from the LIS for the associated accession ID. For example, if the assay ordered was the BCID-GP assay, but a BCID-FP cartridge was inserted, the software will alert the user to either abort the run and re-run on the BCID-GP cartridge, or proceed with the BCID-FP cartridge inserted.

User Interface

The detection system may include a user interface comprising a touch screen display having a plurality of bay icons, each icon uniquely corresponding to one of a plurality of sample processing bays within an instrument. The user interface may further include an hour, minute and second countdown timer on the bay icon to show the time left until a result will be reported.

Additionally, the user interface may display the bay status (whether the bay is empty, the presence or absence of a cartridge, whether the cartridge assay is underway, assay complete, and a process error) even while the user is logged out.

In some examples, the user interface may include a virtual keyboard. The user interface may cause audible clicks by default when a user selects elements on a virtual keyboard.

The user interface may provide batch printing of reports.

QC Results

In many scenarios, monitoring and reporting quality control is both a requirement and a best practice to ensure the accuracy of patient testing results and compliance with lab standards. With on-board QC tracking capabilities, the sample-to-answer system provides safeguards to ensure labs not only run controls when required but enables labs to easily track and report compliance. Indeed, the processor in the base station may retain onboard QC test records to help ensure the lab runs controls when required. As discussed above, control reports may be sent if an external control is due in 48 hours and/or 24 hours.

The sample-to-answer system may prevent new runs if the detection system has not been qualified. This means that if a new lot is provided and a control should be run on the clinical instrument before running a patient sample, the instrument will prevent a patient sample test until the control is run.

The Sample-to-answer system further supports the release of QC results to the hospital LIS either automatically or manually.

Further, patient data may be automatically removed in all exported run data (troubleshooting logs and raw data calculations such as nA signal from targets, non-detected targets, controls etc) for HIPPA compliance.

The sample-to-answer system tracks and reports required preventative maintenance. Such systems may maximize lab efficiency in some instances by reducing administrative overhead.

Compliance and Data Management

The sample-to-answer system may provide the following compliance and data management tools: integrated data analytics to easily monitor lab performance; on-demand epidemiology reports for export and simplified analysis in Excel (including disease prevalence in a geographic area); and fully configurable, auto-release of test results (detected targets as well as non-detected targets). All of these unique capabilities of the sample-to-answer system allow Lab Directors to reduce their time spent on routine administrative tasks and focus their limited resources on high-value activities that impact patient care and the bottom line.

Specifically, on demand Epidemiology reports may be run from each base station individually or collectively from all the base stations run in the laboratory via the LIS.

Remote Service Capability

The sample-to-answer system includes remote service capability to minimize system downtime and ensure patients and physicians have access to rapid test results. Remote service may be needed when the clinical instrument has exceeded downtime for a month, exceeded invalid runs, mean time to failure is too high, no LIS connectivity, etc.

Positive Patient ID

The sample-to-answer system's positive patient ID feature reduces the potential for patient sample mix-up. Positive patient ID is described in more detail in U.S. Pat. No. 9,500,663, which is herein incorporated in its entirety by reference. Specifically, two machine-readable information tags (or patient identification tags) are arranged on the cartridge and encoded with cartridge-identifying information, where the information encoded in the second tag corresponds to the information encoded in the first tag and is read by a device within the sample processing instrument.

After a first machine-readable information tag on the outside of the cartridge is scanned, the cartridge may be loaded into any bay at any time, this is referred to as "random access" or "random and continuous bay access" or "unassigned" or un-delegated" or un-allocated" or unspecified" and the like. Stated another way, the cartridge need not be loaded into a specified bay. In this way, loading errors are avoided. Once the cartridge is loaded, the bay's CPU reads a second machine-readable information tag and confirms it matches the first machine-readable information tag.

With the sample-to-answer system, labs and physicians may have confidence that they have the right patient, with the right test, and the right result every time.

Integrated Diagnostic Instrument

FIG. 1 is a schematic diagram of an example of a system 100 to aid clinicians in their treatment of a patient infected or possibly infected with a microorganism or the presence of a drug resistance gene. The example of the system 100 shown in FIG. 1 includes an integrated diagnostic instrument 102, a rules configuration interface 107, an LIS interchange 114, the instrument 100 is connected to an LIS host (also referred to as a hospital LIS) 108, and an end client 112.

Figure 8:
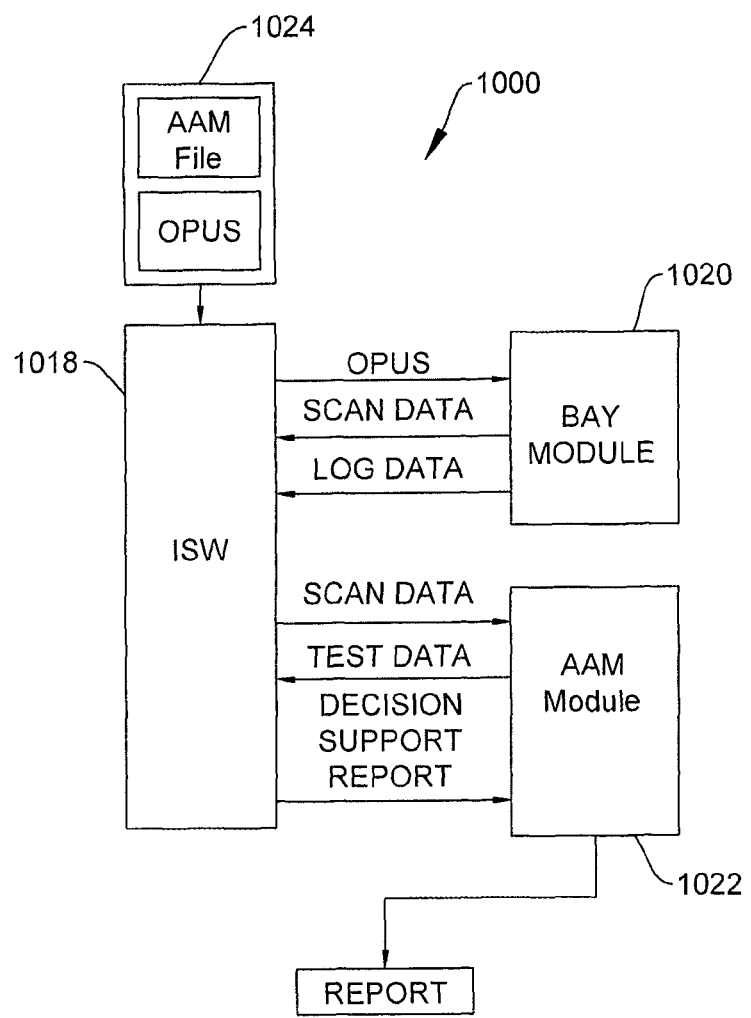
FIG. 8 is a schematic diagram of an example of an exemplary software architecture for a system to aid in providing decision support to a clinician to treat a patient infected or possibly infected with a microorganism.

The integrated diagnostic instrument 102 may include a pathogen detector 104 (which may include a bay module 1020 and assay analysis module (AAM) 1022 from FIG. 8) and a decision support generator 140. The integrated diagnostic instrument 102 may further include multiple rule databases, 150-1, 150-2, and 150-3, be associated with an LIS interchange 114, a communications interface (116), a processor 118, and a space to store data/reports/alerts/117. The integrated diagnostic instrument 102 may have a memory 120 in which the pathogen detector 104, the decision support generator 140, and the rule database(s) 150 are included.

Figure 3:
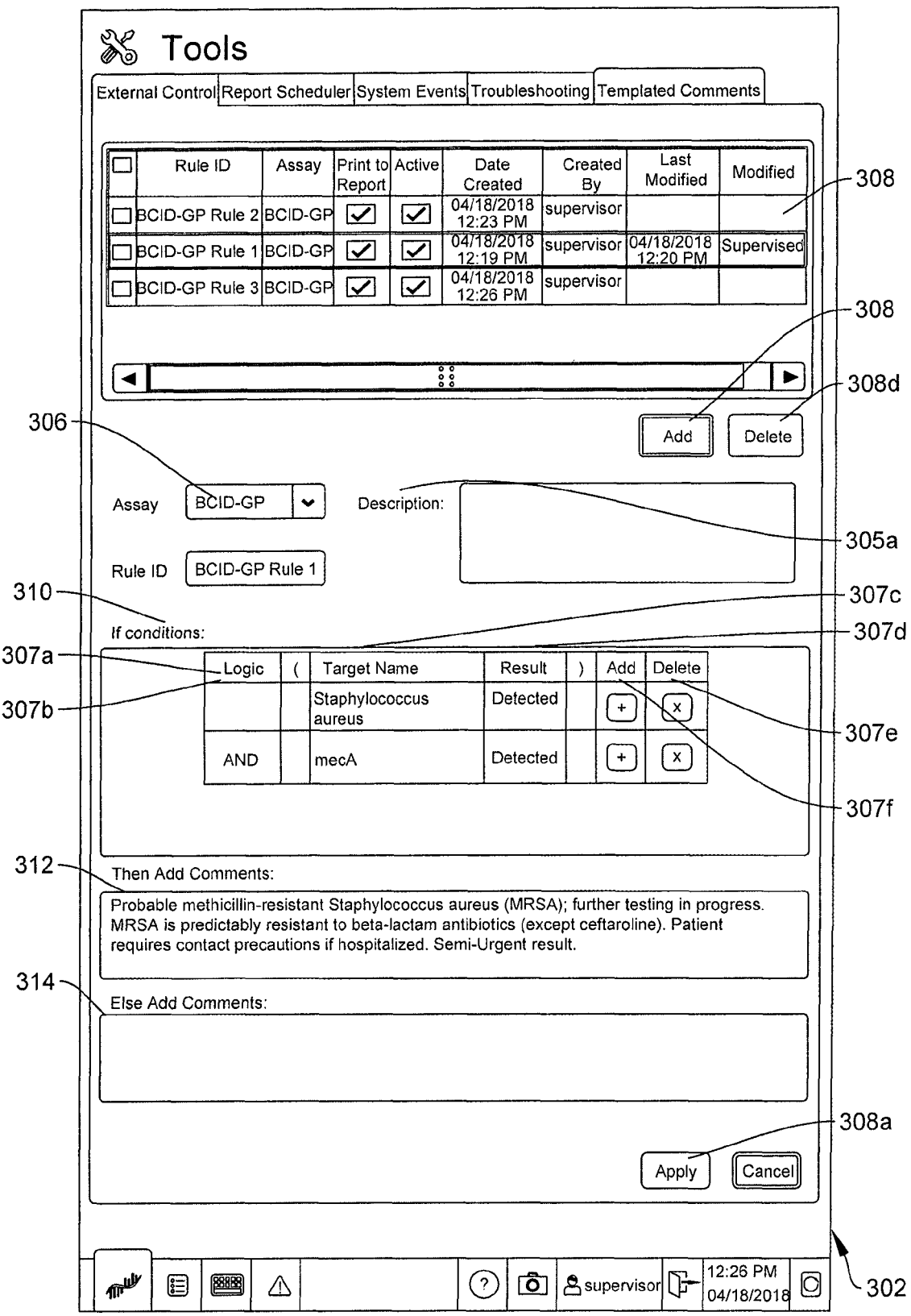
FIG. 3 illustrates an example of the templated comments configuration view.

Although the databases 150 are located inside of the integrated diagnostic instrument 102 in FIG. 1, in other examples, the integrated diagnostic instrument 102 may only include zero, one, or more of the databases 150. A person 110 may interact directly with the instrument 102 (by entering rules directly on a rules configuration interface 107 as shown in FIG. 3). Alternatively, a person 110 may interact in-directly with the instrument 102 via a remote rules configuration instrument 102r using a remote rules configuration interface 107r similar to that shown in FIG. 3).

The decision support generator 140 may be any component that may generate decision support information. The decision support generator 140 may service, for example, multiple hospitals (see FIG. 1b), each with their own diverse policies and treatment requirements. The decision support generator 140 may operate in a service bureau model to service multiple hospitals, antimicrobial stewardship oversight teams, and/or physician offices. Alternatively, the decision support generator 140 may be operated for the processing of orders within a single laboratory, hospital, antimicrobial stewardship over-sight team, and/or physician office.

The multiple databases, 150-1, 150-2, and 150-3, in this example, provide information utilized by the decision support generator 140 for providing templated comments. The databases 150 may include a Patient ID database 150-1 that includes patient identification such as age, gender, etc. The databases 150 may include a database 150-2 of user types. The databases 150 may include an assay type database 150-3 (data elements are used to pre-populate the databases). In some examples, this same information may be stored in a single database instead of in three databases.

When the instrument 102 produces a result, in other words, identifies a pathogen and/or resistance gene, the result may be forwarded to the decision support generator 140 for templated comments. The generation of templated comments is described in more detail hereinafter. Using information from the rule storage 700 or in a preferred embodiment the rules are stored on an instrument database 117, the decision support generator 140 may perform the actions described hereinafter to generate decision support information. One of those actions may be automatic completion of templated comments. If that is the case, the decision support generator forwards the templated comments to the LIS interchange 114 to be transmitted from the instrument 102 to the end client 112, which is described in more detail hereinafter.

Figure 1B:
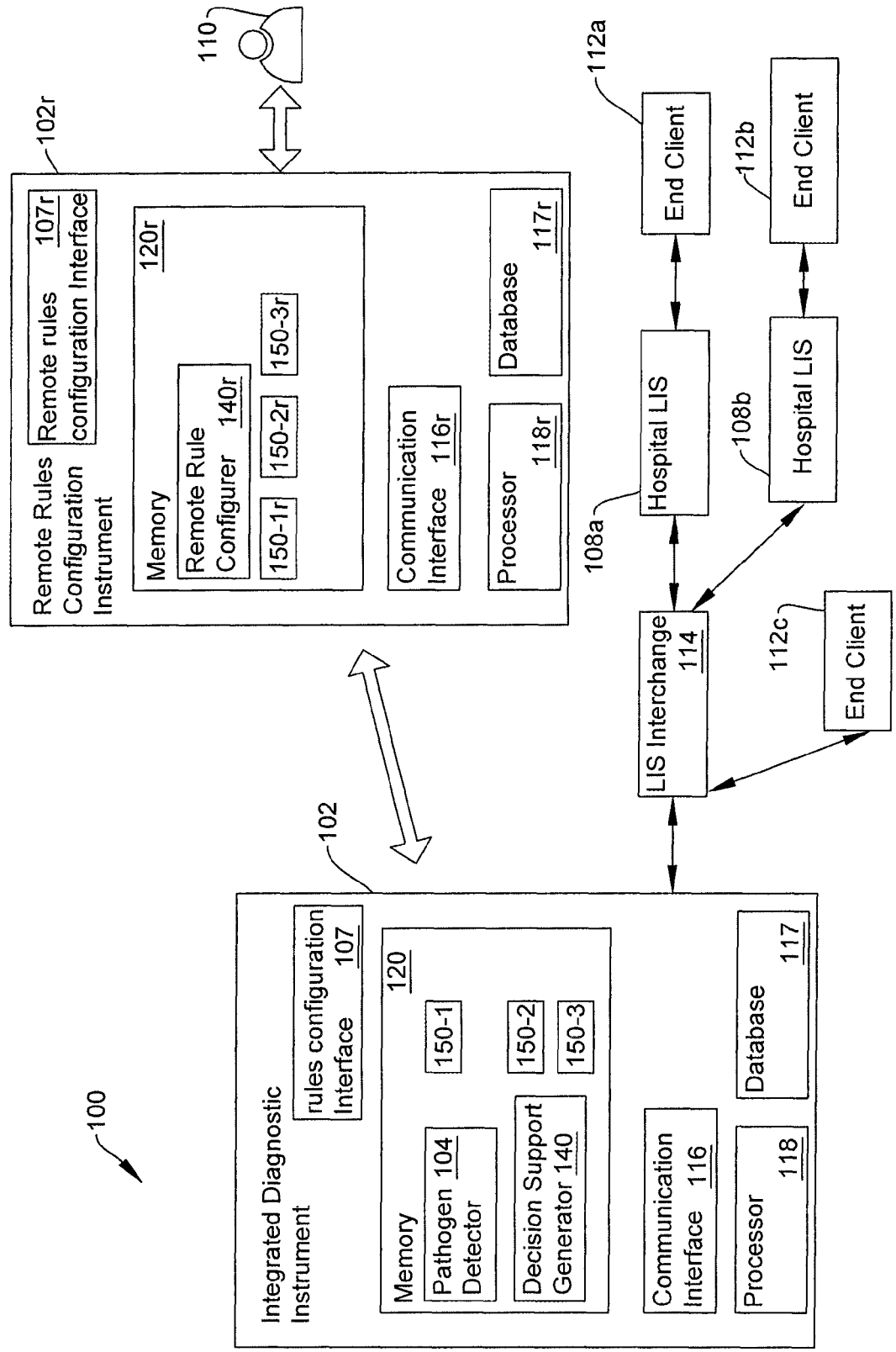

The end client 112 may be a hospital LIS, physician office computer, a cloud hosting service or any other computing device including a patient cell phone. The user 110, in some examples, may connect directly or indirectly to the integrated diagnostic instrument FIGS. 1*a-b*. For example, the user 110, such as a physician or system administrator, may be connected physically to the instrument 102 via, for example, the rules configuration interface 107 or may be remotely connected to the instrument 102 via, for example, the remote rules configuration instrument's 102*r* remote interface 107*r*. The remote connection can be, for example, an Ethernet cable. The connection between the instrument 102 and the remote rules configuration instrument 102*r* may be any collection of transmission links over which data between computing nodes may be exchanged. For example, the remote rules configuration instrument 102*r* may connect to the instrument 102 via a local area network (LAN), a wired network, a wireless network, a wireless local area network (WLAN), a WI-FI® network (WI-FI is a registered trademark of Wireless Ethernet Compatibility Alliance, Inc. of Austin, Tex.), a personal area network (PAN), a wide area network (WAN), the Internet, an Internet Protocol (IP) network, any other communications network, or any combination thereof. The remote rules configuration instrument 102*r* may communicate over the remote rules configuration interface 107*r* via the communications interface 116*r*. The instrument 102*r* may be in communication with the user over the communications interface 116*r*. The instrument 102 may be in communication with the end client 112 over the Lis Interchange 114 or communication interface 116. The LIS Interchange 114 or communication interface 116 may also include a local area network (LAN), a wired network, a wireless network, a wireless local area network (WLAN), a WI-FI® network (WI-FI is a registered trademark of Wireless Ethernet Compatibility Alliance, Inc. of Austin, Tex.), a personal area network (PAN), a wide area network (WAN), the Internet, an Internet Protocol (IP) network, any other communications network, or any combination thereof. The instrument 102 may be connected to one, two, three or more remote rules configuration instruments 102*r*. The instrument 102 may be directly connected to one, two, three or more hospital LISs. See 108*a* and 108*b* in FIGS. 1*b* and 1*c* The instrument 102 may be connected to one, two, three or more end clients. See 112*a*, 112*b*, and 112*c* in FIGS. 1*b* and 1*c*. As shown in FIGS. 1*a* and 1*b* the instrument 102 communicates with the hospital LIS and/or end client via the LIS interchange but it may also directly communicate with the hospital LIS or end client via the communication interface.

Figure 1C:
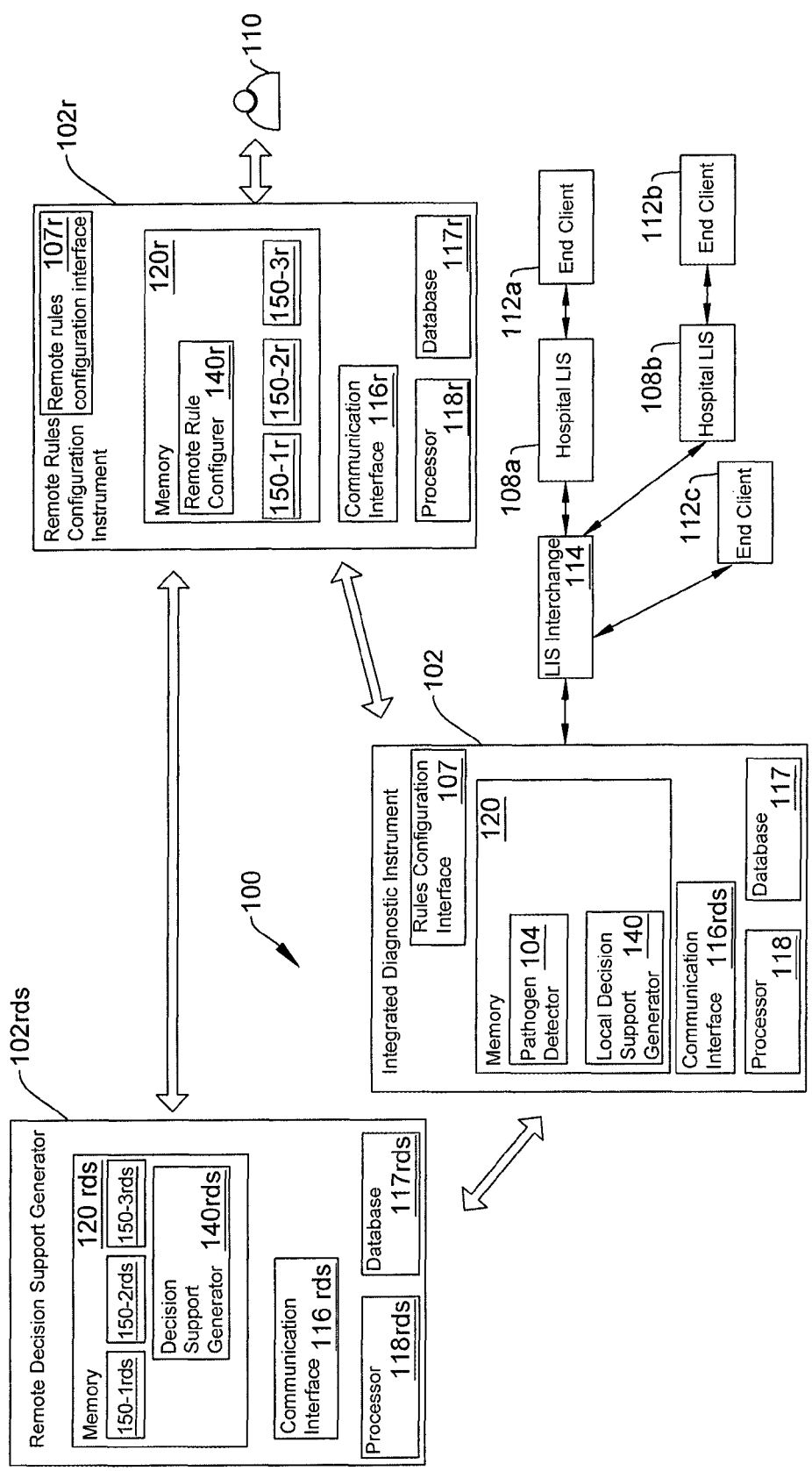

The instrument 102 may also be remotely connected to a decision support generator 102 See FIG. 1*c*. The remote decision support generator has a remote decision support generator 140, remote rule databases 150-1*r*, 150-2*r*, and 150-3*r* (see also FIG. 1*b*), a communications interface 116 a processor 118, and database 117. The remote decision support generator 140 has the features listed in FIG. 7 and are referred to with the same number. The connections on the remote decision support generator to the instrument and to the remote rules configuration instrument may also be a local area network (LAN), a wired network, a wireless network, a wireless local area network (WLAN), a WI-FI® network (WI-FI is a registered trademark of Wireless Ethernet Compatibility Alliance, Inc. of Austin, Tex.), a personal area network (PAN), a wide area network (WAN), the Internet, an Internet Protocol (IP) network, any other communications network, or any combination thereof. The rules established on a remote rules configuration instrument can be saved to a remote decision support generator and when the diagnostic instrument processes the result it connects to the remote decision support generator and process the result there and the templated comments, if any, are sent back to the diagnostic instrument and then reported to the end client. The remote decision support generator may be connected to more than one integrated diagnostic instrument. When the integrated diagnostic instrument connects with the remote decision support generator a check will be made 510 FIG. 5*a* to determine which rules are applied to that instrument/cartridge FIG. 5*d*. In addition to the checks identified in FIG. 5*d*, the check 510 may also evaluate the instrument requesting the decision support analysis to determine if any rules apply to that instrument.

The communications interface may be a network interface controller (NIC). The NIC may include hardware or a combination of hardware and software that enables communication over the communications network 106 and/or LIS interchange 114. The NIC may provide physical access to the network and provide a low-level addressing system through use of, for example, Media Access Control (MAC) addresses. The NIC may include a network card that is installed inside a computer or other device. Alternatively, or in addition, the NIC may include an embedded component as part of a circuit board, a computer mother board, a router, an expansion card, a printer interface, a USB (universal serial bus) device, or as part of any other hardware.

LIS Connectivity Architecture

The LIS connectivity architecture of the integrated diagnostic instrument may comprise the LIS Interchange (LI) 114 and Instrument Software (ISW), where the latter may include the pathogen detector 104, the decision support generator 140, and/or other components.

The ISW communicates with the LI; the LI supports both HL7 v2.3 and ASTM two-way communication with hospital LIS. The LI 114 may include two components: the LIS Interchange Manager (LIM) and the LIS Interchange Service (LIS) described in detail below but not shown in FIG. 1. Furthermore, the LI has the capability of importing and exporting text files to/from network folders without the need for LIS connectivity.

Instrument Software (ISW): The Instrument Software may provide high-level settings to enable the LIS communication and control the results to automatically release to the LIS interface. The LIS interchange may be enabled by a user with appropriate credentials (often a system administrator) via an LIS interchange tab of a graphical user interface displayed on the integrated diagnostic instrument 102. In some examples, in order for the integrated diagnostic instrument 102 to accept messages from the Hospital LIS, at least one assay must be checked as active under the Active column of the Assays tab in the Settings>Assays tab.

LIS interchange (LI): The LI 114 monitors low-level connectivity, and processes order and result data to convert them into acceptable messages within the guidelines of ASTM and HL7 messaging standards. These guidelines include actions to drive the instrument's behavior to test requests, laboratory workflow, and communicate final result data to the Hospital Laboratory Information System. The LI 114 controls the LIS interchange functionality for the instrument 102 by way of the following two components: (1) The LIS Interchange Manager (LIM): a Graphical User Interface for the LI to configure settings, monitor LIS interchange communication, perform system tests, and view transaction logs; and (2) The LIS Interchange Service (LIS): A Windows Service that runs in the background (invisible to the user) enables LIS communication between the instrument software and the LIS interchange 114. If this process is stopped or disabled in some examples, LIS communications will not be active.

LIS Workflow: The system may import test orders and export results in one of the following ways: Automatically using the ASTM interface to communicate with a connected LIS, such as the LIS Host 108; automatically using the HL7 v2.3 interface to communicate with a connected LIS such as the LIS Host 108; manually using flat files (CSV, TXT, XML) without the need for LIS connectivity; non-duplicate test orders may be displayed in the Pending Test Orders (PTO) screen.

The core function of LIS has traditionally been processing and reporting data related to individual patients in a clinical setting. Modern LIS offer an increasing amount of integration with laboratory instruments and applications. However, LIS may be hampered by its limited capacity for electronic data exchange. Indeed, LIS implementations are notorious for being inflexible and hard to adapt to new requirements. As a result, most modifications to hospital LIS systems comes in the form of middleware. Middleware provides modular solutions that are frequently not provided by the broader LISs or that are superior to the LIS alternatives.

However, middleware may—and often does—become a critical point of failure for some prior art implementations. Trying to prop up an old or poorly designed hospital LIS systems with middleware is error prone and may result in a fragile communication system. The solutions provided by middleware tend to extend the usable life, and continue the monthly maintenance fees, for the LIS vendor, thereby making operation of an LIS more expensive. Further, if the LIS uses middleware, a bidirectional connection is required to receive data from the instrument and then send and receive that information back to the middleware. A bidirectional connection generally costs twice that of a unidirectional link often cost-restrictive for smaller hospitals with smaller budgets.

Described herein is the integrated diagnostic instrument 102, which provides a modular solution not provided by the broader hospital LIS systems. The integrated diagnostic instrument 102 may be superior to some prior art solutions in that the integrated diagnostic instrument 102 eliminates the need for middleware and has its own bi-directional link with the hospital LIS. Having an integrated diagnostic instrument that avoids middleware helps decrease hospital dependency on a particular LIS provider or middleware provider and may reduce laboratory flexibility to switch instruments (because of non-compatibility with in-house middleware), which is regularly practiced in the diagnostics world.

Configurable Decision Support Generator

The basic design concept of the integrated diagnostic instrument 102 is that the integrated diagnostic instrument 102 is user configurable. In some examples, the integrated diagnostic instrument 102 includes the configurable decision support generator 140. The decision support generator 140 is configurable by an authorized user which will be discussed in more detail.

The system 100 may enhance quality of patient care through: more efficient assessment of result data and drug information from the medical device level, which will allow the laboratory to have a more streamlined/LEAN workflow; reduction of medical errors and the associated impact on quality of care and cost; increased communication between infectious disease clinicians and the laboratory; increased communication between infectious disease clinicians and the treating clinician; increased communication between antibiotic stewardship teams and the laboratory; and/or increased communication between antibiotic stewardship teams and the treating clinician.

Figure 16:
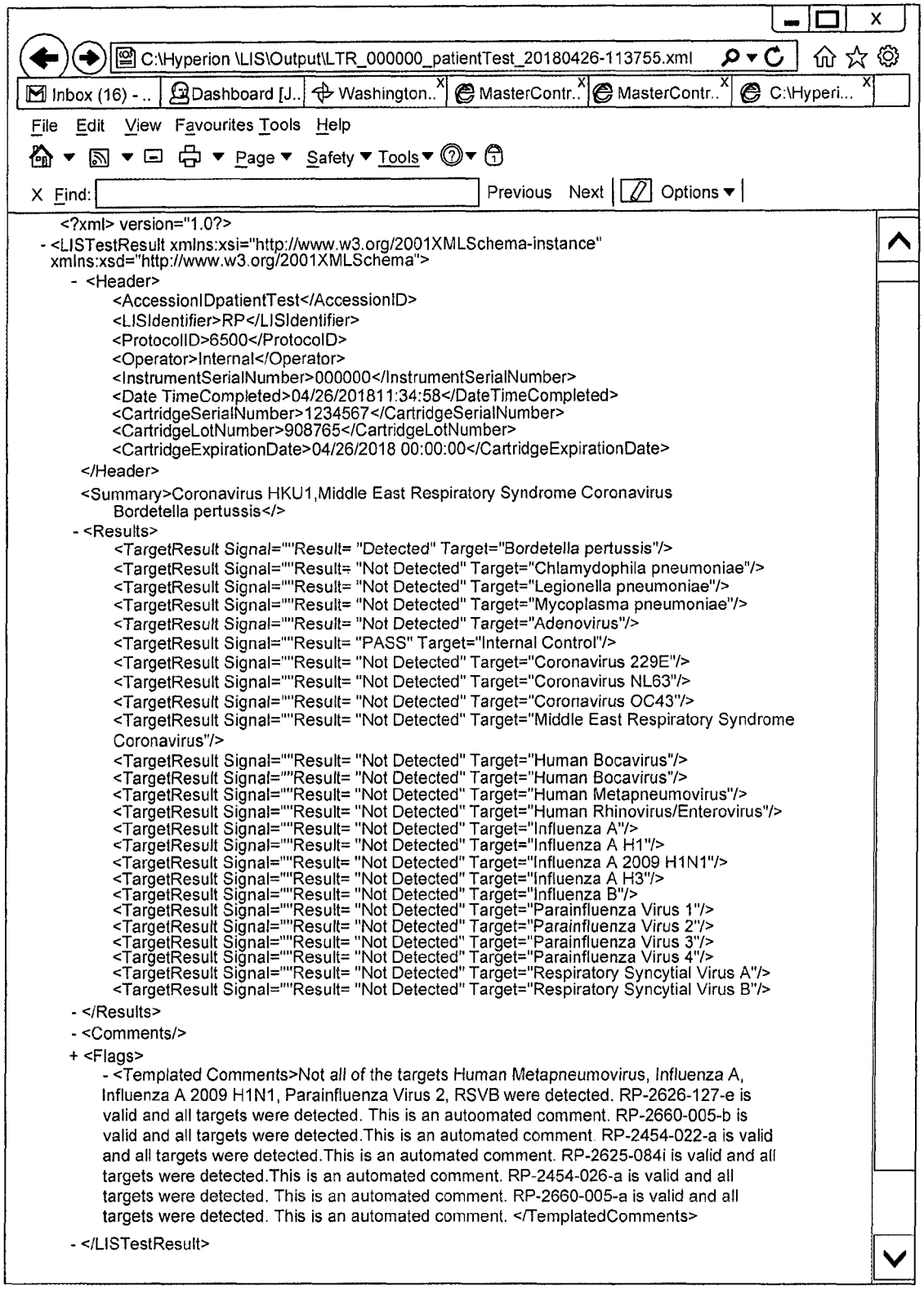
FIG. 16 is a sample xml file that is sent to a hospital LIS.

Templated comments allows the user to create "template rules" template rules specify conditions under which comments will be automatically added to Detection reports and sent to the hospital LIS. The user can specify the following fields for each template rule: Assay—the name of the assay to which this rule is applicable. Rule ID—a string identifier for the rule (should be unique). Description—an optional field where user can describe the rule. Logical condition (if conditions)—a logical statement that needs to be checked. It can consist of several statements combined using NONE, NOT, OR, XOR, exclusive OR, NOR, XNOR, NAND, XNOR operators (and combinations thereof). Statements can also be grouped using parentheses. THEN statement—the text of the comment that will be inserted for the tests that satisfy the logical condition (for which logical condition is true). Else statement—the text of the comment that will be inserted for the tests that do not satisfy the logical condition. This field is optional (can be empty). Active—specifies if the rule is active (inactive rules are not applied). Print to report—specifies if the comments specified by rule should be added to the detection report (when unchecked they are not added to the report, but are still sent to the hospital LIS). When there are several rules for specific assay and they all apply, all comments may be added to the report; each comment may start from the new line. All created template rules are saved in a rule storage 700 portion of the decision support generator or preferably in a instrument database 117 and can be viewed in a rule table 304. The result of the application of template rules: The xml file may be saved to Hyperion/LIS/Output folder, and contains the "Templated-Comments" node. See FIG. 16. The detection report displays all of the template comments in the "Comments" section. See FIG. 3 at 312.

Configurable by User Type

In some examples, the decision support generator 140 enables users with appropriate privileges to: define (create) a rule; edit a rule; enable a rule; disable a rule; and/or delete a rule. The term "user" refers to an account used by the person (or group of people such as an antibiotic stewardship committee, infectious disease committee or both) 110 after the person 110 is authenticated by, for example, entering a username and password.

In some cases, the rules on an instrument are applied to any cartridge (patient sample) processed by that instrument regardless of where that cartridge came from. In this way, templated comments will vary depending on the instrument the patient sample is processed in and the rules on that particular instrument.

In some cases, only particular rules on an instrument are applied to the cartridge (patient sample) processed by that instrument. In this way, templated comments will vary depending on cartridge information (such as physician origin, hospital origin, hospital network origin) but the rules must be defined on the instrument so the application of the rules still depends on the instrument the patient sample is processed in.

In some cases, the instrument is remotely connected to a decision support generator FIG. 1c and when a cartridge is loaded into an instrument, particular rules associated with that cartridge (such as physician origin, hospital origin, hospital network origin) are applied. In this way, templated comments will vary depending on cartridge information only and not the instrument the patient sample is processed in.

The decision support generator 140 has rules, which may be user configurable. The rules may be configured based on the user type (also referred to as a type of an "account", a type of a "user for a selected level", and a type of "end user"). For example, the user type may be a system administrator, a laboratory overseer, a hospital network overseer, a hospital overseer or user (such as a clinician, antimicrobial stewardship over-sight team, infectious disease team, pharmacist). In this way, system administrators, laboratory overseers, hospital network overseers, hospital overseers or users may each configure rules applicable to their own use independently of rules applicable to any other lab network, lab, hospital network, hospital, antimicrobial stewardship over-sight team, infectious disease team or physician office serviced by the decision support generator. Typically, the system administrator will have total access to all rules available the decision support generator 140. Typically, the user will have limited access to the decision support generator system. When a cartridge is loaded into an instrument it may read a machine-readable information tag (or cartridge origin tag) that includes information about the origin of the cartridge and which "user type" rules to apply when running the decision support generator. In some embodiments, the cartridge origin is part of the PTO and the PTO includes information about the origin of the cartridge and which "user type" rules to apply (510) when running the decision support generator for the sample. In either case, when the cartridge is loaded, the instrument may be configured to remotely connect to a remote decision support generator (not on the instrument, FIG. 1*c*) and populate the local decision support generator 140 (on the instrument) with "user type" rules. Alternatively, when the cartridge is loaded, the instrument may be configured to remotely connect to a remote decision support generator (not on the instrument, FIG. 1*c*) and send the remote decision support generator the test results and PTO data elements to the remote decision support generator and the results may be processed by the remote decision support generator and templated comments sent back to the integrated diagnostic instrument. Alternatively, the decision support generator 140 on the instrument may have rules from many different "user types" stored therein and when the cartridge is loaded, a check is made (step 510) by the decision support generator (140) to determine which rules are to be analyzed. For Example, in FIG. 5*d* system administrator rules may be applied (Y) but network level rules not applied (N). The system may be set up by the user(s) so that user type rules may be applied in conjunction with system administrator rules. In this way, some rules are universally considered for each cartridge while some rules are more narrowly applied.

An instrument provider (aka company that provided the instrument) may be able to create, edit, enable, disable, and/or delete all the rules for the instrument 102. In this way, the instrument provider initially may dictate which rules are applied for that instrument 102 regardless of the individual hospital network, hospital or user that requested the assay.

A system administrator (which could be for example, a laboratory network administrator or a supervising pharmacist or an authorized antibiotic stewardship committee member) may be able to create, edit, enable, disable, and/or delete all the rules from multiple laboratories where each laboratory is capable of reporting results to multiple hospital networks. In this way, the system administrator may dictate which rules are applied from that laboratory network regardless of the individual laboratory performing the assay or the hospital network, hospital, or user that requested the assay. In this way, system administrator rules may be applied to all test results produced by the instrument. In some cases, a system administrator establishes the rule remotely and applies the rules to all instruments in a particular laboratory in which they have authority to establish rules. In this way, every instrument in the laboratory or in the laboratory network has the same system administrator rules.

A laboratory overseer may be able to create, edit, enable, disable, and/or delete all the rules from a particular laboratory, where the laboratory is capable of reporting results to a plurality of different hospital networks. Accordingly, the laboratory overseer may dictate which rules are applied from that laboratory regardless of the laboratory network it is a part of or the hospital network, hospital or user that requested the assay. In this way, laboratory overseer rules may be applied to all test results produced by the instrument in a particular lab but not the laboratory network. In some cases, a laboratory overseer establishes the rule remotely and applies the rules to all instruments in a particular laboratory in which they have authority to establish rules. In this way, every instrument in the laboratory (but not in the laboratory network) has the same system administrator rules.

A hospital network overseer may be able to create, edit, enable, disable, and/or delete all the rules from a plurality of laboratories where the laboratories report results to the hospital networks. Accordingly, the hospital network overseer may dictate which rules are applied from any laboratory using the integrated diagnostic instrument regardless of the individual laboratory performing the assay or the hospital network, hospital, or user that requested the assay. In this way, the hospital network overseer rules may be applied to all cartridges coining from the hospital network (i.e. the cartridges have a tag which signals to the instrument, as discussed above, that the cartridges come from a particular hospital network). In some cases, a hospital network overseer establishes the rule remotely and applies the rules to all instruments in a particular laboratory in which they have authority to establish rules. In this way, every instrument in the laboratory or in the laboratory network has the same hospital network overseer.

A hospital overseer may be able to create, edit, enable, disable, and/or delete all the rules from a plurality of laboratories wherein the laboratories report results to that hospital. In this way, the hospital overseer may dictate which rules are applied from any laboratory using the integrated diagnostic instrument regardless of the individual laboratory performing the assay or the hospital network, hospital, or user that requested the assay. In this way, hospital overseer rules may be applied to cartridges coming from the hospital (i.e. the cartridges have a tag which signals to the instrument, as discussed above, that the cartridges come from a particular hospital). In some cases, a hospital overseer establishes the rule remotely and applies the rules to all instruments in a particular laboratory in which they have authority to establish rules. In this way, every instrument in the laboratory has the same hospital overseer rules.

A user may be able to create, edit, enable, disable, and/or delete all the rules from multiple laboratories wherein the laboratories report results to that user. In this way, the user may dictate which rules are applied from any laboratory using the integrated diagnostic instrument regardless of the individual laboratory performing the assay or the hospital network, hospital, or user that requested the assay. In this way, user rules may be applied to cartridges coming from the user (i.e. the cartridges have a tag or PTO which signals to the instrument, as discussed above, that the cartridges come from a particular physician). In some cases, a user establishes the rule remotely and applies the rules to all instruments in a particular laboratory in which they have authority to establish rules. In this way, every instrument in the laboratory has the same user rules.

In this way, the rules are based on a user selectable scope of application, in other words, the user may select the scope of application of a particular rule.

In some cases, the data element is a list of user names. If a particular user name is selected then all of the rules associated with that user are automatically populated in the Rules Table and processed by the Decision support Generator. More than one user name can be selected.

Configurable by Rule Type

The rules may also be configured depending on the rule type. In other words, the rules may have selectable parameters. For example, there may be laboratory network rules, laboratory rules, hospital network rules, hospital rules or user (aka clinician) rules. In some examples, rule types may only be created, changed or deleted if the user has the log-in credentials sufficient to change that rule.

Laboratory network rules may only be created, edited, or deleted by a system administrator (aka laboratory network administrator). In this way, the Laboratory network rules is the same for all results and/or templated comments reported from all of the laboratories within a particular network regardless of the individual laboratory performing the assay or the hospital network, hospital, or user that requested the assay.

A laboratory rule may only be created, edited, or deleted by a laboratory overseer. Accordingly, the laboratory rule is the same for all results and/or templated comments reported from that laboratory regardless of the laboratory network it is a part of or the hospital network, hospital or user that requested the assay.

A hospital network rule may only be created, edited or deleted by a hospital network overseer. Accordingly, the hospital network rule is the same for all results and/or templated comments reported to that hospital network regardless of the individual laboratory performing the assay or the hospital or user that requested the assay.

A hospital rule may only be created, edited, or deleted by a hospital overseer. Accordingly, the hospital rule is the same for all results and/or templated comments reported to that hospital regardless of the individual laboratory performing the assay or the hospital network or user that requested the assay.

A user rule may only be created, edited, or deleted by a user. In this way, the user rule is the same for all results and/or templated comments reported to that user of the individual laboratory performing the assay or the hospital network or hospital that requested the assay.

Multilevel rules: There may also be multilevel rules for example, a laboratory authorization rule may be created, edited, or deleted by both a system administrator and/or a laboratory overseer. A hospital network authorization rule may be created, edited, or deleted by both a hospital overseer and/or a hospital network overseer. A user authorization rule may be created, edited, or deleted by a user, hospital overseer and/or a hospital network overseer. A simple rule may be created, edited, or deleted by a system administrator, a laboratory overseer, a hospital network overseer, a hospital overseer and/or a user.

Conflicting Rules. When a rule conflicts with another, the rule may be processed against the rule set applicable thereto in order of narrowing scope of the rules. That is, rules requiring the highest level of authority to create, edit, enable, disable, and/or delete are applied first in the case of a conflict. The level of authority going from highest to lowest may be as follows: system administrator, a laboratory overseer, a hospital network overseer, a hospital overseer, and then a user generally. Thus, in the case of a conflict, a rule created by a system administer may be applied before a rule created by a user. See FIG. 5*b* for a flow chart of an exemplary process for rule processing in accordance with one aspect of the invention. As shown in FIG. 5B, a detection result is received from the pathogen detector 104. A check is made to see if customized rule settings are in effect for the system administrator (515*a*). If they are (515*a*—Y) or if they are not (515*a*—N), the rules engine would check the network level rules to see if network level rules are satisfied (515*b*). Then it checks rules associated with the laboratory (515*c*)), rules for the hospital network (515*d*), rules from the particular hospital from which the sample originates (515*e*) and the ordering clinician rules (515*f*). Once all of the outcomes from all of the checks 515*a-f*) are determined, the rule outcomes are reviewed to determine the appropriate action to be taken (560). If the outcome is reject (560—reject), the templated comment is rejected and in some cases an appropriate rejection templated comment is applied. If the outcome is warning (560—warning), the templated comment is associated with the detection result and in some cases a warning templated comment is applied. In some cases a warning message is sent to the system administrator or clinician with the warning. If the outcome is approval (560—approval), the templated comment is associated with the detection result and sent to the clinician.

Alternatively, when a rule conflicts with another rule, the templated comments from both rules may be applied to the decision support report.

The Decision Support Generator may also have a rule reconciliation mechanism. In one embodiment, when a rule conflicts with another rule, neither rule is applied. Before one or both of the conflicting rules can be applied, manual approval of the rule may be required. Once the user reviews the conflicting rules, one rule may be deleted and the other implemented. Alternatively, approval by both rule makes may be needed before a conflicting rule is implemented. After a user enters a rule, a rule reconciler (115, not shown) automatically compares the new rule to the rules in the Rules Table/rule storage 117. When all of the IF statements in the new rule match a rule already in the Rules Table/rule storage 117, the rule reconciler sends the new rule to a rule management module 720 (and/or in some cases the database 117) for manual approval. In this way a conflicting rule is not automatically applied to the instrument. In some embodiments, both the creator of the new rule and the old rule must manually approve the new rule. In some embodiments, when a conflicting rule is held for manual approval, the old rule is still in effect and will be applied to assay results until the new rule is approved. In some embodiments, when a conflicting rule is held for manual approval, the old rule may not be applied to assay results until the new rule is approved. If a conflicting rule is approved the RULE ID from both the new and existing rules may be applied to the rule.

In one embodiment, as rules are entered by a user the rule reconciler (115, not shown) automatically compares the rule being created to the rules in the Rules Table/rule storage 117. When the IF statement from a rule in creation matches an IF statement in the Rules Table/rule storage 117, the THEN statement is automatically populated. For Example, when the IF statement is one condition for example IF *Enterococ-* cus, and it matches a rule in the Rules Table that has one condition ("IF *Enterococcus*"), the THEN statement is automatically populated as the rule is being created. The user could then edit the THEN statement or delete the rule. If the user added another IF condition to the one condition and it did not match a Rule in the Rule Table, the THEN statement would not auto-populate. In this scenario each IF statement is considered the end of the logic for comparison purposes until another IF statement is entered. This is referred to as a Live Rule Checking. Live Rule Checking means that as the rule is created it is automatically compared to rules in the Rules Table/rule storage 117 for that instrument. If a match is found, the THEN statement is populated. If the user enters another IF statement, the Rules Table is checked again and if a match is found the THEN statement is populated with the new THEN statement. Each IF statement is assumed to be the end of the Logic expression. In this way, conflicting rules are avoided. If the user has rules saved to a remote decision support database, the remote decision support rule database will be checked via Live Rule Checking.

Dual Authorization Rules: some rules require multiple signoffs before the rule is created, changed, or deleted. For example, sign-off from an antimicrobial stewardship team member or infectious disease specialists may be required before a Dual Authorization Rule may be created, changed, or deleted. Dual authorization may be required for any user type and/or any rule type. In these cases, a rule is created and is not applied until a dual authorization button (not shown) is selected by a user with appropriate authority. Similarly, if dual authorization is needed to change of delete a rule then a rule is not changed or deleted until a dual authorization button (not shown) is selected by a user with appropriate authority.

Special Application rules: The scope of a particular rule may be set to be applicable only to a particular account, to a particular hospital, laboratory, etc. The scope of a particular rule may be set to be only applicable for a certain time period (for example special templated comments during an outbreak). To accomplish this, the templated comments configuration view 304 can have a start date data element (not shown) and an end date data element (not shown). The User can select to delay the application of a new rule until a specified time or may select to end the application of a rule at a specified time.

Special Action rules: For a particular rule, the rule may be applied to all templated comments originating from any account, hospital, or laboratory (for example special templated comments during an outbreak).

Diagnostic rules: Rules may be analyzed differently depending on if the rule relates to a genus or species pathogen. Rules applicable to the genus level may be processed before rules applicable to the species level, type or gene. This is similar to the hierarchy shown in 5*b* but applied to the diagnostic result instead of the creator of the rule See FIG. 5*c*. For example, the decision support generator checks rules associated with a genus result are analyzed first to see if they are satisfied 515*c-a*. Then the decision support generator checks rules associated with a species result 515*c-b*, then the decision support generator checks for rules associated with resistance gene markers 515*c-c*, then the decision support generator checks for rules associated with pan-targets 515*c-d*. Once all of the outcomes from all of the checks are determined, the rule outcomes are reviewed to determine the appropriate action to be taken (560 in FIG. 5A). In some cases, if rules conflict the rule from the highest category is applied, i.e., genus rules are applied before species rules are applied before resistance gene markers are applied before pan-target rules. In some cases, if rules conflict the templated comments from both or all rules are applied. In some cases, if rules conflict the templated comments from none of the rules are applied. In some cases species rules are applied before genus rules.

It is convenient to group sets of rules into distinct categories. Examples of such categories include organism, drug of choice, antibiogram sensitivity, action plan, resistance marker detection, workflow, drug, and dosage.

Flagged Rules

The rules may also be configured depending on the pathogen identified by the diagnostic assay. For example, there may be red flag rule, yellow flag rule, or green flag rule. In some examples, pathogen rule types may only be created, changed, or deleted if the user attempting to create, change, or delete the rule has sufficient privileges to change that pathogen rule type.

A red flag rule may be flagged red because of the pathogen identified by the diagnostic result. A red flag rule may be flagged red because the pathogen identified by the diagnostic result is being monitored for an outbreak. A red flag rule may be flagged red because the pathogen identified requires consultation with infectious disease teams and/or antibiotic stewardship teams.

A yellow flag rule may be flagged yellow because of the pathogen identified by the diagnostic result. A yellow flag rule may be flagged yellow because the pathogen identified by the diagnostic result is being monitored for an outbreak. A yellow flag rule may be flagged yellow because the pathogen identified requires consultation with infectious disease teams and/or antibiotic stewardship teams.

A green flag rule may be flagged green because of the pathogen identified by the diagnostic result. A green flag rule may be flagged green because the pathogen identified by the diagnostic result has stopped being monitored for an outbreak. A green flag rule may be flagged green because the decision support information does not require additional consultation with infectious disease teams or antibiotic stewardship teams.

In such cases, when the red, yellow or green flag rules are being created, there is a flag drop down as part of the THEN statement (now shown). When a flag color is selected from the drop down, the flag color is printed in templated comments to signal to the clinician that there is a problem (red flag), all clear (green flag) or warning (yellow flag).

System Set Up

When the integrated diagnostic instrument 102 is newly established or first configured, a number of steps may occur.

Figure 2:
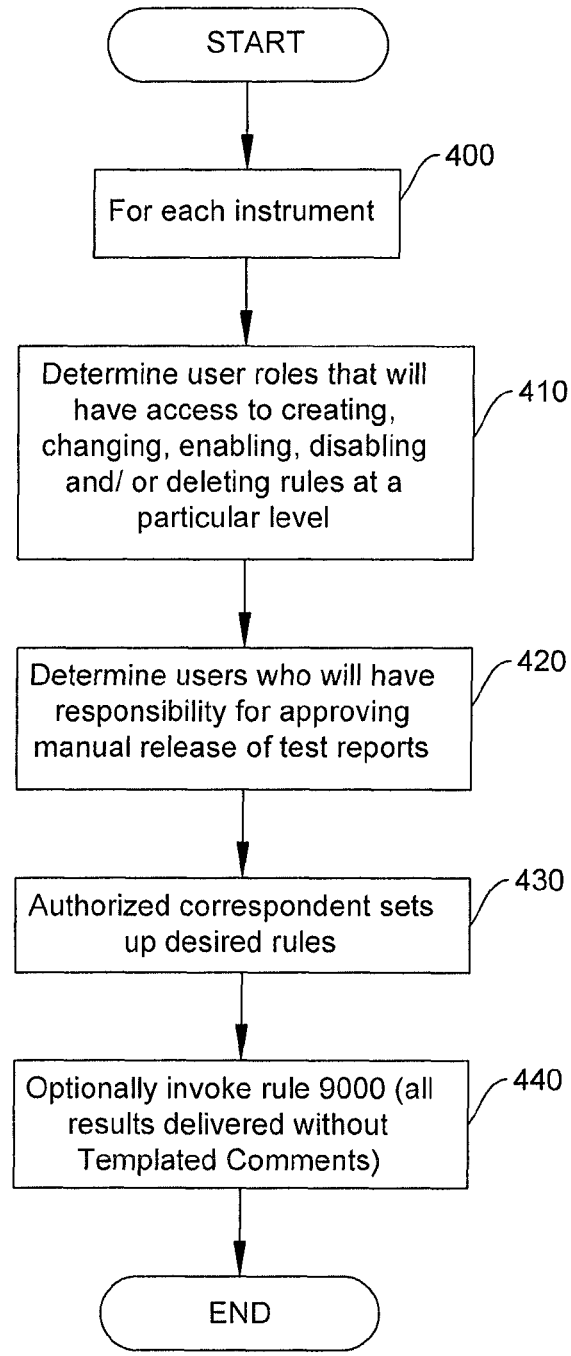
FIG. 2 is a flow chart of an example of a process for setting up the decision support generator.

FIG. 2 is a flow chart of an example of a process for setting up the decision support generator 140. For each laboratory and/or each instrument 102 (400), the system administrator may determine what user types or user roles (410) are to have access to the ability to create, edit, enable, disable, and/or delete rules. The system administrator determines what user types (420) are to have responsibility for manually approving test reports. A particular user type, authorized by the system administrator (by being given a user name and password not shown in the flow chart), sets up (430) desired user roles and/or rules for the lab/hospital/region/office. Optionally, one may invoke (440) a rule, such as "Rule 9000", for a predetermined period of time which directs all detection results and/or decision support information to an approval desk of an approver to ensure that the system and templated comments are operating as intended.

FIG. 2 shows that each instrument must be separately configured. Instruments can be configured either by a direct rules configuration interface or remote rules configuration interface. In a direct rules configuration interface the user logs in and directly establishes the rules on the instrument. In a remote rules configuration interface, the instruments may be remotely connected so that the same rules are set up on all instruments in the network (i.e. all instruments in a laboratory or all instruments servicing a hospital network). Rules can be sent from a central location (a computer) the central location comprising a remote rules configuration interface 107r and a remote rules storage database (such as 700r, not shown or in the remote rules configuration instrument's database 117r), and a processor 188r. The user would log into the remote rules configuration instrument and connect remotely to an instrument. If the user has the appropriate username and password, they can upload the stored rules on the remote rules storage database to the diagnostic instrument. Alternatively, if the user has the appropriate username and password, they can upload the stored rules on the remote rules storage database 117r, to the remote decision support generator storage 117rds.

Rule Interface

The decision support generator 140 may generate a graphical user interface that includes a templated comments configuration view 302, which may be viewed by navigating to, for example, Tools>Templated Comments. FIG. 3 illustrates an example of the templated comments configuration view 302. The templated comments view 302 may provide a Rules Table 304 with the following example elements: Checkbox, Rule ID, Name, Assay, Date Created, Active (checkbox), Created By, and/or Last Modified. The Rules Table 304 is a view of the rules stored in the rules storage database 117. The Rules Table 304 is a summary of the Rule IDs on the diagnostic instrument, i.e., the rules the decision support generator 140 may choose from. To Disable a Rule or Delete a rule the checkbox next to the rule is selected and the delete button 308d is selected. Generally, to Change a Rule, the checkbox next to the rule is selected, the rule changed as desired (either by changing the comments, logic, targets, result etc) and the apply button 308A is selected. In response to selection of the rule in the Rule Table (in other words, when the corresponding checkbox is enabled) the following buttons (not shown), for example, may be available to the user: Export As (CSV, PDF), Print, Edit, Enable, Disable, Delete, and/or Authorize. These actions are discussed in more detail below.

Creating a Rule

To add a rule, the ADD 308 button is selected. Next the user selects an Assay dropdown 306 that may be included on the templated comments view 302. When the Assay dropdown 306 is selected, buttons to select an assay may be displayed. Typically, only assays that are approved to be run on the diagnostic instrument are included in the Assay Dropdown 306. For example, if only RP panel is FDA approved then only the RP assay will appear in the dropdown. As the instrument is configured to run more assays the assay dropdown 306 will be updated via a remote software update. The assays that are selectable may include, for example, a Respiratory, Blood Culture Identification-Gram Positive, Blood Culture Identification-Gram Negative, Blood Culture Identification-Fungal, Gastrointestinal Pathogen Panel (GI), Central Nervous System, HCV Genotyping, Cystic Fibrosis Genotyping, Thrombophilia Risk, Warfarin Sensitivity and/or, 2C19 Genotyping. Details on how the decision support generator 140 operates to add a rule are discussed in more detail below.

The decision support generator 140 may generate a graphical user interface in response to selection of the Add Rule (also called the New Rule) button 308. The generated graphical user interface may include: Assay dropdown—allow the user to select the assay that the rule will be defined for; Rule ID—the decision support generator 140 may automatically generate the unique ID.

In some examples, the decision support generator 140 generates a unique code for a rule called a Rule ID 310. The code may include, in some examples, a prefix corresponding to the associated assay name, such as BCID or RP. Alternatively, or in addition, the code may include an assay name tag together with a four-digit number (or any other number of digits) incrementing from 0001. For example: BCID-0001 and RP-0001. Alternatively, the decision support generator 140 allows the user to define a Rule ID 310 for each rule. In this way the Rule ID is fully customizable.

In some examples, the decision support generator 140 enables the user to name individual rules. Alternatively, or in addition, the name is limited to 100 characters (including spaces) or some other predetermined number of characters. In some examples, the rule name must be unique across all assays.

In addition to the Rule ID 310, a description of the rule can be entered 305a. The rule description is fully customizable.

Implementation.

The following classes can be involved in creating a new rule: assay name, created by, creation time, description, else comment, last modified time, logical condition, modified by, operator, print to report, rule checked, rule ID, send to LIS, THEN comment etc. Classes can be added or deleted. Templated Rule class saves all information about a particular template rule to the Templated Rules table database.

Figure 17A:
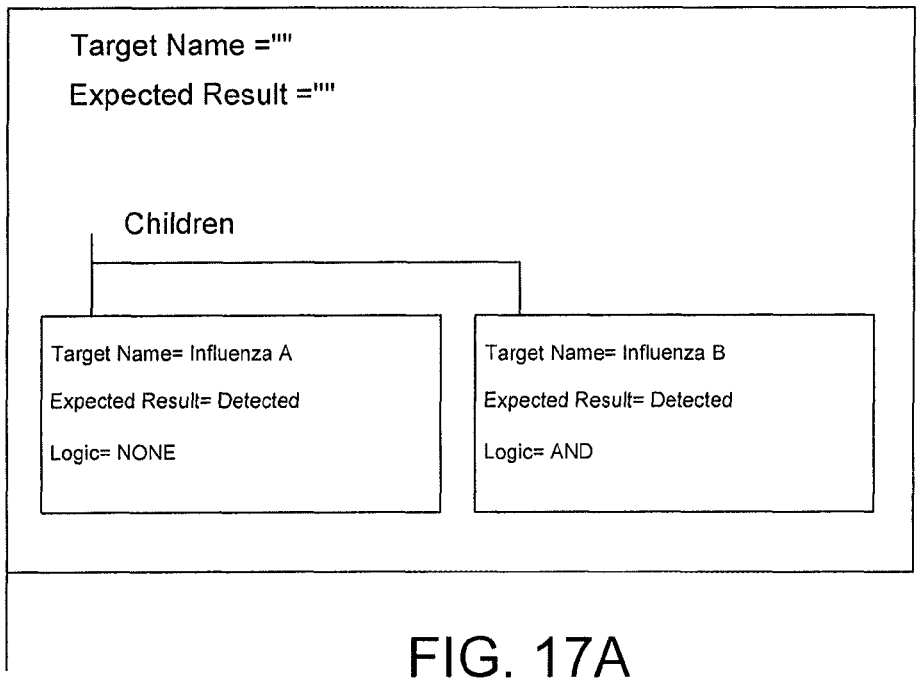
FIGS. 17*a-b* shows target logic conditions.
Figure 17B:
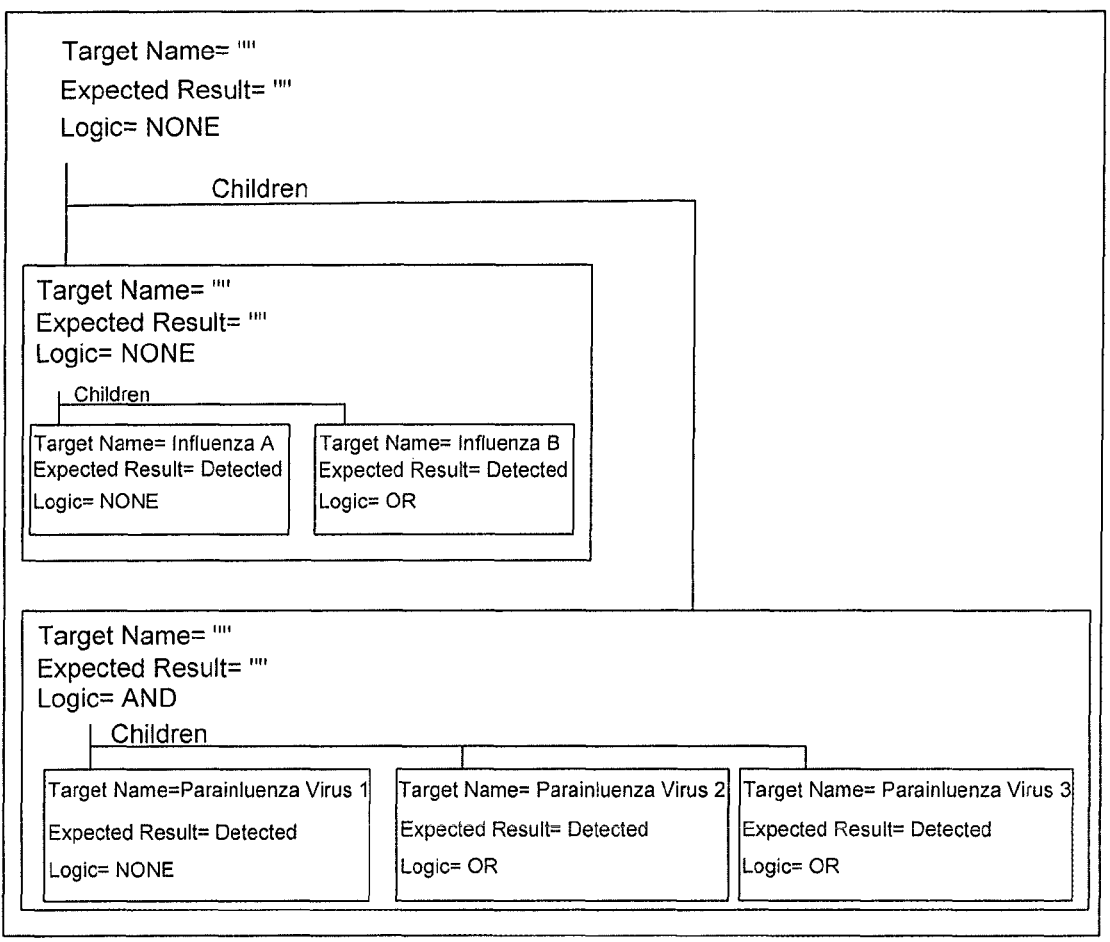

Templated Rule also has a member (logic): TargetResultLogicalCondition_logicalCondition that contains information about the logical condition for this rule; it can be a complex condition. When the Templated Rule is saved to the storage 117, _logicalCondition is serialized and saved to LogicalConditionXml string. Later, when the application starts and template rules are initialized, the string is read from the NexGen database and de-serialized to _logicalCondition member. When a Result is evaluated by templated comments it evaluates the assay target, children, expected ENUMResult, expected Result, ID, Logic. The evaluate method takes sample result and returns the Boolean indicating if the logical condition fulfills or not for this test. If the determination cannot be done it returns null. Logic is enumeration that can be NONE, NOT, AND, OR, XOR or combinations thereof. Children is a List<TargetResultLogicalCondition>. This way the logical condition can include other logical conditions. AssaycTargets is a list of targets of the assay for which this logical condition will be applied. TargetResultLogicalCondition can be a "simple" condition, for example like "*Candida albicans* Detected". In this case it has no children, TargetName="*Candida albicans*", ExpectedResult="Detected", Logic="NONE". The Evaluate( ) method will take SampleResult, find out if the TargetResult for *Candida albicans* is "Detected", and return true or false. TargetResultLogicalCondition can be also a "complex" condition, for example "Influenza A detected or Influenza B detected". In this case TargetName and ExpectedResult will be empty, but it will have 2 Children: child 1 (target name=influsenzaA, expectedresult=detected logic=none; child 2 target name=influsenzaB, expectedresult=detected logic=AND) see FIG. 17a. Each child will be evaluated separately and then the results will be combined using specified Logic operator (AND in the example above). There can be also more complicated rules, requiring use of parentheses, like (Influenza A Detected OR Influenza B Detected) AND (Parainfluenza Virus1 Detected OR Parainfluenza Virus 2 Detected OR Parainfluenza Virus 3 Detected). FIG. 17b illustrates the TargetResultLogicalCondition created for this example. Stated another way, when a rule is evaluated the first target associated with that rule is considered first and then any children (called rule children) associated with that first rule. If there is a second target associated with the rule, then the second assay target is considered second and then any rule children associated with that second rule.

The method of applying child logic can be understood as follows: A method comprising: specifying a rule logic, wherein said specifying the rule logic comprises selecting a first factor wherein the first factor comprises one or more child factors, and applying the first factor to obtain a first factor value, then applying the first child factor to obtain one or more child factor values, if a second child factor is present applying the second child factor to obtain a second child factor value. If the child factor has one or more grandchild factors the grandchild factor are applied before applying the second child factor. If the rule has a second factor all of the first factor values (including rules for children and grandchildren) are obtained before applying the second factor. Once all of the factors are evaluated they are analyzed to obtain a result which can be in the form of a THEN statement for templated comments. The rules logic is stored in a memory. Each rule factor corresponds to a data point, the factor value corresponds to the result obtained from applying the data point. In this way all parent logic must be implemented before any of its child logic in the top-to-bottom implementation methodology.

The TemplatedCommentsService (implementing ITemplatedCommentsService) initializes TemplatedRules from the database 117 when the application starts and maintains the cache of templated rules in the memory to reduce the number of database transactions and potential for deadlocks. The method List<string>GetTemplatedComments(Test test, bool forReport); returns the list of templated comments for the specified test after applying all template rules. The second argument (bool forReport) specifies if we are getting the list of comments to print to the detection report or to send to LIS (these lists can be different because some template rules can have PrintToReport property turned off). The void RefreshRules(string assayName); method refreshes the cache of the rules from the database. If the argument assayName specifies the name of the assay for which the rules should be refreshed. If the assayName is null or empty then all rules (for all assays) are refreshed.

The classes TemplatedCommentsView and TemplatedCommentsViewModel implement the user interface allowing the user to create, edit and delete template rules. The UI is described elsewhere. TemplatedCommentsViewModel is derived from Validating view model as it should perform the validity check of the changes to the rule entered by the user. TemplatedCommentsViewModel contains the ObservableCollection<TemplatedRule>TemplatedRules collection that serves as a source for the rules grid. When the user selects particular rule in the grid (rule table) (TemplatedRule SelectedRule), the editing controls for this rule become visible (through binding to IsModifying flag). The user may also create a new rule; IsEditingExistingRule flag allows to distinguish between creating a new rule and editing an existing one. The first choice the user does when creating a new rule is to select an assay (the combobox choices contain all currently active assays); after the assay is selected (Assay SelectedAssay), we update the TargetNames collection to provide correct target choices in the comboboxes for entering thelogical condition.

The collection ObservableCollection<RuleRow>RuleRows 304 provides the source for the rows of the "Conditions" grid. The RuleRow class has members to capture the user input for the row in the "condition" grid: ExpectedResult—Detected or Not Detected, Logic—NONE, AND or OR (or combinations thereof). LeftParenthesis, RightParenthesis are bools indicating if this row contains corresponding parentheses. ToLogicalString( ) returns string like the one you can see in the row (for example "AND *Rhodotorula* Not Detected)". GetLogicalCondition( ) returns the simple TargetResultLogicalCondition corresponding to the current row. When the user has entered the logical condition, we get the input from the RuleRows and the method of TemplatedCommentsViewModel TargetResultLogicalCondition GetLogicRule( ) parses the input to create the logical condition object. Another method, List<RuleRow>rulerowsFromCondition(TargetResultLogicalCondition cond) is used for the opposite task: it creates a collection of RuleRows to display the condition grid based on the saved TargetResultLogicalCondition. Both methods use recursion. The method string GetRuleValidationResult ( ) checks the entered rule for validity and if there is an error returns the error message (that is being displayed on the UI).

Changes to the Test class: the template rules are applied when the sample run is completed, and the template comments should not change when the user looks at the report later. Because of this requirement the template rules are applied when the run completes, get the list of comments for this test and save them in the NexGen database; the next time the user generates the report, the saved comments are read from the database and do not apply the rules, as they may have changed. To implement this, the new column has been added to the Tests table.

As template comments string to be printed on the report is different from template comments string to be sent to LIS. There were also changes to LisExporter (to add the TemplatedComments under the new node to the xml file) and to ResultsProcessingService (in the end of the sample run, the code requesting the list of template comments from the TemplatedCommentsService and saving it to the database has been added).

Writing the IF Statement

In some examples, the decision support generator 140 enables the user to begin writing an IF portion 310 of the rule by selecting a data element from a data element dropdown list (not shown) associated with the assay 306 selected. In some examples, the decision support generator 140 allows one IF statement per rule. Alternatively, or in addition, the decision support generator 140 allows two IF statements per rule. Alternatively, or in addition, the decision support generator 140 allows three or more IF statements per rule. Alternatively, or in addition, the decision support generator 140 allows 1-100 IF statements per rule or any other number of IF statements. Alternatively, or in addition, the decision support generator 140 enables the user to select the operator (logic) from an operator dropdown user interface control. The user may then add {AND}/{OR} operators if evaluating multiple conditions (discussed below). The user may then add {(}/{)} operators if evaluating multiple conditions (discussed below). A rule logic parameter (IF statement) is added to the Rule by hitting the ADD button 307*f*, a rule logic parameter (IF statement) is deleted from a Rule by hitting the DELETE button 307*e*.

In some examples, IF statements are formatted as follows: IF: Data Element 307*c* is *Result Type dropdown 307*d* (Detected/Not Detected)*. As one such example, a first IF statement shown in FIG. 3 has the data element set to "*Staphylococcus aureus*" and the Result Type set to "Detected". A second IF statement in FIG. 3 has the data element set to "mecA" and the Result Type set to "Detected". In this illustrated example, the condition for including a templated comment, which is designated in a "THEN statement" 312, is satisfied if both *Staphylococcus aureus* and mecA are detected in the patient sample. Alternatively, if the condition is not met, then a templated comment designated in an "ELSE statement" 314 may be included in the decision support information.

In this way, the "IF" statement is not fully customizable. The Users are only permitted to select from a select group of choices such as assay type, data element and result.

Creating a Rule: Applying Logic

When the assay is selected, target names are populated in a target name drop down. The target names correspond to the targets that are detected or capable of being detected by the assay (including resistance gene markers and pan targets). A target name is selected 307*c*. Then a result can be selected, either detected or not detected 307*d*. Then logic can be applied from a drop down, either "AND", "or" or "("(")". 307*a* and 307*b*.

The condition for including the templated comment may comprise a logic expression that evaluates to either true or false or an equivalent thereof, like "one" or "zero." If the logic expression evaluates to true, for example, when the corresponding decision support information (also called templated comment) option is applied to the detection results, then the decision support generator 140 includes the templated comment in the decision support information. Alternatively, if the logic expression evaluates to false, then the detection device does not include the templated comment in the decision support information. Alternatively, if the logic expression evaluates to false, for example, when the corresponding decision support information (also called templated comment) option is applied to the detection results, then the decision support generator 140 includes the "Else" templated comment in the templated comments.

Writing the THEN Statement

After the logic has been entered the user may include user-customizable text in the "Then" comment box.

In some examples, the decision support generator 140 enables the user to begin writing the THEN statement 312 of the rule by manually entering text into the "Then" section 312. In this way, the "then" statement is fully customizable. The user can enter treatment decision support information, the user can enter comments such as "consult with a pharmacist" and combinations thereof.

Alternatively, or in addition, the decision support generator 140 allows blank THEN statements 312.

Thus, an important aspect of the system is that the "IF" statement is not fully customizable, the user must select from a finite set of choices but the "THEN" statement is fully customizable. The IF statement data elements (target, result, logic) are not defined by the user, i.e., the user does not determine which data elements are available to choose from.

In some examples, the THEN statement can be converted into a "predefined THEN statement" i.e., not fully customizable. When a user writes a THEN statement that they want to establish as a predefined THEN statement the user highlights the THEN statement and then selects a "Predefine" button (not shown) on the templated comments configuration view. The THEN statement becomes a "Predefined THEN statement." The Predefined THEN statement will then be populated as a data element from a THEN statement data element dropdown button (not shown). In this way the instrument provides a way for the user to define the THEN statement data elements. Once THEN statement data elements are available, the user can select a THEN statement data element instead of manually writing the THEN statement.

Writing the ELSE Statement

In some examples, the decision support generator 140 enables the user to write an ELSE statement 314 of the rule. If the logic for the rule is not satisfied, then the ELSE statement is applied. In this way, the "ELSE" statement is fully customizable. The user can enter treatment decision support information, the user can enter comments such as "consult with a pharmacist and combinations thereof.

In some examples, the ELSE statement can be converted into a "predefined ELSE statement." When a user writes a ELSE statement that they want to establish as a predefined ELSE statement the user highlights the ELSE statement and then selects a "Predefine" button (not shown) on the templated comments configuration view. The ELSE statement becomes a "Predefined ELSE statement." The Predefined ELSE statement will then be populated as a data element from a ELSE statement data element dropdown button (not shown). In this way the instrument provides a way for the user to define the ELSE statement data elements. Once ELSE statement data elements are available, the user can select a ELSE statement data element instead of manually writing the ELSE statement.

Alternatively, or in addition, the decision support generator 140 allows blank ELSE statements 314. A blank ELSE statement 314 may indicate that there is no action to be taken when the IF condition 310 evaluates to false.

Thus, an important aspect of the system is that the "IF" statement is not fully customizable, the user must select from a finite set of choices but the "THEN" and "ELSE" statements are fully customizable.

The "IF" statements are collectively referred to as rule logic parameters. Logic parameters are predefined for the user, i.e. the user cannot create a logic parameter. The "IF, THEN, AND ELSE" statements are collectively referred to as rule parameters.

Figure 4:
FIG. 4 illustrates a second example of the templated comments configuration view.
Figure 10:
FIG. 10 illustrates a third example of the templated comment configuration view.

FIG. 4 illustrates an example of the templated comments configuration view 302 that shows a rule that is simpler than the rule shown in FIG. 3. FIG. 10 illustrates an example of the templated comment view 302 that shows a rule related to a pathogen that related to a disease other than sepsis.

In some examples, the rules are automatically applied as soon as they are entered and the apply button 308*a* pressed. In this way, the rule is applied in real-time. In other examples the rules must be authorized before they are applied by a user authorized to approve a rule.

Figure 5A:
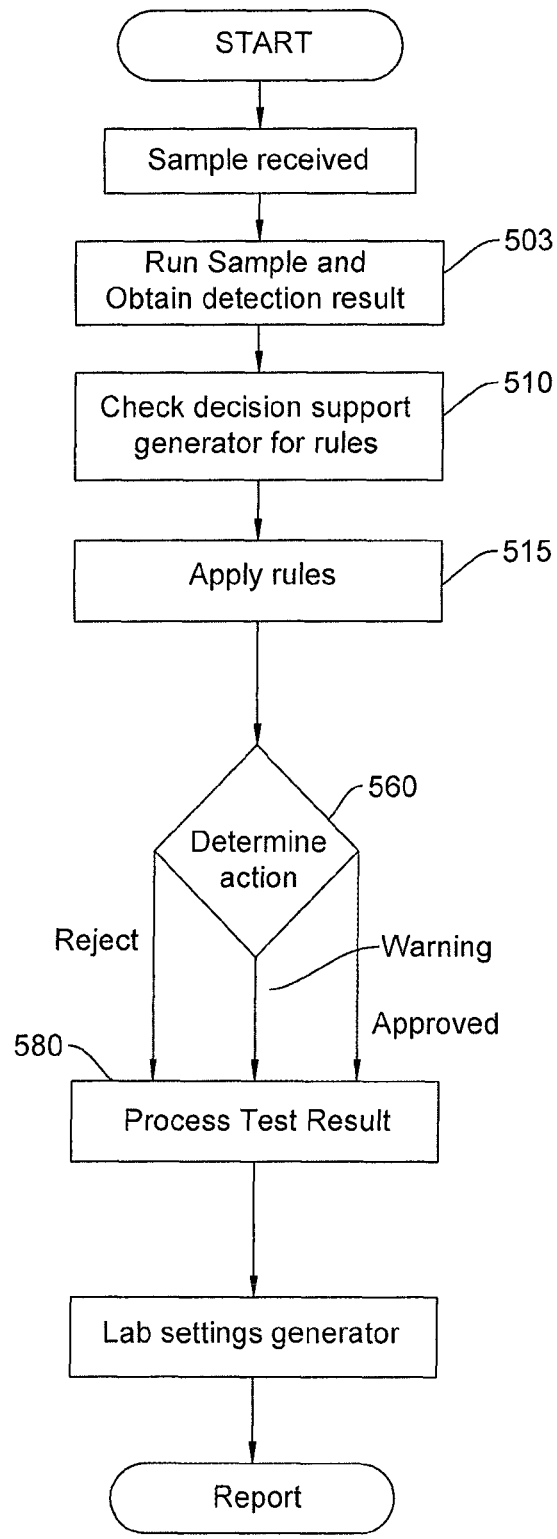
FIGS. 5*a-d*.
Figure 5B:
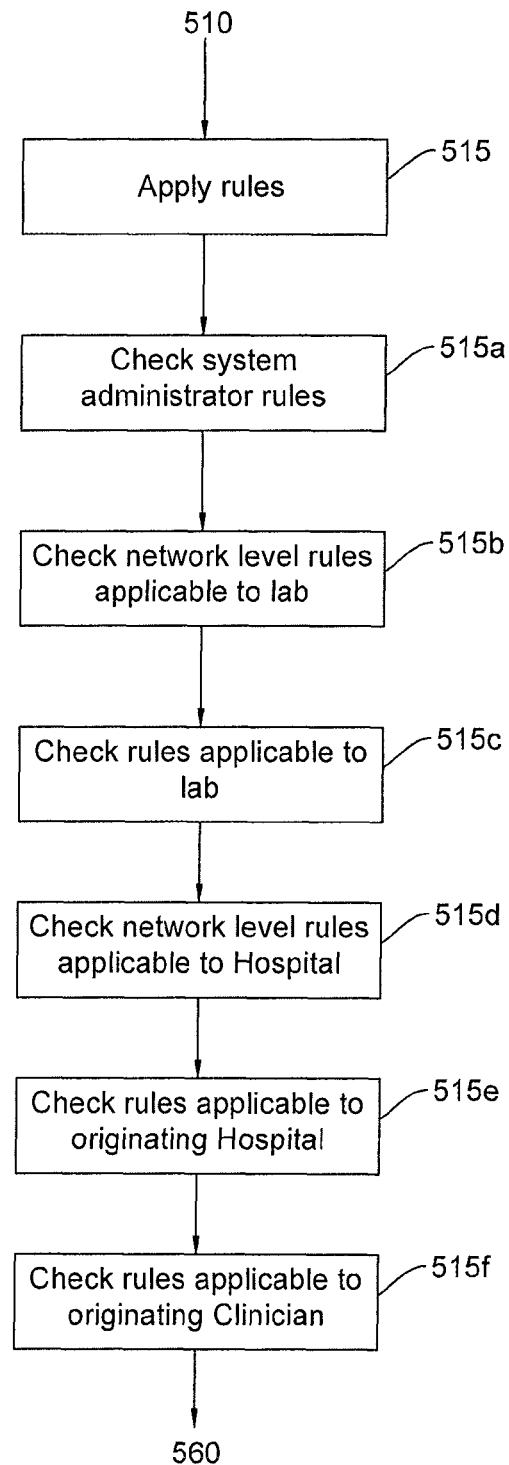
Figure 5C:
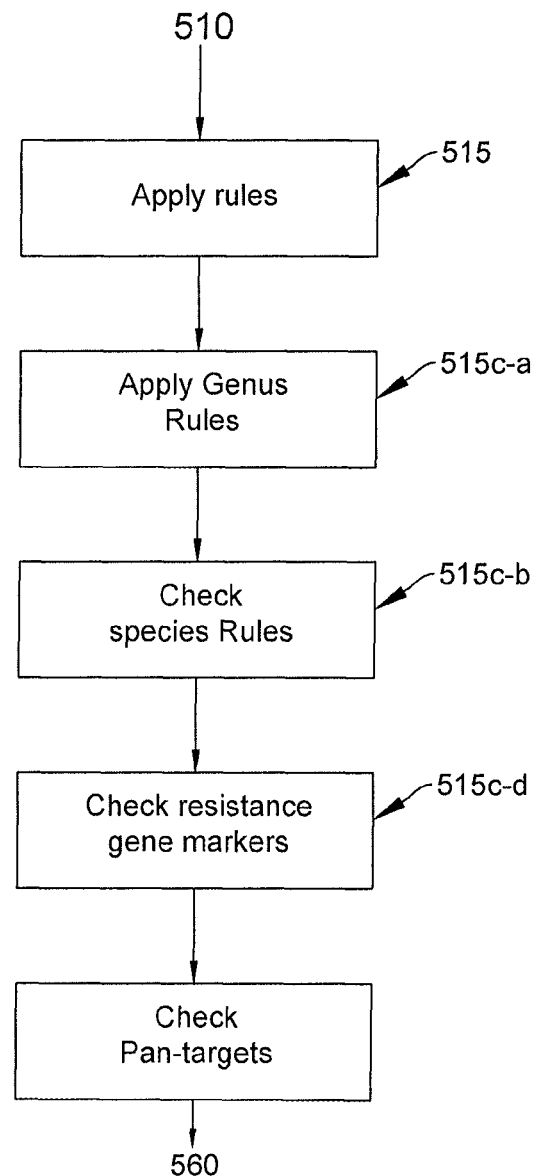
Figure 5D:
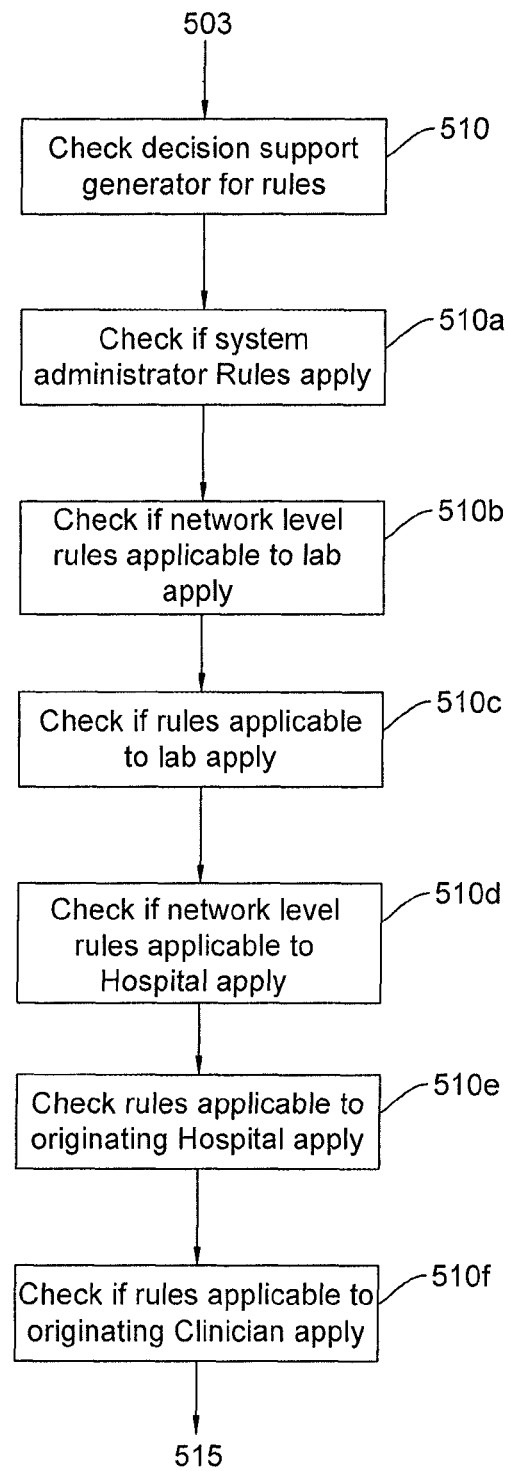

FIG. 5*a* is a flow chart of an example of operations that the decision support generator 140 may perform when applying the rules to the detection results. FIGS. 5*b* and 5*c* show the details of the application of the rules in step 515 of FIG. 5*a*. FIG. 5*d* shows the details of the application of the rules in step 510 of FIG. 5*a*.

The decision support generator 140 receives a test results from the AAM (pathogen detector 104 in FIG. 1 or 503 in FIG. 5*a*). In some embodiments, a check is made to see if customized lab settings are in effect for the corresponding laboratory (505) (not shown). For example, if the laboratory has selected under system settings that all results be manually reported or if the laboratory has selected that only test results with 3 or less detected pathogens are reported. If a customized lab setting is violated or indicates that further processing of the test order should not be conducted, the test results are passed to the appropriate test result execution process which is sometimes the database (117 of FIG. 1). For example, the test result may be manually reported, re-run, etc. In this way customized rule settings are bypassed. If a customized lab setting is not violated, the test results are passed to the Decision support generator for sample processing 730.

In some cases, no check is made to see if customized lab settings are in effect for the corresponding laboratory (505) and the test result is immediately processed by steps 510-530.

If no customized lab settings are in effect or the customized lab settings are scheduled to be evaluated after application of templated comments, the decision support generator checks to see if there are any applicable rules. All the rules may be applied 510-Y to all cartridges regardless of user type (i.e. all the rules in 515 such as 515*a-f* are applied). Alternatively, not all of the rules may be applied to all of the test results 510-N, the decision support generator may check the rules to see which rules to apply going from highest to lowest level of authority (510*a-f* in FIG. 5*d*): system administrator rules are analyzed first to see if they should be considered (51*oa*). Then it checks rules associated with a laboratory overseer (if any) to see if they should be considered (51*ob*), rules for the hospital network overseer (if any) to see if they should be considered (510*c*), rules for a hospital overseer (510*d*) if any to see if they should be considered, rules for a hospital (510*e*) if any to see if they should be considered, rules for a user (51*of*) if any to see if they should be considered. Once all of the outcomes from all of the checks (510*a-f*) are determined, the check outcomes are reviewed to determine the appropriate rules to be applied to the sample. (515 in FIG. 5A). In this way, the rules may be configured to provide user selectable scope of application i.e., when the user establishes a rule the user designates if the rule is applied to specific laboratories, hospital networks, hospitals, users or combination thereof.

Once the rules that should be applied to the sample have been identified, the rules generator applies the rules (515 in FIG. 5*a*) The decision support generator may check the rules based on the level of authority going from highest to lowest (515*a-f* in FIG. 5*b*): system administrator rules are analyzed first to see if they are satisfied (515*a*). Then it checks rules associated with a laboratory overseer (if any) (515*b*), rules for the hospital network overseer (if any) (515*c*), rules for a hospital overseer (515*d*) if any, rules for a user (5150 if any. Once all of the outcomes from all of the checks (515*a-0* are determined, the rule outcomes are reviewed to determine the appropriate action to be taken (560 in FIG. 5A). In some cases, if rules conflict the rule from the highest level of authority is applied. In some cases, if rules conflict the templated comments from both or all rules are applied. If the determination outcome (560) is reject (560—reject), the templated comment is rejected and the process test results (580) may apply no templated comment or may apply a templated comment (also called a rejected templated comment). In some cases, a rejection templated comment is a comment that states that no templated comments were applied to the test result. If the outcome is warning (560—warning), the process test results (580) may apply a warning templated comment. If the outcome is approval (560—approval), the process test results (580) may apply a templated comment (also called an approved templated comment). If the decision support generator does not come back approved or warning from the determine action (560), it is assumed that the test result was rejected by the determine action and no templated comment is applied.

After associating a test result with a templated comment (s) a decision support report is created. A decision support report can include just the decision support information or can also include the detection result when it includes the detection result it is called a test report or detection report. After formation of the decision support report and/or test report, the report is checked to see if customized lab settings are in effect for the corresponding laboratory. For example, if the laboratory has selected under system settings that all results be manually reported or if the laboratory has selected that only test results with 3 or less detected pathogens are reported, or if the laboratory has selected that invalid results be manually reported, or if the laboratory has selected that no detected targets be manually reported or if the laboratory has selected that assays with invalid controls be manually reported or combinations thereof. If a customized lab setting is violated or indicates that further processing of the test result should be conducted, the test results are stored in a database (117 of FIG. 1). An authorized user may access the stored test results and may manually release the test report to the AAM and the AAM may release the test report to the hospital LIS. Manual release can be performed, for example, by pressing a release button (not shown) under system events. Alternately, the authorized user may attach a templated comment by going into tools, templated comments and adding a templated comment as described above. Alternately, the authorized user may re-run the sample.

When creating a rule, certain principles for the Templated Comments may apply: From the perspective of the decision support generator 140, Rules include logic statements that use an IF, THEN, and ELSE to define a set of conditions and define an action to take when those conditions are true. These IF/THEN/ELSE statements are referred to as Rules or rule parameters. The Rules may be created by manually defining the statements. No programming experience is required. The IF portion of a Rule states a condition or series of conditions to determine if the THEN statement and any actions associated with the THEN statement are to be performed. The IF statement is selected from a series of options that are shown in a drop drown menu or a series of drop-down menus. The THEN statement states decision support information such as treatment action, or series of actions, for the clinician to evaluate before modifying patient treatment if the IF condition(s) is true. The THEN statement is created by the user and is completely customizable. The ELSE statement states decision support information such as treatment action, or series of actions, for the clinician to evaluate before modifying patient treatment if the IF condition(s) is false. The ELSE statement is created by the user and is completely customizable. Actions may take the form of comments. The comments may be free-form text.

In some examples, rule statements may only be defined for active assays.

In some examples, the following data elements (target names) are available when defining rule statements for BCID Assays: Genus, Species, Pan Target (does not exist on FP assay), Resistance Gene Marker, and any combination thereof. In other examples, additional, fewer, or different data elements may be available to the user.

In some examples, the following data elements (target names) are available when defining rules statements for Respiratory Panel (RP) Assay: Target—all on Assay, Virus, Bacteria, Subtype, and/or any combination thereof.

In some examples, the decision support generator 140 only allows data elements (such as target names) to be used in IF statements. In some examples, the decision support generator 140 allows data elements (such as target names) to be used in THEN statements and/or the ELSE statements.

In some examples, the following operators are available when defining rule statements for any assay: {Result}—In the IF statement the Result operator is used to provide the list of possible results (in other words, Detected, Not Detected) for a data element. {AND}—In the IF statement, the AND operator may be used to link two or more conditions. The decision support generator 140 may evaluate these conditional statements independently, and if both (or all) are true, the THEN action may be taken. {OR}—In the IF statement, the OR operator is used to link two (or more) conditions. The decision support generator 140 may then evaluate these conditional statements independently, and if any or all values are true, the THEN action may be taken. The decision support generator 140 may evaluate conditional statements together, and if any or all values are true, the THEN action may be taken.

The decision support generator 140 may generate an entry in an audit log 710 when a rule is created, changed, enabled, disabled, or deleted in the Templated Comments view 302. The audit log may be viewable in the templated comments view 302 under Rules Table 304 under the heading "Created By," "Modified By" or "Modified date."

In an example, the decision support generator 140 also provides an audit log when a rule is modified (created, changed, enabled, disabled or deleted) in System Events. The Audit Log may include a rule ID of the edited rule and a username of the user account that edited the rule. In an example, the decision support generator 140 provides an audit log in System Events in response to activating or deactivating a rule. In an example, the decision support generator 140 includes a rule ID and a username of a user account that activated and/or deactivated the rule.

The decision support generator 140 may enable the following actions in response to the logic expression evaluating to true:

Associate the Comment—associate the templated comment with the test result to form a test report.

Print Comment—print the specified templated comment on the detection report

Add Comment—attached the specified comment to a result message transmitted to the LIS The decision support generator 140 may create an audit event when a rule is executed and applied for an accession ID Rule Editing The decision support generator 140 may provide a Rules Editing area (also called the Rules Table) in a graphical user interface for the user to define and edit rules. When a rule is selected (checked) in the Rules Table 304, the Assay type, Rule ID, IF logic, THEN and ELSE comments are displayed in the Templated Comments view 302.

The decision support generator 140 may alternately have a Rules Editing button (similar to the add and delete buttons). After the Edit Rule Button is selected the user selects the assay that the rule will be changed for from the Assay dropdown; After the Assay has been selected the user selects the Rule ID that will be changed for from the RULE ID drop down. When a Rule ID is selected in the rule dropdown the Assay type, IF logic, THEN and ELSE comments are displayed in the Templated Comments view 302.

Changing the IF Statement

In some examples, the decision support generator 140 enables the user to begin changing a predefined IF statement of a rule (or an IF statement previously created by a different user). If each rule has logic, data elements (such as target, treating clinician name, hospital origin, patient information and combinations thereof. Basically any information on the PTO may be associated with a filter and filtered at the rule configuration step as a data element), and result (detected/non detected), then each of these elements may be modified by selecting the element from an element dropdown list associated with the assay selected and changing it.

Changing the THEN statement

In some examples, the decision support generator 140 enables the user to change the THEN portion of the rule. The Then portion of the rule is not changed by a drop-down button, instead the user can edit the Then Statement directly in the Then Comment box.

Changing the ELSE Statement

In some examples, the decision support generator 140 enables the user to change the ELSE portion of the rule. The ELSE portion of the rule is not changed by a drop-down button, instead the user can edit the ELSE Statement directly in the ELSE Comment box.

Figure 6:
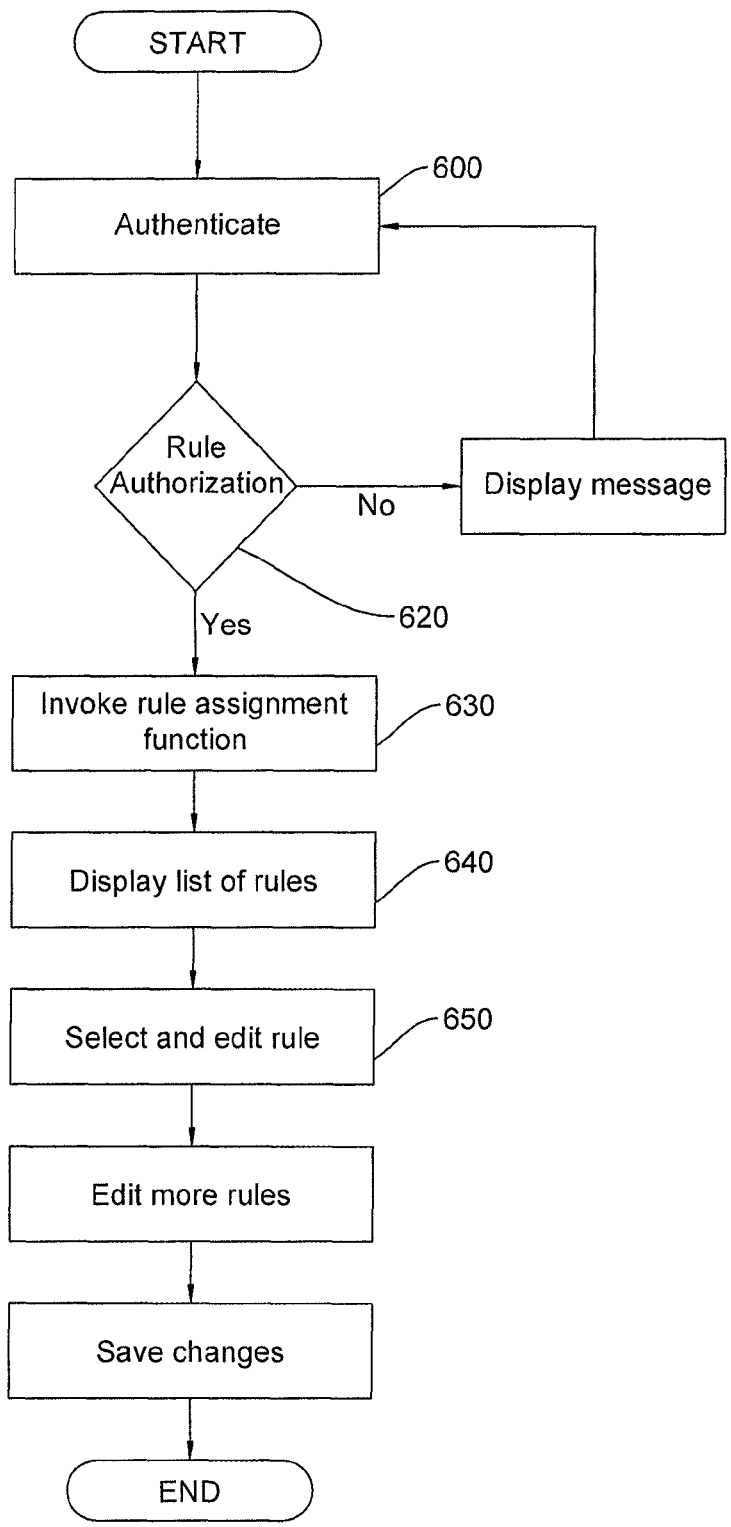
FIG. 6 is a flow chart of an example of logic for changing rules.

FIG. 6 is a flow chart of an example of logic for changing rules. In this process, a user is authenticated (600) by, for example, login with user ID and password. Typically, this user will be a system administrator for a laboratory network, however, any user having sufficient privileges may change the rules. A check (rule Authorization 620) will be run after log-in to determine which rules the user is authorized to change in the Rules Table 304. Rules which the user is authorized to change will be selectable (able to be checked) in the rules Table 304. Stated another way, when a user logs in, if they are not permitted to change certain rules, the check box in the Rules Table 304 will not be selectable (not able to be checked). If the user is not authorized (620—N) to change a rule and the rule is selected, a message is displayed indicating the user is not authorized to change that rule and the process returns to before step 620. If the level is appropriate for that user (620—Y), the user invokes the assignment update function (630). A list of all rules applicable for the selected level are displayed for editing (640) in the Rules Table 304 and the user may input, select and/or edit a rule (650). If the user desires to edit more rules (660—Y), the user proceeds to do that (650). If the user is done editing rules (660—N), the changes are saved to the decision support generator, the rules become immediately operational and the process exits.

Although not all users are authorized to make changes to rules, a read only version of the logic associated with a rule may be viewable to a user not authorized to change a rule.

Rules may also be set on an exception basis. In addition to the Logic AND and OR the logic NOT can be applied (not shown). When the NOT logic is applied, the selected data element must be missing from the result in order for the templated comment to be applied.

Rules may also be set on a universal application basis. For example, the list of target names can be configured to include "all targets" as an option. Selecting All targets means all of the detected targets are selected from the drop down and the OR logic is automatically applied between them.

In some cases more than one data element may be selected in a drop-drown, if more than one data element is selected, the OR logic is automatically applied between them. For example, if one wanted to impose a rule on all registered users in a particular hospital, one could impose the rule, excepting out any one or more particular registered representative (user account) from application of the rule. For example, a data element may be a list of registered users. All of the registered users may be selected from the drop down or certain users may be excepted (not selected) from the drop down.

It may be desirable to have separate laboratory overseers for each laboratory with reduced security access over that which would be held by a system administrator.

Rule Approval

As soon as a Rule is added it is automatically applied. However, in some cases the rule must be approved by an authorized user such as a pharmacist or antimicrobial stewardship committee member prior to being applied. In these cases, the Rule is stored in the Rules Table/storage database 117 and, in order to be applied, the Rule must be selected by an authorized user and an "apply" button (not shown) selected. If approval is revoked, an authorized user may select the Rule in the Rules table and de-select the "apply" button (not shown).

Rule Disablement

As soon as a Rule is added it may be automatically applied. However, in some cases a Rule is disabled. A rule is Disabled by selecting the Rule in the Rule Table 304 and hitting a Disable rule button (not shown). When a Rule is disabled it is displayed (i.e. not deleted) but is not evaluated by the decision support generator when processing a test result.

In some examples, the decision support generator 140 enables the user to disable a portion of the rule (this is similar to modifying the rule) by changing a predefined IF statement by selecting the data element from the data element dropdown list associated with the assay selected.

Enabling the THEN Statement

In some examples, the decision support generator 140 enables the user to disable a predefined THEN portion of the rule by selecting the text and changing it and/or deleting it.

Enabling the ELSE Statement

In some examples, the decision support generator 140 enables the user to disable a predefined ELSE portion of the rule by selecting the text and changing it and/or deleting it.

Rule Deletion

The decision support generator 140 may provide a graphical user interface with a Delete Rule button. A rule is deleted by selecting the Rule in the Rule Table 304 and hitting a delete rule button.

In some examples, the rule is deleted if the Rule ID is deleted. In some examples, the rule is deleted if the Assay ID is deleted. In some examples, the rule is deleted if the Rule ID and Assay ID are deleted. In some embodiments all the rules associated with an assay are deleted if the Assay ID is deleted.

Deleting the IF Statement

In some examples, the rule is deleted if all of the IF statements associated with that rule are deleted.

Deleting the THEN Statement

In some examples, the rule is deleted if the THEN statement associated with that rule is deleted.

Deleting the ELSE Statement

In some examples, the rule is deleted if the ELSE statement associated with that rule is deleted.

In some examples, to delete a rule the IF, THEN, and ELSE statements associated with that rule must be deleted. In some examples, the rule is deleted if all of the IF, THEN, and ELSE statements associated with that rule are deleted.

Rule Outcomes

The rules may have outcomes. Examples of the outcome for a Rule may be approval, warning, or rejection. The approval or acceptance outcome is the outcome when a rule is identified, and the templated comment is associated with the diagnostic result. In some cases, the association means the templated comment is reported with the diagnostic results. Alternatively, or in addition, the association means the templated comment is reported separately from the diagnostic results. A warning outcome may be the outcome when a rule is identified, and the templated comment is associated with a diagnostic result. In some cases, the association means the templated comment is reported with the diagnostic results. Alternatively, or in addition, the association means the templated comment is reported separately from the diagnostic results. In some cases, the association means the templated comment is reported with the diagnostic results and the detection report is stored on an instrument software database for manual review and/or manual release.

A rejection or denial outcome may be the outcome when a rule is not identified, and no templated comment is associated with the diagnostic result. In some examples, the rejection outcome is a default that occurs when no templated comments rules are applicable. In some examples, the rejection or denial outcome is indicated on the detection report, in other words, the clinician is advised that the results did not generate a templated comment. In some examples, the rejection or denial outcome applies a default templated comment for example advising the clinician that the antibiotic stewardship team should be consulted regarding treatment.

If all rules applicable to a particular result are satisfied with no reservations, one or more templated comments may be associated with the result. Templated comments may include an action plan. For example, the action plan may be "stop duplicative therapy," in which case the physician should analyze whether duplicative therapy should be stopped.

A rejection outcome may include templated comments with a rejection action plan. A rejection action plan informs the clinician that the diagnostic results did not produce a templated comment and require and/or suggest further consultation with the antimicrobial stewardship team is warranted. A rejection action plan may also be provided if, for example, the diagnostic assay produced an invalid result. A rejection action plan may say, for example, "the assay was invalid, repeat the diagnostic test or identify the pathogen by another means." The rejection action plan may say, for example, "consult antibiotic stewardship committee regarding treatment." A rejection outcome may be in conjunction with rejection action plans. A rejection action plan informs the clinician that the diagnostic results did not produce a templated comment and duplicative therapy should not be stopped until the pathogen is correctly identified.

A warning outcome may include templated comments with a warning action plan, such as a warning message. A warning action plan may be a message that informs the clinician that the results produced a templated comment but there was a warning result. The warning action plan may say, for example, "the diagnostic result produced a templated comment, but the antibiotic stewardship committee should be contacted regarding treatment." A warning action plan may be a message that informs the clinician that treatment may vary depending on patient type. The warning action plan may say, for example, "the diagnostic result produced a templated comment but if the patient is a pediatric patient the antibiotic stewardship committee should be contacted regarding treatment" or "the diagnostic result produced a templated comment but if the patient is an immune compromised patient then the antibiotic stewardship committee should be contacted regarding treatment."

A warning action plan may be in conjunction with a warning templated comment. For example, the warning templated comment might be appropriate based on a particular parameter provided for that organism such as combined with drug resistance. A warning templated comment may say, for example, "be aware that the identified microbe has a drug resistance gene." A warning templated comment may also be provided if, for example, the hospital is monitoring an infection of a particular microorganism to gauge if there is an outbreak. A warning templated comment may say, for example, "report all detections of E. coli to the CDC." A warning templated comment may also be provided if, for example, the diagnostic assay produced an invalid result. A warning templated comment may say, for example, "the assay was invalid, repeat the diagnostic test or identify the pathogen by another means."

A warning outcome may also be in conjunction with a Watch notice. For example, a detected organism may be flagged to be checked against the hospital's watch list to see if a warning message should be posted. This could happen for example when a hospital is monitoring whether there is an outbreak in that hospital. It may also be applied to a number of hospitals in a region by the system administrator to determine if there is an outbreak of a particular pathogen in a particular region. Each of these parameters may be associated with a particular rule at any particular authorization level.

In an example, the decision support generator 140 enables the following actions: Print Templated Comment—print the identified templated comment (based on the rules) on the detection report and/or Add templated comment—attach the identified templated comment to result message transmitted to the LIS.

The Rule Change Alert.

The rules may be set up to dictate that, when certain rules are changed, an alert is sent to the system administrator, laboratory overseer, hospital network overseer, hospital overseer, and/or user for approval. In these cases, the decision support generator 140 may generate a graphical user interface that includes a rule change alert button (not shown) that can be selected. When the rule change alter button is selected and when a rule is created or modified a notification is sent to rule management module 720. A user with authority to view the database can evaluate the change and elect to keep the changed rule, further modify the changed rule or delete the changed rule.

The system administrator, laboratory overseer, hospital network overseer, hospital overseer, and/or user may have several accounts and may request, that a rule from one account be transferred to another account. The request may be forwarded to the decision support generator 140 and, if the request is approved after being subjected to rules analysis, the transfer will be carried out. For example, a user may configure rules on a remote rules configuration instrument 102r and store them on a remote database (rule storage 700r (not shown) and/or preferably the instrument database 117r) associated with the remote rules configuration interface 107r. The user would log into several different instruments using a username and password. If the user had the appropriate credentials the user could then transfer (upload) the rules saved on the remote database 102r to the instrument 102. Alternatively, the user could transfer (download) the rules saved on the remote database to a removable disk and then connect the removable disk to the instrument 102 and transfer (upload) the rules saved on the removable disk to the instrument 102. The rules on the remote rules configuration instrument can be automatically transferred to the diagnostic instrument and stored on the diagnostic instrument. This can happen as each rule is created and applied it is transferred. Alternatively when the user logs out the new rules created are transferred as a one-time import. In this way if the remote rules configuration instrument is down the rules on the diagnostic instrument can still be applied. Alternatively, the rules can be stored on the remote rules configuration instrument. When the diagnostic instrument checks for decision support rules (step 510 in FIG. 5a) it will communicate with the remote rules configuration instrument and evaluate the rules stored there, in this way the diagnostic instrument receives rules live from the remote rules configuration instrument.

The remote rules configuration instrument 102r of FIG. 1b comprises a remote rules configuration interface 107r, memory 120r, communication interface 116r, processor 118r, storage database 117r and remote rules configure 140r. The remote rules configure 140r may have each of the elements in FIG. 7 and are referred to with the same number and "r" indicator for "remote". The remote rules configuration instrument 102r may communicate with the instrument 102 and the user 110 via the communication interface 116r. The remote rules configuration instrument 102r may be connected to more than one integrated diagnostic instruments. The remote rules configuration instrument 102r may be connected to more than one remote decision support generator 102rds.

Patient Data Elements

In some examples, patient data elements, such as patient age, gender, allergies, and/or other medications taken by the patient, are provided to the decision support generator 140 and evaluated when processing a rule. In some examples, patient data elements, are a type of data element provided in the data element dropdown (not shown). In some examples, patient data elements may be processed by the decision support generator 140 to determine if any of the rules have been satisfied. Consider the following example rule: If: {Result} on Genus:*Staphylococci* is Detected {AND} {Result} on Species: *S. aureus* is Detected {AND} {Result} on Resistance Marker: mecA is Not Detected; {AND} {Result} on patient data element: is pediatric {Yes}; Then: Add Comment "Notify MD, de-escalate to DOG if possible"

Consider the following example rule: If: {Result} on Genus: *Staphylococci* is Detected {AND} {Result} on Species: *S. aureus* is Detected {AND} {Result} on Resistance Marker: mecA is Not Detected; {AND} {Result} on patient data element: is allergies {Yes}; Then: Add Comment "Notify MD, de-escalate to DOC if possible"

In some examples, the patient data elements are provided to the decision support generator 140 in the form of a computer readable label placed on the cartridge containing patient information. In some examples, the patient data elements are manually imputed by the laboratory technician running the sample. In some examples, the patient data elements are provided to the decision support generator 140 in the PTO.

Decision Support Generator

Figure 7:
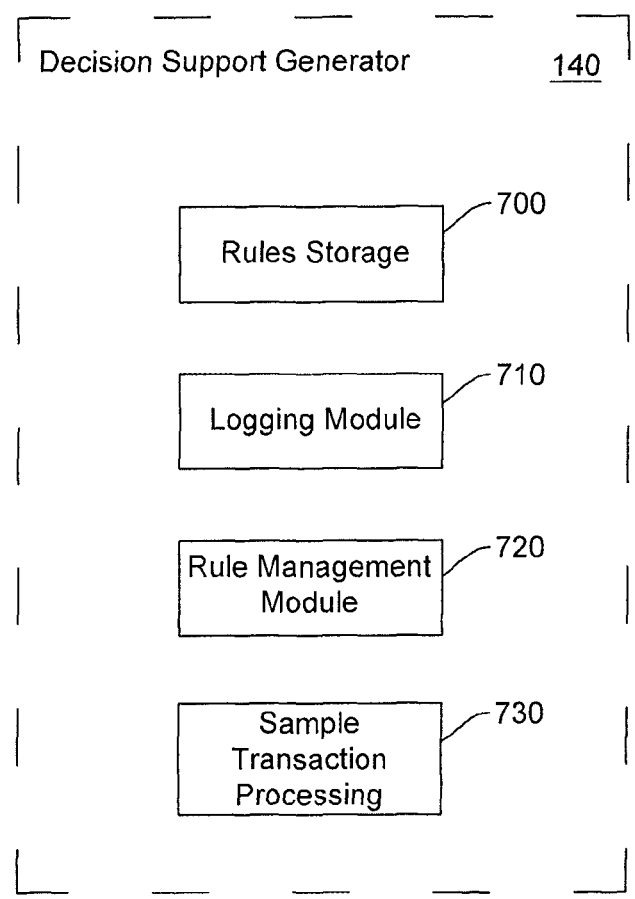
FIG. 7 is a schematic diagram of an example of the decision support generator.

FIG. 7 is a schematic diagram of an example of the decision support generator 140. The decision support generator 140 shown in FIG. 7 includes optionally a Rules storage 700, a logging module 710, a rules management module 720, and a Sample transaction processing module 730. These same features may be present in the remote decision support generator and would be referred to with the same numbers and an rds signifier.

The Rules storage 700 is an area of memory where the individual rules are stored with associated If Statements, Then Statements (templated comments) and ELSE statements (templated comments). In the example shown in FIG. 1, the rules storage 700 is a portion of the memory 120 of the integrated diagnostic instrument 102. In other examples, the rule storage 700 may be memory different than the memory 120 shown in FIG. 1. In other examples, the rules may be stored in the systems database 117 as shown in FIG. 1.

The logging module 710 may be any component configured to record changes made to a rule and/or indications that the rule was changed. Any change to the rules may be recorded by the logging module 710 as described herein. The logging module 710 may enable a system administrator, laboratory overseer, hospital network overseer, hospital overseer, and/or user to review rule changes.

The rules management module 720 may be any component configured to modify and/or create rules. Alternatively, or in addition, the rules management module 720 may be any component configured to generate a graphical user interface to display, modify, and/or create rules. As described herein the rules management module 720 may enable rules to be created and modified on a real-time basis, and viewed by authorized users interacting with the decision support generator 140, typically the user interacts with the decision support generator directly on the instrument but in some embodiments, the user interacts with the decision support generator over the communications interface 116 and/or a user input device (not shown). The logging module 710 may store information about rule changes and may generate rule change reports.

The sample transaction processing 730 may be any component configured to receive and process the test results. For example, the sample transaction processing 730 may receive the test result from the AAM, apply the Rules (rules stored in the Rules storage database 117) and associate a rule with the test result to form a test report.

The decision support generator 140 may selectively produce one or more of the following audit reports.

A rules assignment report may list any changes made to the decision support generator 140 for the integrated diagnostic instrument 102 as well as the personal identification of the individual who made the change.

A daily sample log may document an audit trail for patient samples that are processed by the decision support generator 140, as well as those samples that have not been approved for templated comments.

A sample processing log may provide pertinent information for samples processed by the decision support generator that received a particular templated comment. This log details whether the decision support generator automatically approved the templated comment or required human intervention. It also details whether the sample required additional approval because it failed one or more rule(s) and lists the rule(s) that may have been violated as well. If the sample is manually approved for templated comments, the report may indicate the user who approved the templated comments.

Rule Management

The operations that the rule management module 720 are configured to carry out the steps described throughout this document. The rule management module 720 is also configured to implement security measures. The normal security measures associated with any computer system may be available to the instrument 102. For example, access partitions may be enforced so that one hospital cannot access the information from another. Access partitions may be enforced so that one user type cannot access the information from other user types. Within a laboratory network or hospital network, access may be granted to a number of users by user ID (identification), each with the same authorizations or with different users having different authorizations appropriate to that user. Thus, the system, uses system operating features for security purposes.

Using Rules

In some examples, decision support generator 140 processes rules on valid results only. In other words, the instrument 102 may send only valid results to the decision support generator 140. Stated another way, in some examples, the decision support generator 140 does not process rules for invalid results obtained by the pathogen detector 104. When the decision support generator 140 does not process rules the test result is sent directly to the lab settings generator or the database 117. Alternatively, or in addition, the decision support generator 140 may not process or report rules for invalid results. In some examples, decision support generator 140 processes rules on valid and invalid results, in other words, the instrument sends valid and invalid results to the decision support generator 140. In some examples, if an invalid result is reported, a warning templated comment is generated by the decision support generator 140. A warning templated comment may say, for example, "the assay was invalid, repeat the diagnostic test or identify the pathogen by another means." In some examples, if an invalid result is reported, a rejection templated comment is generated by the decision support generator 140. A rejection templated comment may say, for example, "the assay was invalid, repeat the diagnostic test or identify the pathogen by another means."

In some examples, the decision support generator 140 processes rules before the detection report is created and templated comment messages are released to the LIS before the detection report. In some examples, the decision support generator 140 processes rules immediately after the detection report is created and templated comments are printed in the detection report and the detection report is released to the LIS. In some examples, the detection report is created first and released to the LIS and the templated comments message is released second to the LIS. In this situation, the decision support generator 140 may create a rules report (also called a templated comments report) which is released to the LIS. In any case, the templated comment may be associated with the detection result.

In an example, the decision support generator 140 creates an audit event when a rule is executed and applied for an accession ID. For example, "Rule ID xx-xxxx was applied to accession ID xxxxxxx."

Adding Templated Comments to LIS result message

Consider the following example rule:

If: {Result} on Genus: *Staphylococci* is Detected {AND} {Result} on Species: *S. aureus* is Detected {AND} {Result} on Resistance Marker: mecA is not Detected; Then: Add Comment "Notify MD, de-escalate to DOC if possible". DOC means drug of choice Consider the following example rule:

If: {Result} on Genus: *Staphylococci* is Detected {AND} {Result} on Species: *S. aureus* is Detected {AND} {Result} on Resistance Marker: mecA is Detected; Then: Add Comment "MRSA detected, patient should be treated with vancomycin".

In some examples, the decision support generator 140 may add a new segment to an HL7 message. In an example, the new segment is a Note and Comments (NTE) Segment.

In an example, the Notes and Comments (NTE) segment follow the OBX segments indicating that it contains clinically-relevant data. This is shown in Table 1 below.

TABLE 1

| Field # | Field Name | Field Description | Value |
|---|---|---|---|
| 1 | Sequence | Identifies the occurrence in the segment NTE sequence indicator | Numeric |
| 2 | Source of Comment | Source of Comment | Blank |
| 3 | Comment | Comment in formatted text | Comment in formatted text |

Example HL7 message: NTE|1||Notify MD, de-escalate to DOC if possible.

Alternatively, or in addition, the decision support generator 140 may send Templated Comments in the Comment record of an ASTM message. An example of such an ASTM message is shown in Table 2 below.

TABLE 2

| Field # | Field Name | Value | Field Description |
|---|---|---|---|
| 1 | Record ID | C | Comment record |
| 2 | Sequence Number | 1 | Sequence number of the comment record |
| 3 | Comment Source | I | I: Clinical instrument system |
| 4 | Comment Text | Text | Text description associated with comment |
| 5 | Comment Type | Any of the following: G, T, P, N, I | G: General text comment; T: Text name comment; P: Positive text comment; N: Negative text comment; I: System flag comment |

Example ASTM message: C|1|I|Notify MD, de-escalate to DOC if possible.|G<CR>

FIG. 8 is a block diagram representing an exemplary software architecture and information flow for system 1000, according to some embodiments. FIG. 8 is a reproduction of FIG. 63 from US Patent Application Publication US 2018/0095100 A1 by Nguyen et al. with added detail relating to the templated comments feature. In particular this aspect of Nguyen et al. is incorporated by reference in its entirety. System 1000 may comprise instrument software module (ISW) 1018, bay software module 1020, and an assay analysis module (AAM) 1022. The ISW 1018 may generally reside in an instrument 1002 (not shown) although portions of ISW 1018 may also reside in client device 1006 (not shown). The bay software module 1020 resides in processing bay 440 of an instrument (not shown) although portions or all of software module can also reside in other portions of instrument 1002 (not shown). The AAM module 1022 can reside in one or more of instrument 1002, client device 1006, and server 1008.

To perform a test, an assay definition file (ADF) 1024 may be received by the ISW 1018. The ADF 1024 may typically be defined by a client device before being transferred to ISW 1018. The ADF 1024 may comprise two portions including an OPUS file and an AAM file. The OPUS file may include parameters that define all operations controlled by the execution of bay software module 1020. The AAM file may include parameters that define analysis performed by AAM module 1022.

In operation, a sample is loaded into an instrument bay. The bay module 1020 may obtain scan data and log data which are sent to the ISW. The ISW sends the scan data to the AAM module. The AAM module may generate a test result as a result of the AAM file parameters being applied to the scan data. The test result is reported to the ISW. The ISW may apply the decision support generator. A decision support result may be generated by the ISW. The decision support result along with the test result is reported to the AAM module. The AAM module sends a report to the hospital LIS or other end client as further described below and in U.S. Publication no. 2018-0095100 which is herein incorporated by reference in its entirety.

Figure 9:
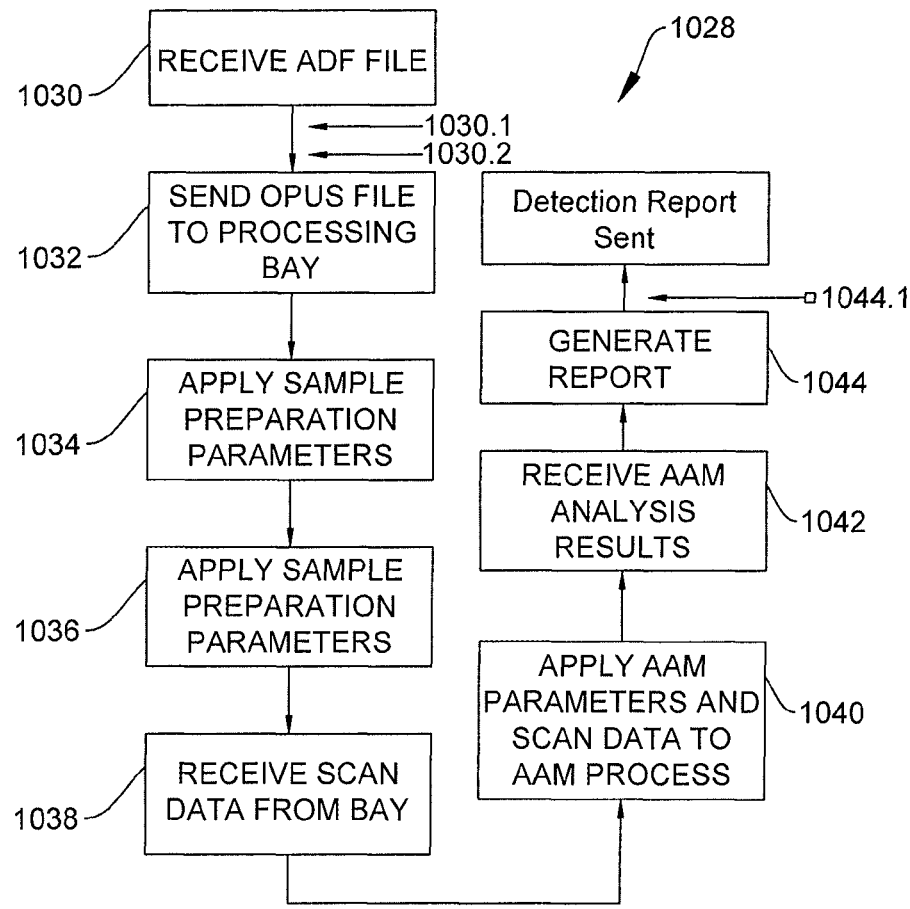
FIG. 9 is a flowchart representation of an exemplary process 1028 performed by an example of the system.

FIG. 9 is a flowchart representation of an exemplary process 1028 performed by system 1000 to analyze a sample, according to some embodiments. The steps of process 1028 concern software operations that may be concurrent with the sample preparation and sample reaction processes that are described with respect to FIGS. 16-23 (sample preparation) and FIG. 60 (sample reaction) of U.S. Publication no. 2018-0095100 which is herein incorporated by reference in its entirety. In preferred embodiments, sample preparation precedes sample reaction. As described with respect to FIG. 16 of U.S. Publication no. 2018-0095100, a fluid sample specimen may be dispensed into sample well 78. After sample well 78 is closed the cartridge 10 is placed into the processing bay 440 of instrument 1002. The steps of process 1028 can begin just prior to or after the receipt of cartridge 10 into processing bay 440. According to step 1030, ISW 1018 may receive ADF file 1024 (FIG. 8 of this application).

According to step 1030.1 the ISW 1018 may receive a Pending Test Order (PTO). According to step 1030.2 the ISW 1018 may receive an assay type from the assay cartridge. According to step 1032, ISW 1018 may send an OPUS portion of ADF file 1024 to the processing bay module 1020. The OPUS portion of the ADF file 1024 may comprise first parameters controlling the sample preparation module 70 and second parameters controlling the sample reaction module 240 (see FIG. 61 of U.S. Publication no. 2018-0095100).

According to step 1034 the first parameters may be applied to the sample preparation module to process the fluid sample specimen so that it is ready for the reaction module. According to step 1036, the second parameters may be applied to the sample reaction module to further process the fluid sample specimen and to generate scan data from sensors in the reaction module. According to step 1038 the sensor scan data may be transferred from the processing bay module 1020 to the ISW 1018. Also as part of step 1038, log data that can include sensing conditions and other data may be transferred from processing bay module 1020 to ISW 1018.

According to step 1040 the scan data and AAM file parameters that are part of the ADF file 1024 may be transferred to or define the AAM module. In some embodiments, AAM module may already have the AAM file parameters that are part of the ADF file 1024, and thus no transfer is necessary. According to step 1042, the AAM module may generate a test result as a result of the AAM file parameters being applied to the scan data. According to step 1044, a report may be generated that reports the test result from step 1042 to the ISW.

According to step 1044.1, templated comments may be added to the test results by the ISW and the final test results (including both the test results and templated comments) are sent back to the AAM. The AAM sends (either automatically or manually) a detection report (also referred to as a result report or test results) to either a network folder or the LIS interchange which converts the detection report into a physician test result report and sends the physician test result report directly to the physician or to the hospital's LIS which then sends the physician result report to the physician.

Detection Results and Decision Support Information

FIG. 11 illustrates an example of a detection report that includes detection results 1010 and decision support information 1020. The detection results 1010 identifies bacterial targets detected in the sample and bacterial targets not detected in the sample. The detection results 1010 also include pan targets and resistance gene targets that are detected or were not detected in the patient sample. The detection results 1010 also includes "flags" which detail abnormalities in assay testing.

FIGS. 12-13 illustrate additional examples of detection reports that include detection results 1010 and decision support information 1020.

The invention as a whole solves a problem that already existed within technology namely how to get physicians actionable results in a timely fashion without requiring the instrument to process complicated AI or the user to know complicated programming. The invention as a whole solves a computer problem because diagnostic instruments typically have limited processors and storage databases and would have insufficient memory and capabilities to manage and run complicated AI programs. But, because the IF statements (data elements) are pre-populated it eliminates the need to manually enter data. Indeed, the templated comments feature can be run on a system with a processor having core i3-i9 and memory ranging from 4 GB to 64 GB and indeed Applicant's system has a processor with core i5 (4570TE 2.7 Ghz) and a memory of 8 GB.

In other embodiments, templated comments are automatically generated on the integrated diagnostic system using AI. In such a system, the integrated diagnostic system receives data feedback from the clinician re patient treatment and patient outcome. The AI on the instrument analyses the feedback information to generate a templated comment. The templated comment can be reviewed and approved by a user before application of the templated comment to detection reports to ensure compliance with hospital rules and regulations.

The invention as a whole simplifies the process of providing the clinician with actionable treatment guidelines which are specific to their hospital or region. The invention as a whole avoids a one-size-fits-all to results reporting. The invention as a whole deals with solving a specific interface problem, i.e., the user can select from a series of selectable data elements to define IF statements.

The rule reconciler improves a process (rule creation and avoiding conflicting rules). When a user creates a new predefined THEN statement, the software is doing something the human brain could not do on its own.

The invention as a whole amounts to more than just receiving test results and applying treatment guidelines. The claimed invention addresses the challenge of providing a clinician with time sensitive information and decision support information even when institutional decision support providers (pharmacists and antimicrobial stewardship committees) are unavailable. This is addressed by having user (pharmacists and antimicrobial stewardship committees) configurable rules which cause decision support information to be directly associated with a detection result. The system bypasses the need for LIS middleware with a solution that is necessarily rooted in computer technology, similar to DDR Holdings. The configurable rules bypass the need to create a system which uses complicated artificial intelligence to evaluate search criteria.

"Integrated Diagnostic Instrument" also referred to as "Rules-based antimicrobial detection and reporting system" means a Diagnostic Instrument which is user configurable and associates templated comments with test result.

"Templated comments" also referred to as "decision support information" or "treatment decision support information" means decision support that assists clinicians to interpret and/or act on results. Templated comments are based on the decision support generator having rules created by the user.

"Decision support report" means a report conveying templated comments. In some cases, the decision support report is associated with a test result and in others it is not.

"User selectable scope of application" means the user defines how broadly or narrowly the rule is applied to test results.

"Data element" refers to an IF statement(s) that has pre-populated choices for the user to select. The data element can be any prepopulated information such as list of assays, list of targets, list of user types, patient data etc.

XOR or XOR gate implements an exclusive or; that is, a true output results if one, and only one, of the inputs to the gate is true. If both inputs are false (0/LOW) or both are true, a false output results.

"LI" refers to a Integrated Diagnostic Instrument's LIS Interchange: The application that controls the LIS functionality for the Integrated Diagnostic Instrument "LIM" refers to the Integrated Diagnostic Instrument's LIS Interchange Manager: A Graphical User Interface (GUI) to configure settings, monitor LIS communication, perform system checks and view transaction logs.

Derivatives may be N6 (FIG. 1D as shown "LIS Interchange" refers to the Integrated Diagnostic Instrument's LIS Interchange Service: A windows service that runs in the background to provide LIS communication between the instrument software and the LIS interface.

"ISW" refers to Instrument Software: The application that provides the high-level settings to enable or disable the instrument LIS interface; in addition to other instrument settings "PTO" refers to Pending Test Order: A test request from the LIS/host to be performed by the instrument.

"accession ID is a unique identifier given to a sample to allow tracking (i.e., the chain of custody that ties a sample and the associated results to a patient). The ID is usually generated by the LIS. When the patient sample gets to the lab, the accession ID barcode is placed on the cartridge before processing, which allows for tracking of results.

The rules-based management system is designed to operate on a diagnostic instrument. The term "detection system" or "pathogen detector" as used herein refers to a method that enables visualization of PCR-amplified nucleic acid products. The term "detection device" is a device that implements the detection system, Examples of suitable detection systems include systems that depend on detection of color, radioactivity, fluorescence, chemiluminescence or electrochemical signals, with the latter finding particular use in the present invention. For some nucleic acid detection systems, the target sequence is generally amplified, and during amplification, a label is added. The compositions of the invention may additionally contain one or more labels at any position. By "label" herein is meant an element (e.g. an isotope) or chemical compound that is attached to enable the detection of the compound. Preferred labels are radioactive isotopic labels, and colored or fluorescent dyes. The labels may be incorporated into the compound at any position. In addition, the compositions of the invention may also contain other moieties such as cross-linking agents to facilitate cross-linking of the target-probe complex. See for example, Lukhtanov et al., Nucl. Acids. Res. 24(4):683 (1996) and Tabone et al., Biochem. 33:375 (1994), both of which are expressly incorporated by reference.

The term "de-escalation targets" or "contamination rule out target" means a microorganism which is often associated with contamination such as *Propionibacterium acnes, Staphylococcus epidermidis, Micrococcus, Lactobacillus* or *Corynebacterium*. De-escalation targets may be present as a contamination from blood draw but may also be a clinically relevant infection.

The term "infection" means the invasion of a host organism's body by another organism or entity (pathogen), for example, a fungi or bacteria. The meaning of the term "co-infection" as used herein means "double infection," "multiple infection," or "serial infection" and is used to denote simultaneous infection with two or more infections/pathogens.

The term "determinants of antimicrobial resistance" relates to a gene responsible for the development of resistance in the bacteria which actively counteracts the effect of an antibiotic. Particularly, genetic determinants of resistance to methicillin (mecA and mecC) and vancomycin (vanA and vanB) are envisaged. Genes associated with genetic determinants of resistance such as CTX-M, NDM, IMP, OXA, KPC, VIM are envisaged.

"Diagnostic systems" may provide molecular diagnostic methods and compositions based on the detection of target analytes, including nucleic acids, and in some cases may be completely integrated "sample to answer" systems, that do not require off chip handling of the sample such as (cell lysis, for example), and sample preparation prior to detection. Thus, in accordance with aspects of the current system, a sample is loaded onto a test platform and the target analyte sample is extracted, amplified as necessary (for example, when the target analyte is a nucleic acid using polymerase chain reaction (PCR) techniques, although isothermal amplification methods may be utilized as well), and then detected using electrochemical detection, all on a microfluidic platform, generally referred to herein as a "multiplex cartridge" or a "fluid sample processing cartridge."

The electrochemical detection system used herein uses a separate signal probe or label probe having an electron transfer moiety (ETM). That is, one portion of the label probe directly or indirectly binds to the target analyte, and one portion comprises a recruitment linker comprising covalently attached ETMs. In some systems, these may be the same. In an example, the ETM is responsive to an input waveform. In an example, the ETM is a metallocene. In an example, the metallocene is a ferrocene. In an example, the ferrocene is a ferrocene derivative. Preferred ferrocene derivatives may be N6 (FIG. 1D as shown in U.S. Pat. No. 9,891,215, incorporated herein by reference), QW56 (FIG. 2A as shown in U.S. Pat. No. 9,891,215), and QW80 (FIG. 2B as shown in U.S. Pat. No. 9,891,215).

The expression "electrochemical system" or "electrochemical detection system" or "automated nucleic acid testing system" refers to a system that determines the presence and/or quantity of a redox analyte through measurements of electrical signal in a solution between a working electrode and a counter electrode, such as induced by a redox reaction or electrical potential from the release or absorption of ions. The redox reaction refers to the loss of electrons (oxidation) or gain of electrons (reduction) that a material undergoes during electrical stimulation such as applying a potential. Redox reactions take place at the working electrode, and which, for chemical detection, is typically constructed from an inert material such as platinum or carbon. The potential of the working electrode is measured against a reference electrode, which is typically a stable, well-behaved electrochemical half-cell such as silver/silver chloride. The electrochemical system may be used to support many different techniques for determining the presence and concentration of the target biomolecules including, but not limited to, various types of voltammetry, amperometry, potentiometry, coulometry, conductometry, and conductimetry such as AC voltammetry, differential pulse voltammetry, square wave voltammetry, electrochemical impedance spectroscopy, anodic stripping voltammetry, cyclic voltammetry, and fast scan cyclic voltammetry. The electrochemical system may further include one or more negative control electrode and a positive control electrode. In the context of the invention, a single electrochemical system may be used to detect and quantify more than one type of target analyte. The use of electrochemical systems is described in more detail in U.S. Pat. Nos. 9,557,295, 8,501,921, 6,600,026, 6,740,518 and U.S. application publication no. 2016-0129437 which are herein incorporated by reference in their entirety.

The electrochemical system may also use a method comprising: contacting a nucleic acid solution with an oligonucleotide probe labeled at the 5'-terminal with an electrochemically active marker; hybridizing the oligonucleotide probe with a complementary target sequence present in the nucleic acid solution and thereby forming a double stranded hybridized nucleic acid; degrading the double stranded hybridized nucleic acid by digestion with a duplex specific 5' to 3' exonuclease to form a ononucleotide degraded probe labeled with the electrochemically active marker or a dinucleotide probe labeled with the electrochemically active marker; electrochemically discriminating a redox based signal of the mononucleotide probe or the dinucleotide probe from any undegraded or unhybridized oligonucleotide probe in the solution, wherein the redox based signal is influenced by at least the size of the probe to which the electrochemically active marker is attached; and detecting the target nucleic acid based on the discrimination of the redox based signal from the mononucleotide probe or the dinucleotide probe from any undegraded or unhybridized oligonucleotide probe as more fully described in U.S. Pat. No. 9,127,308 which is herein incorporated by reference in its entirety.

"Instrument" or "clinical diagnostic instrument" or "diagnostic instrument" means an instrument configured to process a fluid sample contained in a cartridge. The instrument comprises a number of components, including a central processing unit that allows independent bay controllers and electric and network connections to each tower (e.g., a module comprising one or more cartridge-processing bays), an optional identification tag reading device (e.g., a bar code scanner) and a touch screen user interface with individual icons corresponding to each bay. A cartridge is placed into an instrument bay and processed. The clinical diagnostic instrument as disclosed in U.S. Pat. No. 9,598,722, U.S. Publication no. 2014-0194305 and U.S. Publication no. 2018-0095100 which are herein incorporated by reference in their entirety is designed to accept and process a cartridge also described in U.S. Pat. No. 9,598,722, U.S. Publication no. 2014-0194305 and U.S. Publication no. 2018-0095100.

As used herein, the term "cartridge" or "consumable" is a Self-contained cartridge/consumable that includes the necessary components to perform a single BCID Panel test. A "cartridge" or "consumable" is a cartridge for performing assays in a closed sample preparation and reaction system as described in U.S. Pat. No. 9,598,722 which is herein incorporated by reference in its entirety. The invention provides cartridges comprising several components, including a biochip cartridge, a top plate, a liquid reagent module (LRM), and a housing that keeps the components together. The biochip cartage comprises a bottom substrate, a sample preparation zone, reagent zone, Sample Manipulation Zone, Amplification Zone, Detection Zones as further described in U.S. Patent Publication No. 2015/0323555 and U.S. Pat. No. 9,598,722 which are herein incorporated by reference in their entireties. Specifically, in the examples for detecting nucleic acid targets, the substrate comprises one or more amplification pathways/zones. The top plate is spotted with reagents and primers. During the spotting process, phenol red is added to the reagents and primers so that spotting may be visualized. The LRM includes fluid filled blisters, as generally depicted in FIG. 1 from U.S. Patent application publication no. 2014/0194305 which is herein incorporated by reference in its entirety. For example, lysis buffer (which in some cases may be water for hypotonic lysis, or may be a commercially available lysis buffer, such as those containing chiatropic salts such as guanidinium salts, and or high/low pH, and/or surfactants such as sodium dodecyl sulfate (SDS), Polysorbate 20, Triton-X, etc. is contained within a blister that is activated to add lysis buffer to the sample. These buffers and in particular Polysorbate 20 (such as Tween® 20) may be washed or they may remain in the sample upon amplification. The top plate may include a PDOT (or PEDOT) coating. PEDOT:PSS or poly(3,4-ethylenedioxythiophene) polystyrene sulfonate is a polymer mixture of two ionomers. One component in this mixture is made up of sodium polystyrene sulfonate which is a sulfonated polystyrene. Part of the sulfonyl groups are deprotonated and carry a negative charge. The other component poly(3,4-ethylenedioxythiophene) or PEDOT is a conjugated polymer and carries positive charges and is based on polythiophene. Together the charged macromolecules form a macromolecular salt. The top plate may be coated with Teflon®, Cytop®, or Fluoropel®, preferably Cytop®. Cytop® is an amorphous fluoropolymer with high optical transparency and excellent chemical, thermal, electrical and surface properties. As used herein, the term "cartridge sub-assembly" means the bottom plate and top plate together.

"Bay" or "instrument bay" or "cartridge bay" means a Stand-alone processing unit which runs a consumable. Bays as used herein are further described in U.S. patent application Ser. No. 14/062,860, U.S. Patent Publication No. 2015/0323555 and U.S. Pat. No. 9,598,722 which are herein incorporated by reference in their entireties.

The term "detect", "detecting" or "detection" refers to an act of determining the existence or presence of one or more targets (e.g., microorganism nucleic acids, amplicons, etc.) in a sample. As used herein, target detection occurs when the amplicon forms a hybridization complex with the complimentary signal and capture probe.

As used herein, the term BCID-GP means Blood Culture Identification—Gram-Positive Panel. The BCID-GP panel includes all of the oligonucleotides and reagents for carrying out a nucleic acid amplification reaction for the following targets: *Bacillus cereus* group, *Bacillus subtilis* group, *Corynebacterium, Cutibacterium acnes, (Propionibacterium acnes), Enterococcus, Enterococcus faecalis, Enterococcus faecium, Lactobacillus, Listeria, Listeria, monocytogenes, Micrococcus, Staphylococcus, Staphylococcus aureus, Staphylococcus epidermidis, Staphylococcus lugdunensis, Streptococcus, Streptococcus agalactiae* (GBS), *Streptococcus anginosus* group, *Streptococcus pneumoniae, Streptococcus pyogenes* (GAS) and can identify the following Resistance Genes: mecA, mecC, vanA, vanB and can identify the following Pan Targets: Pan Gram-Negative, Pan *Candida* as well as the capture and signal probes to form the hybridization complex necessary to detect the targets above. The above BCID-GP targets are the data elements (target names) available when defining rule statements for the BCID-GP Assays.

As used herein, the term BCID-GN means Blood Culture Identification—Gram-Negative Panel. The BCID-GN panel includes all of the oligonucleotides and reagents for carrying out a nucleic acid amplification reaction for the following targets: *Acinetobacter baumannii, Bacteroides fragilis, Citrobacter, Cronobacter sakazakii, Enterobacter* (non-*cloacae* complex), *Enterobacter cloacae* complex, *Escherichia coli, Fusobacterium nucleatum, Fusobacterium necrophorum, Haemophilus influenza, Klebsiella oxytoca, Klebsiella pneumoniae, Morganella morganii, Neisseria meningitidis, Proteus, Proteus mirabilis, Pseudomonas aeruginosa, Salmonella, Serratia, Serratia marcescens, Stenotrophomonas maltophilia*, and can identify the following Resistance Genes, CTX-M, KPC, NDM, VIM, IMP, OXA, and can identify the following Pan Targets: Pan Gram-Positive, Pan *Candida* as well as the capture and signal probes to form the hybridization complex necessary to detect the targets listed above. The above BCID-GN targets are the data elements (target names) available when defining rule statements for the BCID-GN Assays.

As used herein, the term BCID-FP means Blood Culture Identification—Fungal Panel. The BCID-FP panel includes all of the oligonucleotides and reagents for carrying out a nucleic acid amplification reaction for the following targets: *Candida albicans, Candida dubliniensis, Candida famata, Candida glabrata, Candida guilliermondii, Candida kefyr, Candida krusei, Candida lusitaniae, Candida parapsilosis, Candida tropicalis, Cryptococcus gattii, Cryptococcus neoformans, Fusarium, Malassezia furfur, Rhodotorula, Trichosporon* as well as the capture and signal probes to form the hybridization complex necessary to detect the targets listed above. The above BCID-FP targets are the data elements (target names) available when defining rule statements for the BCID-FP Assays.

CNS Panel includes all of the oligonucleotides and reagents for carrying out a nucleic acid amplification reaction for the following targets: Bacterial, viral, and fungal targets associated with central nervous system infections from a cerebrospinal fluid sample as well as the capture and signal probes to form the hybridization complex necessary to detect the targets listed above. GASTROINTESTINAL PATHOGEN PANEL (GI) includes all of the oligonucleotides and reagents for carrying out a nucleic acid amplification reaction for the following targets Bacterial, viral, and parasitic targets associated with gastrointestinal infections from a stool sample as well as the capture and signal probes to form the hybridization complex necessary to detect the targets listed above. And specifically for *Salmonella, Campylobacter* group (*C. coli/C. upsaliensis/C. lari*), *Campylobacter jejuni, Shigella/Enteroinvasive E. coli* (EIEC), *Escherichia coli* (STEC) stx1/stx2, *Escherichia coli* (STEC) 0157, *Vibrio, V. cholera, V. cholerae* toxin, *Yersinia enterocolitica, Aeromonas, Clostridium difficile* tcdB, *Clostridium difficile* (Hypervirulent: tcdC deletion), Enteroaggregative *E. coli* (EAEC), Enteropathogenic *E. coli* (EPEC), Enterotoxigenic *E. coli* (ETEC) LT/ST, *Plesiomonas shigelloides*, Norovirus GI/GII, Rotavirus A, Adenovirus, Adenovirus F 40/41, Astrovirus (1-8), Sapovirus (I, II, IV, V), *Cryptosporidium, Cyclospora cayetanensis, Dientamoeba fragilis, Giardia lamblia, Entamoeba histolytica, Cystoisospora belli* as well as the capture and signal probes to form the hybridization complex necessary to detect the targets listed above.

HCV GENOTYPING PANEL (HCVg)includes all of the oligonucleotides and reagents for carrying out a nucleic acid amplification reaction for typing and subtyping of HCV 1a, 1b, 2a/c, 2b, 3, 4, 5, and 6 from plasma or serum as well as the capture and signal probes to form the hybridization complex necessary to detect the targets listed above. The above targets are the data elements (target names) available when defining rule statements for the identified Assays.

As used herein, the term "BCID-GP cartridge" or "BCID-GN cartridge" or "BCID-FP cartridge" means a cartridge for performing gram-positive, gram-negative, or fungal assays respectively in a closed sample preparation and reaction system as described in U.S. Pat. No. 9,598,722 which is herein incorporated by reference in its entirety. While this application contemplates the specific targets identified above, it is recognized that any bacterial, fungal, respiratory resistance gene target could be used.

As used herein, the term RP Panel means respiratory panel. The RP panel includes all of the oligonucleotides and reagents for carrying out a nucleic acid amplification reaction for the following targets: Adenovirus, Coronavirus (229E, HKU1, NL63, OC43), Human Metapneumovirus, Human Rhinovirus/Enterovirus, Influenza A, Influenza A H1, Influenza A H1-2009, Influenza A H3, Influenza B, Parainfluenza 1, Parainfluenza 2, Parainfluenza 3, Parainfluenza 4, Respiratory Syncytial Virus A, Respiratory Syncytial Virus B, *Chlamydia pneumoniae, Mycoplasma pneumoniae*. The above RP targets are the data elements (target names) available when defining rule statements for the RP Assay.

As used herein, the term "about" means encompassing plus or minus 10%. For example, about 90% refers to a range encompassing between 81% and 99% nucleotides. As used herein, the term "about" is synonymous with the term approximately.

The word "or" as used herein means any one member of a particular list and also includes any combination of members of that list.

The system 100 may include more, fewer, or different elements than shown in FIG. 1. For example, the system 100 may include the decision support generator 140 on a different device and connected to the diagnostic instrument 102 via a communications network (FIG. 1c). The system 100 may be implemented with additional, different, or fewer components.

The processor 118 may be in communication with the memory 120 and the communications interface 116. In one example, the processor 118 may also be in communication with additional elements, such as a display. Examples of the processor 118 may include a general processor, a central processing unit, a microcontroller, a server, an application specific integrated circuit (ASIC), a digital signal processor, a field programmable gate array (FPGA), and/or a digital circuit, analog circuit.

The processor 118 may be one or more devices operable to execute logic. The logic may include computer executable instructions or computer code embodied in the memory 120 or in other memory that when executed by the processor 118, cause the processor 118 to perform the features implemented by the logic. The computer code may include instructions executable with the processor 118.

The memory 120 may be any device for storing and retrieving data or any combination thereof. The memory may include non-volatile and/or volatile memory, such as a random-access memory (RAM), a read-only memory (ROM), an erasable programmable read-only memory (EEPROM), or flash memory. Alternatively, or in addition, the memory may include an optical, magnetic (hard-drive) or any other form of data storage device.

Each component may include additional, different, or fewer components. For example, the decision support generator 140 may include additional, different, or fewer components than illustrated in FIG. 7. The flow diagrams of logic may include additional, different, or fewer operations than shown.

The system 100 may be implemented in many different ways. Each module may be implemented as a circuit. Each circuit, such as the pathogen detector circuit 104, the LIS Interchange circuit 114, and the decision support generator circuit 140, may be hardware or a combination of hardware and software. For example, each circuit may include an application specific integrated circuit (ASIC), a Field Programmable Gate Array (FPGA), a digital logic circuit, an analog circuit, a combination of discrete circuits, gates, or any other type of hardware or combination thereof. Alternatively, or in addition, each circuit may include memory hardware, such as a portion of the memory 120, for example, that comprises instructions executable with the processor 118 or other processor to implement one or more of the features of the circuit. When any one of the circuits includes the portion of the memory that comprises instructions executable with the processor, the circuit may or may not include the processor. In some examples, each circuit may just be the portion of the memory 120 or other physical memory that comprises instructions executable with the processor 118 or other processor to implement the features of the corresponding circuit without the circuit including any other hardware. Each circuit includes at least some hardware even when the included hardware comprises software.

Some features are shown stored in a computer readable storage medium (for example, as logic implemented as computer executable instructions or as data structures in memory). All or part of the system and its logic and data structures may be stored on, distributed across, or read from one or more types of computer readable storage media. Examples of the computer readable storage medium may include a hard disk, a floppy disk, a CD-ROM, a flash drive, a cache, volatile memory, non-volatile memory, RAM, flash memory, or any other type of computer readable storage medium or storage media. The computer readable storage medium may include any type of non-transitory computer readable medium, such as a CD-ROM, a volatile memory, a non-volatile memory, ROM, RAM, or any other suitable storage device. However, the computer readable storage medium is not a transitory transmission medium for propagating signals.

The processing capability of the system 100 may be distributed among multiple entities, such as among multiple processors and memories, optionally including multiple distributed processing systems. Parameters, databases, and other data structures may be separately stored and managed, may be incorporated into a single memory or database, may be logically and physically organized in many different ways, and may be implemented with different types of data structures such as linked lists, hash tables, or implicit storage mechanisms. Logic, such as programs or circuitry, may be combined or split among multiple programs, distributed across several memories and processors, and may be implemented in a library, such as a shared library (for example, a dynamic link library (DLL)).

All of the discussion, regardless of the particular implementation described, is exemplary in nature, rather than limiting. For example, although selected aspects, features, or components of the implementations are depicted as being stored in memories, all or part of the system or systems may be stored on, distributed across, or read from other computer readable storage media, for example, secondary storage devices such as hard disks, flash memory drives, floppy disks, and CD-ROMs. Moreover, the various modules and screen display functionality is but one example of such functionality and any other configurations encompassing similar functionality are possible.

The respective logic, software or instructions for implementing the processes, methods and/or techniques discussed above may be provided on computer readable storage media. The functions, acts or tasks illustrated in the figures or described herein may be executed in response to one or more sets of logic or instructions stored in or on computer readable media. The functions, acts or tasks are independent of the particular type of instructions set, storage media, processor or processing strategy and may be performed by software, hardware, integrated circuits, firmware, micro code and the like, operating alone or in combination. Likewise, processing strategies may include multiprocessing, multitasking, parallel processing and the like. In one example, the instructions are stored on a removable media device for reading by local or remote systems. In this way rules set up on one instrument can be uploaded to a different instrument. In order to achieve this, under the templated comments view there would be a "Save to Remote Device" button (not shown) which would automatically save the rules to a removable media device. In order to upload templated comments, when a removable media device is connected to the instrument, the templated comments configuration view will have a selectable "upload from Remote Device" button (not shown). When the upload button is selected all of the rules on the removable drive will automatically load into the Rules Table 304 and will be automatically applied on that instrument. The user can then select a rule on the Rules Table to delete or change it.

In other examples, the logic or instructions are stored in a remote location (such as a remote rules configuration instrument 102r or a cloud) for transfer through a computer network or over telephone lines. In order to upload templated comments, from a remote location, the templated comments configuration view will have a selectable "remote upload" button (not shown). When the remote upload button is selected, the instrument connects to a remote agent (such as 102r or a cloud). The user will be prompted to supply a user ID and password. Once entered the user can select which rules to apply from a Rules List located in the remote rule configure 140r similar to the Rules Table 304. When the rules from the Rules List are selected the user presses an apply button and the rules are automatically transferred over a wireless network to the instrument 102 and populated in the Rules Table 304 and are automatically applied to the instrument 102. The user can then select the rule to delete or change it as needed.

In yet other examples, the logic or instructions are stored within a given computer, central processing unit ("CPU"), graphics processing unit ("GPU"), or system.

Furthermore, although specific components are described above, methods, systems, and articles of manufacture described herein may include additional, fewer, or different components. For example, a processor may be implemented as a microprocessor, microcontroller, application specific integrated circuit (ASIC), discrete logic, or a combination of other type of circuits or logic. Similarly, memories may be DRAM, SRAM, Flash or any other type of memory. Flags, data, databases, tables, entities, and other data structures may be separately stored and managed, may be incorporated into a single memory or database, may be distributed, or may be logically and physically organized in many different ways. The components may operate independently or be part of a same program or apparatus. The components may be resident on separate hardware, such as separate removable circuit boards, or share common hardware, such as a same memory and processor for implementing instructions from the memory. Programs may be parts of a single program, separate programs, or distributed across several memories and processors.

A second action may be said to be "in response to" a first action independent of whether the second action results directly or indirectly from the first action. The second action may occur at a substantially later time than the first action and still be in response to the first action. Similarly, the second action may be said to be in response to the first action even if intervening actions take place between the first action and the second action, and even if one or more of the intervening actions directly cause the second action to be performed. For example, a second action may be in response to a first action if the first action includes setting a Boolean variable to true and the second action is initiated if the Boolean variable is true.

To clarify the use of and to hereby provide notice to the public, the phrases "at least one of <A>, <B>, . . . and <N>" or "at least one of <A>, <B>, <N>, or combinations thereof" or "<A>, <B>, . . . and/or <N>" are defined by the Applicant in the broadest sense, superseding any other implied definitions hereinbefore or hereinafter unless expressly asserted by the Applicant to the contrary, to mean one or more elements selected from the group comprising A, B, . . . and N. In other words, the phrases mean any combination of one or more of the elements A, B, . . . or N including any one element alone or the one element in combination with one or more of the other elements which may also include, in combination, additional elements not listed. Unless otherwise indicated or the context suggests otherwise, as used herein, "a" or "an" means "at least one" or "one or more."

Methods of Treatment by the Clinician

Also contemplated herein are methods of treatment by the clinician. Specifically contemplated is the clinician administering an effective amount of a drug based on a detection result which reports both a microorganism and provides templated comments, i.e., treatment decision support information.

When a patient comes in for treatment, they typically undergo a common empiric therapy, namely, treatment with beta-spectrum lactam, often combined with an aminoglycoside or a fluoroquinolone, and according to the medical context antiviral and/or antifungal drugs may be added. In other words the patient is typically treated with a board-spectrum antibiotic and may often be treated with a combination therapy (2-3 antibiotics). The patient's blood is then subject to a gram stain. Based on the gram stain result, the board-spectrum combination therapy may be de-escalated to a single Gram stain specific therapy. The patient's blood is then subject to an organism specific diagnostic assay (monotherapy). If an organism is identified by the organism specific diagnostic assay treatment can be changed to more appropriately target the specific organism and/or resistance gene identified. In some cases if the diagnostic assay provides treatment recommendations, the clinician can consider the treatment recommendations and modify (escalate or de-escalate) treatment. FIG. 15 is a summary of various treatment decision support (templated comments) which may be provided with a detection result, the comments under "further treatment decision support" comments may also be provided as part of the treatment decision support information. The example methods described herein are well suited for rapid targeted treatment based on organism specific results combined with treatment decision support. For example, the results of a species specific organism combined with treatment decision support may be employed to modify antimicrobial therapy by narrowing the spectrum of initially-prescribed broad-spectrum antibiotics (i.e. to rapidly de-escalate broad-spectrum treatment). Such an approach provides guided and rapid re-vectoring of antimicrobial therapy for cases where antimicrobial therapy has already been initiated. Alternatively, in cases where antimicrobial therapy has not yet been initiated prior to the availability of test results, the methods disclosed herein may be employed to provide guided initial therapy that avoids the use of broad-spectrum antibiotics. The ability to avoid the use, or overuse, of broad spectrum antibiotics, may be beneficial in reducing the co-morbidities and increased mortality risk that is associated with broad spectrum antibiotic use. For example, such a strategy may be employed to support the delivery of treatment that avoids or reduces the risks of toxicity, secondary infections due to the eradication of natural flora, and risk of development of antibiotic resistance, which are all associated with broad spectrum antibiotic use. The ability to quickly identify the causative organism(s) and provide treatment decision support will aid in the administration of appropriate antibiotic therapy which should result in improved patient outcomes as well as reduce overall costs to the healthcare system.

A method comprises administering an organism specific antibiotic after submitting a patient sample to diagnostic testing wherein the diagnostic test results are reported with templated comments.

Paragraph 1: A method for treating a patient having blood that is infected or possibly infected with a microorganism, the method comprising: detecting the microorganism in the patient's blood, wherein detecting the microorganism comprises detecting, by a diagnostic instrument, a target analyte in a patient sample; generating, by the diagnostic instrument, a detection result, which includes an identity of the microorganism; generating decision support information by the diagnostic instrument, wherein generating the decision support information includes applying, by the diagnostic instrument, a set of configurable rules to the detection result, wherein each rule in the set of configurable rules comprises a corresponding IF condition, which when evaluated, indicates whether to include corresponding decision support information in a detection report; and evaluating the decision support information generated by the diagnostic instrument and administering an effective amount of a monotherapy to the patient.

A method of administering an effective amount of specific antibiotic to a patient comprising: administering an effective amount of at least one broad-spectrum antibiotic; obtaining a diagnostic result from a diagnostic instrument; obtaining treatment guidelines from the diagnostic instrument; evaluating the diagnostic result and treatment guidelines; administering an effective amount of an organism specific antibody based on the diagnostic result and treatment guidelines from the diagnostic instrument.

The invention relates generally to the administration of highly specific antibiotics to a patient in need thereof. The invention relates generally to the removal of a broad-spectrum, antibiotics to a patient in need of a specific antibiotic. The invention relates generally to the substitution of a broad-spectrum antibiotic with an organism specific antibiotic administered to a patient in need thereof. The invention relates generally to the substitution of a broad-spectrum antibiotic with a monotherapy antibiotic administered to a patient in need thereof. The invention relates generally to method of treating a patient infected with a microorganism comprising obtaining treatment decision support information from a diagnostic instrument; evaluating the treatment decision support information and administering an appropriate antibiotic. The microorganism can cause a respiratory infection. The microorganism can be a blood infection. The microorganism can cause sepsis or can be suspected of causing sepsis.

Disclosed is a method of treating or preventing septic shock, the method comprising administering to a patient having septic shock or at risk of having septic shock a therapeutically acceptable amount of a broad-spectrum antibiotic; subjecting the patient sample to gram-staining; subjecting the sample to an organism specific diagnostic test on a diagnostic instrument; obtaining organism identification and treatment decision report based on the organism identified by the diagnostic instrument; stopping treatment of the broad-spectrum antibiotic and administering an organism specific antibiotic. For example if the organism is *S. aureus* and mecA/C then the treatment decision report advises to treat with vancomycin. For example, if the organism identified is *S. aureus* and no mec then the treatment decision report advises to de-escalated to a beta-lactam (eg. nafcillin or cefazolin). For example, if the target diagnostic result is a common contaminant (also referred to as a de-escalation target such as *Corynebacterium, C. acnes, Lactobacillus, B. subtilis*) and infection is only present in one blood culture bottle then the treatment decision report advices to discontinue/de-escalate treatment. For example, if the target diagnostic result is an anaerobe (*B. fragilis, Fusobacterium*) then the treatment decision report advises to treat with piperacillin/tazobactam or metronidazole. In each of the above examples, the clinician evaluates the detection result and treatment decision report and administers an organism specific antibiotic based on the detection result and treatment decision report information.

Monothereapy options include: piperacillin/tazobactam 4.5 g IV q6h; cefepime 2 gm IV q6h; meropenem 1 gm q8h; ceftriaxone 1-2 g IV q12h; imipenem/cilastin 500 mg IV q6h; doripenem 500 mg IV 8h; cefotaxime 2 gm IV q6h, ceftaroline fosamil 600 mg IV q8h; ceftazdime 2 gm IV q8h; ceftazidime/avibactam 2 g/0.5 g IV q8h; ceftolozane/tazobactam 3 g IV q8h. As such disclosed is a method of treating a patient infected with a microorganism comprising obtaining treatment decision report information from a diagnostic instrument; evaluating the treatment decision report information and administering an antibiotic selected from the group consisting of piperacillin/tazobactam 4.5 g IV q6h; cefepime 2 gm IV q6h; meropenem 1 gm q8h; ceftriaxone 1-2 g IV q12h; imipenem/cilastin 500 mg IV q6h; doripenem 500 mg IV 8h; cefotaxime 2 gm IV q6h, ceftaroline fosamil 600 mg IV q8h; ceftazdime 2 gm IV q8h; ceftazidime/avibactam 2 g/0.5 g IV q8h; or ceftolozane/tazobactam 3 g IV q8h.

While various embodiments have been described, it will be apparent to those of ordinary skill in the art that many more embodiments and implementations are possible.

Accordingly, the embodiments described herein are examples, not the only possible embodiments and implementations.

The Rules Based Management System can be further understood by the following numbered paragraphs:

Paragraph 1: A diagnostic instrument, comprising: a first interface configured to receive a plurality of samples; a detection interface configured to amplify a target analyte and detect the target analyte to produce scan data; an instrument software interface configured to receive scan data and transfer the scan data to an assay analysis interface; the assay analysis interface configured to receive scan data, generate a detection result and transfer the detection result to the instrument software interface; the instrument software interface configured to receive a plurality of detection results, the instrument software interface comprising a non-transitory storage medium compromising a decision support generator, lab setting generator and storage database; the decision support generator having access to the storage medium, the decision support generator configured to apply at least one rule to each respective received detection result, to determine whether or not to attach a templated comment to the detection result to form a detection report, wherein: upon determining to approve attachment of a templated comment to the detection result based on application of at least one of the rules to the detection result, the decision support generator attached the detection result to the templated comments to form a detection report, the decision support generator forwards the detection report to the lab settings generator, the lab setting generator configured to auto release the detection report to the assay analysis interface or to store the detection report in the storage database; upon determining to release the detection report to the assay analysis interface the detection report is released to the assay analysis interface and the assay analysis interface releases the detection report to a hospital LIS.

Paragraph 2: A diagnostic instrument, comprising: a first interface configured to receive a plurality of samples; a detection interface configured to amplify a target analyte and detect the target analyte to produce scan data; an instrument software interface configured to receive scan data and transfer the scan data to an assay analysis interface; the assay analysis interface configured to receive scan data, generate a detection result and transfer the detection result to the instrument software interface; the instrument software interface configured to receive a plurality of detection results, the instrument software interface comprising a non-transitory storage medium compromising a decision support generator, lab setting generator and storage database; the decision support generator having access to the storage medium, the decision support generator configured to apply at least one rule to each respective received detection result, to Determine whether or not to attach a templated comment to the detection result to form a detection report, wherein: upon determining to approve attachment of a templated comment to the detection result based on application of at least one of the rules to the detection result, the decision support generator attached the detection result to the templated comments to form a detection report, the decision support generator forwards the detection report to the lab settings generator, the lab setting generator configured to auto release the detection report to the assay analysis interface or to store the detection report in the storage database; upon determining manual user approval is required for release the detection report to the assay analysis interface the detection report is released to the storage database for possible manual approval; upon manual approval the detection report, the detection report is released to the assay analysis interface and the assay analysis interface releases the detection report to a hospital LIS.

Paragraph 3: The diagnostic instrument of paragraph 1 or 2 wherein the decision support generator applies the rules based on the level of authority going from highest to lowest.

Paragraph 4: The diagnostic instrument of paragraph 1 or 2 wherein the decision support generator applies the rules based on the level of authority going from system administrator rules to laboratory overseer to hospital network overseer to hospital overseer to clinician.

Paragraph 5: The diagnostic instrument of paragraph 1 or 2 wherein the applied rule specifies a specific user selected from the group consisting of system administrator, laboratory overseer, hospital network overseer, hospital overseer or clinician.

Paragraph 6: The diagnostic instrument of paragraph 1 or 2 wherein the text of the templated comment can be changed by a user.

Paragraph 7: The diagnostic instrument of paragraph 1 or 2 wherein upon determining to approve attachment of a warning templated comment to the detection result based on application of at least one of the rules to the detection result, the decision support generator attaches the detection result to the templated comments to form a detection report, the decision support generator forwards the detection report to the storage database and to the lab settings generator, the lab setting generator configured to auto release the detection report to the assay analysis interface and the assay analysis interface releases the detection report to a hospital LIS.

Paragraph 8: A diagnostic instrument, comprising: a first interface configured to receive a plurality of samples; a detection interface configured to amplify a target analyte and detect the target analyte to produce scan data; an instrument software interface configured to receive scan data and transfer the scan data to an assay analysis interface; the assay analysis interface configured to receive scan data, generate a detection result and transfer the detection result to the instrument software interface; the instrument software interface configured to receive a plurality of detection results, the instrument software interface comprising a non-transitory storage medium compromising a decision support generator, lab setting generator and storage database; the decision support generator having access to the storage medium, the decision support generator configured to apply at least one rule to each respective received detection result, to determine whether or not to attach a templated comment to the detection result to form a detection report, wherein: upon determining to approve attachment of a templated comment to the detection result based on application of at least one of the rules to the detection result, the decision support generator attached the detection result to the templated comments to form a detection report, the decision support generator forwards the detection report to the lab settings generator, the lab setting generator configured to auto release the detection report to the assay analysis interface or to store the detection report in the storage database; upon determining to release the detection report to the assay analysis interface the detection report is released to the assay analysis interface and the assay analysis interface releases the detection report to a hospital LIS; upon determining to approve attachment of a templated comment to the detection result based on application of at least one of the rules to the detection result, the decision support generator attached the detection result to the templated comments to form a detection report, the decision support generator forwards the detection report to the lab settings generator, the lab setting generator configured to auto release the detection report to the assay analysis interface or to store the detection report in the storage database; upon determining manual user approval is required for release the detection report to the assay analysis interface the detection report is released to the storage database for possible manual approval; upon manual approval the detection report, the detection report is released to the assay analysis interface and the assay analysis interface releases the detection report to a hospital LIS.

The Methods of the Rules based management system can be further understood by the following numbered paragraphs:

Paragraph 1: A method for reporting diagnostic results, comprising: loading a patient sample into a diagnostic instrument; processing the patient sample to detect a target analyte and produce scan data; transferring the scan data to an instrument software interface; transferring the scan data from the instrument software interface to an assay analysis interface; generate a detection result; transfer the detection result to the instrument software interface; apply at least one rule to the detection result; determine whether or not to attach a templated comment to the detection result to form a detection report, wherein: upon determining to approve attachment of a templated comment to the detection result based on application of at least one of the rules to the detection result, attaching the detection result to the templated comments to form a detection report; forwarding the detection report to the lab settings generator; determining whether the detection report should be auto released or stored; upon determining that the detection report should be auto released the detection report is released to the assay analysis interface; and transferring the detection report to a hospital LIS.

Paragraph 2: A method for reporting diagnostic results, comprising: loading a patient sample into a diagnostic instrument; processing the patient sample to detect a target analyte and produce scan data; transferring the scan data to an instrument software interface; transferring the scan data from the instrument software interface to an assay analysis interface; generate a detection result; transfer the detection result to the instrument software interface; apply at least one rule to the detection result; determine whether or not to attach a templated comment to the detection result to form a detection report, wherein: upon determining to approve attachment of a templated comment to the detection result based on application of at least one of the rules to the detection result, attaching the detection result to the templated comments to form a detection report; forwarding the detection report to the lab settings generator; determining whether the detection report should be auto released or stored; upon determining that the detection report should not be auto released the detection report is released to the storage database for possible manual approval; upon manual approval the detection report, the detection report is released to the assay analysis interface; and transferring the detection report to a hospital LIS.

Paragraph 3: The method of paragraph 1 or 2 wherein the decision support generator applies the rules based on the level of authority going from highest to lowest.

Paragraph 4: The method of paragraph 1 or 2 wherein the decision support generator applies the rules based on the level of authority going from system administrator rules to laboratory overseer to hospital network overseer to hospital overseer to clinician.

Paragraph 5: The method of paragraph 1 or 2 wherein the applied rule specifies a specific user selected from the group consisting of system administrator, laboratory overseer, hospital network overseer, hospital overseer or clinician.

Paragraph 6: The method of paragraph 1 or 2 wherein the text of the templated comment can be changed by a user.

Paragraph 7: The method of paragraph 1 or 2 wherein upon determining to approve attachment of a warning templated comment to the detection result based on application of at least one of the rules to the detection result, attaching the detection result to the templated comments to form a detection report and forwarding the detection report to the storage database and to the lab settings generator, and releasing the detection report to the assay analysis interface and releasing the detection report to a hospital LIS.

The diagnostic instrument can be further understood by the following numbered paragraphs:

Paragraph 1: A diagnostic instrument, comprising: an interface configured to receive a plurality of samples in a cartridge; a non-transitory storage medium having rules stored thereon, the rules being configured to determine whether or not to associate a templated comment with a detection result; and a rule processing section having access to the storage medium, the rule processing section configured to apply at least one of the rules to each respective result obtained by the diagnostic instrument and associate a templated comment with a detection result.

Paragraph 2: The rules engine diagnostic instrument of paragraph 1, wherein the rules have rule parameters configured to analyze a detection result.

Paragraph 3: The rules engine diagnostic instrument of paragraph 1, wherein the parameters define whether a corresponding rule should apply to the detection result.

Paragraph 4: The rules engine diagnostic instrument of paragraph 1, wherein the parameters are adjustable from a first one of the plurality of levels to a second one of the plurality of levels based on a user type.

Paragraph 5: The rules engine diagnostic instrument of paragraph 1, wherein upon determining to automatically approve a templated comment, the rule processing section forwards the templated comment to an execution process for application.

Paragraph 6: The rules engine diagnostic instrument of paragraph 5, wherein upon determining to automatically reject a templated comment, the rule processing section forwards the templated comment to a manual user indicating that no templated comment was associated with a detection result.

Paragraph 7: The rules engine diagnostic instrument of paragraph 1, wherein upon determining to automatically approve a warning templated comment, the rule processing section forwards the templated comment with a warning to an execution process for application.

Paragraph 8: The rules engine diagnostic instrument of paragraph 1, wherein the rule parameters are configurable by user type.

Paragraph 9: The rules engine diagnostic instrument of paragraph 1, wherein the user type specifies a specific registered representative.

Paragraph 10: The rules engine diagnostic instrument of paragraph 1, wherein the registered representative specifies a system administrator, hospital network overseer, hospital overseer, clinician or combinations thereof.

Paragraph 11: The rules engine diagnostic instrument of paragraph 1, wherein when the result obtained is specified as invalid, the rejection templated comment is accompanied by a message that the result was invalid.

Paragraph 12: The rules engine diagnostic instrument of paragraph 1, wherein the message can be changed by a user type authorized to change a selected rule.

Paragraph 13: The rules engine diagnostic instrument of paragraph 1, wherein the warning templated comment is sent to a system administrator without being associated with a detection result.

Paragraph 14: A diagnostic instrument, comprising: an interface configured to receive a plurality of test orders, each test order containing a request for a sample to be processed for diagnosis; a non-transitory storage medium having rules stored thereon, the rules being configured to determine whether or not to apply templated comments, the rules having parameters configured to analyze the diagnostic data and a plurality of preset levels of scope of application; and a rule processing section having access to the storage medium, the rule processing section configured to apply at least one of the rules to each respective received detection result and level of the respective rule being within the specified scope assigned to each applied rule, to determine whether or not to associate a templated comment with the detection result.

Paragraph 15: The diagnostic instrument of paragraph 14, wherein each rule includes an assigned level of scope of application selected from a plurality of preset levels.

Paragraph 16: The diagnostic instrument of paragraph 15, each preset level of scope of application specifies a rule scope for which a corresponding rule should apply to all detection results for any source within the specified scope.

Paragraph 17: The diagnostic instrument of paragraph 16, the assigned level is adjustable from a first one of the plurality of preset levels to a second one of the plurality of preset levels based on a user setting.

Paragraph 18: The diagnostic instrument of paragraph 17; wherein each rule has an assigned outcome selected from a plurality of preset outcomes.

Paragraph 19: The diagnostic instrument of paragraph 18, wherein the assigned outcome is adjustable from a first one of the plurality of preset outcomes to a second one of the plurality of preset outcomes based on user setting.

Paragraph 20: The diagnostic instrument of paragraph 19, wherein upon determining to automatically approve a templated comment, the rule processing section forwards the templated comment to an execution process for application.

Paragraph 21: The diagnostic instrument of paragraph 19, wherein upon determining to automatically reject a templated comment, the rule processing section forwards the templated comment to a manual user indicating that no templated comment was associated with a detection result.

Paragraph 22: The diagnostic instrument of paragraph 19, wherein upon determining to automatically warn a templated comment, the rule processing section forwards the templated comment with a warning to an execution process for application.

Paragraph 23: The diagnostic instrument of paragraph 19, in which the assigned level of scope of application of an applied rule specifies a specific account.

Paragraph 24: The diagnostic instrument of paragraph 19, the text of said message can be changed by a user for a selected level.

The diagnostic instrument can be further understood by the following numbered paragraphs:

Paragraph 1: A method for configuring rules on a diagnostic instrument, comprising: selecting an assay type; selecting a target; selecting a target result; entering a rule identification number; entering a customizable comment; applying the rule thereby configuring rules on a diagnostic instrument.

Paragraph 2: The method of paragraph 1, wherein prior to step a user name and password are entered.

Paragraph 3: The method of paragraph 1, wherein each step is performed on a user interface on the diagnostic instrument.

Paragraph 4: The method of paragraph 1, wherein each step is performed on a user interface remotely connected to the diagnostic instrument.

Paragraph 5: A pathogen identification method comprising: receiving, by a computer processor of a diagnostic system a detection result associated with a patient sample; processing, by said computer processor the detection result wherein processing comprises subjecting the detection result to a at least one user configurable rule by said computer processor and determining if a templated comment should be associated with the detection result; associating the templated comment with the detection result; and dispatching, by said computer processor the detection result associated with the templated comment to a hospital LIS.

Paragraph 6: A method of configuring a system, the method comprising: providing a configuration system for receiving and reconciling one or more configuration rules pertaining to configuration attributes (data elements) from a plurality of patient samples, the configuration attributes having selectable parameters, and the configuration system comprising a rule reconciler that analyzes whether a first rule is compatible with a second rule, wherein the configuration rules are maintained on the configuration system or are maintained on a remote configuration system; receiving, by the configuration system, a first rule from a first user, the first rule pertaining to at least a first configuration attribute; storing the first rule on the configuration system at a rule storage location; receiving, by the configuration system, a second different rule from a second user, the second rule pertaining to at least the first configuration attribute; and comparing the second rule configuration attributes to the first rule configuration attributes to determine compatibility of the first rule with the second rule; and if the first rule configuration attributes are compatible with the second rule configuration attributes storing the second rule in the configuration system at the rule storage location. In some embodiments the first and second user are the same. In some embodiments the first and second user are the different.

Paragraph 7: A method of configuring a system, the method comprising: providing a configuration system for receiving and reconciling one or more configuration rules pertaining to configuration attributes (data elements) from a plurality of patient samples, the configuration attributes having selectable parameters, and the configuration system comprising a rule reconciler that analyzes whether a first rule is compatible with a second rule, wherein the configuration rules are maintained on the configuration system or are maintained on a remote configuration system; receiving, by the configuration system, a first rule from a first user, the first rule pertaining to at least a first configuration attribute; storing the first rule on the configuration system at the rule storage location; receiving, by the configuration system, a second same rule from a second user, the second rule having the same configuration attributes as the first rule; and comparing the second rule configuration attributes to the first rule configuration attributes to determine compatibility of the first rule with the second rule; and if the first rule configuration attributes are not compatible with the second rule configuration attributes storing the second rule in the configuration system at a database storage location.

It is intended that the foregoing detailed description be understood as an illustration of selected forms that the invention can take and not as a definition of the invention. It is only the following claims, including all equivalents, that are intended to define the scope of the claimed invention. Finally, it should be noted that any aspect of any of the embodiments described herein can be used alone or in combination with one another.

What is claimed is:

1. A pathogen detection device comprising:
a pathogen detector circuit configured to detect a target analyte in a patient sample, determine an identity of a pathogen from the target analyte, and generate a detection result including the identity of the pathogen;
a decision support generator circuit that receives the detection result and searches rules stored in a rule repository to detect at least one rule that corresponds to the detection result and in response to detecting the at least one rule, identifies decision support information and generates a signal based on the decision support information to create a detection report comprising the detection result and the decision support information; and
a circuit configured to display a graphical user interface to accept user input and change a hierarchy of the rules stored in the rule repository in response to the user input.

2. The pathogen detection device of claim 1, further comprising a communications interface, wherein the decision support generator circuit is further configured to cause the decision support information to be transmitted to a Laboratory Information System (LIS) via the communications interface.

3. The pathogen detection device of claim 1, further comprising a rule reconciler that is configured to automatically compare a new rule to an existing rule.

4. The pathogen detection device of claim 1, further comprising a Laboratory Information System (LIS) interchange in network communication with a LIS, wherein the LIS interchange is configured to receive the detection report from the decision support generator circuit and convert the detection report into a physician test result report, wherein the physician test result report contains the detection result and the decision support information.

5. The pathogen detection device of claim 1, wherein the graphical user interface provides a first field having a plurality of pre-populated choices for user selection, and wherein the graphical user interface provides the first field using a drop-down menu.

6. A method for providing treatment decision support for a patient having blood that is infected or possibly infected with a microorganism, the method comprising:
detecting the microorganism in the patient's blood sample, wherein detecting the microorganism comprises detecting, by a diagnostic instrument, a target analyte in a patient sample;
generating, by the diagnostic instrument, a detection result, which includes an identity of the microorganism;
altering a hierarchy of configurable rules stored in a rule repository in response to user input; and
generating decision support information by the diagnostic instrument, wherein generating the decision support information includes applying, by the diagnostic instrument, the altered hierarchy of configurable rules to the detection result, which, when evaluated, indicates whether to include corresponding decision support information in a detection report.

7. The method of claim 6, wherein each rule in the altered hierarchy of configurable rules comprises a corresponding IF condition, and wherein applying the altered hierarchy of configurable rules to the detection result comprises evaluating for each rule the corresponding IF condition supplied with information included in the detection result.

8. The method of claim 6, further comprising:
generating a detection report; and
converting the detection report into a physician test result report containing both the detection result and the decision support information for transmission to a Laboratory Information System (LIS) over a network.

9. A pathogen detection device comprising:
a display device; and
a processor configured to:
display, on the display device, a graphical user interface that provides a field for user input;
defining a rule based on the user input, wherein the rule is part of a hierarchy of rules, and wherein defining the rule affects the hierarchy;
apply the rule to a detection result evaluating whether the rule is satisfied; and
in response to the rule being satisfied, include decision support information defined in the rule as being associated with the detection result in a detection report.

10. The pathogen detection device of claim 9, wherein the graphical user interface provides the field using a drop-down menu.

11. A pathogen detection device comprising:
a display device; and
a processor configured to:
display, on the display device, a graphical user interface that provides a drop-down menu of a plurality of pre-populated choices for user selection;
receive a user selection of a pre-populated choice;
create a rule comprising an IF statement defined by the user selection of the pre-populated choice and a THEN statement defining corresponding decision support information, wherein the created rule is one of a plurality of rules in a hierarchy, and wherein creation of the rule alters the hierarchy of the plurality of rules;
apply the altered hierarchy of the plurality of rules to a detection result by evaluating whether the IF statement is satisfied; and
in response to the IF statement being satisfied, include the corresponding decision support information in a detection report.

12. The pathogen detection device of claim 11, wherein the processor is further configured to apply the altered hierarchy to the detection result, wherein a rule higher in the altered hierarchy is applied before a rule lower in the altered hierarchy.

13. The pathogen detection device of claim 12,
wherein the altered hierarchy comprises rules associated with a genus result and rules associated with a species result; and
wherein the processor is further configured to apply the rules associated with the genus result first and then apply the rules associated with the species result.

14. The pathogen detection device of claim 11, wherein each rule in the altered hierarchy comprises a condition for applying the rule, and wherein the processor is further configured to select which rules to apply based on which conditions are met.

15. The pathogen detection device of claim 14, wherein the conditions comprise one or more of the following: a particular time period, a particular account, a particular hospital, or a particular laboratory.

* * * * *